United States Patent
Gao et al.

(10) Patent No.: US 11,667,631 B2
(45) Date of Patent: Jun. 6, 2023

(54) FGFR4 INHIBITOR, PREPARATION METHOD THEREFOR, AND APPLICATIONS THEREOF

(71) Applicants: Jiangsu Hansoh Pharmaceutical Group Co., Ltd., Jiangsu (CN); Shanghai Hansoh Biomedical Co., Ltd., Shanghai (CN)

(72) Inventors: Peng Gao, Jiangsu (CN); Wenhua Xiu, Jiangsu (CN); Shaobao Wang, Jiangsu (CN); Lei Liu, Jiangsu (CN); Rudi Bao, Jiangsu (CN)

(73) Assignees: Jiangsu Hansoh Pharmaceutical Group Co., Ltd., Jiangsu (CN); Shanghai Hansoh Biomedical Co., Ltd., Shanghai (CN)

(*) Notice: Subject to any disclaimer, the term of this patent is extended or adjusted under 35 U.S.C. 154(b) by 0 days.

(21) Appl. No.: 16/302,374

(22) PCT Filed: May 16, 2017

(86) PCT No.: PCT/CN2017/084564
§ 371 (c)(1),
(2) Date: Nov. 16, 2018

(87) PCT Pub. No.: WO2017/198149
PCT Pub. Date: Nov. 23, 2017

(65) Prior Publication Data
US 2019/0276451 A1 Sep. 12, 2019

(30) Foreign Application Priority Data
May 20, 2016 (CN) .......................... 201610339009.4
Dec. 16, 2016 (CN) .......................... 201611166598.7

(51) Int. Cl.
C07D 471/04 (2006.01)
A61K 35/00 (2006.01)
A61K 31/551 (2006.01)
A61K 31/5386 (2006.01)
A61K 31/5355 (2006.01)
A61K 31/444 (2006.01)
A61K 31/553 (2006.01)

(52) U.S. Cl.
CPC .......... *C07D 471/04* (2013.01); *A61K 31/444* (2013.01); *A61K 31/5355* (2013.01); *A61K 31/5386* (2013.01); *A61K 31/551* (2013.01); *A61K 31/553* (2013.01); *A61K 35/00* (2013.01); *Y02P 20/55* (2015.11)

(58) Field of Classification Search
None
See application file for complete search history.

(56) References Cited

U.S. PATENT DOCUMENTS

| | | | |
|---|---|---|---|
| 2015/0119385 A1* | 4/2015 | Buschmann | A61K 31/55 514/215 |
| 2020/0199120 A1* | 6/2020 | Zhang | A61K 31/4375 |

FOREIGN PATENT DOCUMENTS

| WO | 2015059668 A1 | 4/2015 |
|---|---|---|
| WO | 2016151500 A1 | 9/2016 |
| WO | 2016151501 A1 | 9/2016 |

OTHER PUBLICATIONS

Chemical Abstract Registry No. 1709021-57-7, indexed in the Registry File on Stn Cas Online May 20, 2015.*
Int'l Search Report and Written Opinion dated Aug. 28, 2017 in Int'l Application No. PCT/CN2017/084564.

* cited by examiner

*Primary Examiner* — Po-Chih Chen
(74) *Attorney, Agent, or Firm* — Ice Miller LLP

(57) ABSTRACT

The present invention relates to an FGFR4 inhibitor having a structure represented by formula (I), preparation method therefor, and applications thereof. A series of compounds represented by formula (I) in the present invention have very-strong inhibition effect on the activity of FGFR4 kinase, have very-high selectivity, can be widely used in the preparation of drugs for treating cancers, specially a liver cancer, a stomach cancer, a prostate cancer, a skin cancer, an ovarian cancer, a lung cancer, a breast cancer or a colon cancer, and can be developed into a new-generation FGFR4 inhibitor drug.

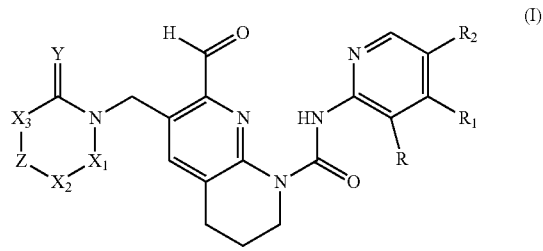

16 Claims, No Drawings

FGFR4 INHIBITOR, PREPARATION METHOD THEREFOR, AND APPLICATIONS THEREOF

CROSS-REFERENCE TO RELATED APPLICATIONS

This application is a Section 371 of International Application No. PCT/CN2017/084564, filed May 16, 2017, which was published in the Chinese language on Nov. 23, 2017, under International Publication No. WO 2017/198149 A1, which claims priority under 35 U.S.C. § 119(b) to Chinese Application No. 201610339009.4, filed May 20, 2016 and Chinese Application No. 201611166598.7, filed Dec. 16, 2016, the disclosures of which are incorporated herein by reference in its/their entirety.

FIELD OF THE INVENTION

The present invention belongs to the field of pharmaceutical synthesis, specifically relates to an FGFR4 inhibitor, preparation method and use thereof

BACKGROUND OF THE INVENTION

Fibroblast growth factor receptor (FGFR) belongs to transmembrane receptor of the receptor tyrosine kinase, and includes four receptor subtypes, namely FGFR1, FGFR2, FGFR3 and FGFR4. FGFR regulates various functions such as cell proliferation, survival, differentiation and migration, and plays an important role in human development and adult body functions. Expression of FGFR is abnormal in a variety of human tumors, including gene amplication, mutation, and overexpression, therefore FGFR is a vital target for tumor-targeted therapeutic research.

FGFR4 is a member of FGFR receptor family and can form dimers on the cell membrane by binding to its ligand, fibroblast growth factor 19 (FGF19). The formation of these dimers can cause the phosphorylation of key tyrosine residues in FGFR4's own cells, thereby activating multiple downstream signaling pathways in cells. These intracellular signaling pathways play an important role in cell proliferation, survival and anti-apoptosis. FGFR4 is overexpressed in many cancers and thus is a predictor of malignant tumor invasion. Decreasing and reducing FGFR4 expression can reduce cell proliferation and promote cell apoptosis. Recently, more and more studies have shown that the signaling pathways of FGF19/FGFR4 is continuously activated in about one-third of liver cancer patients, which is the main carcinogenic factor leading to liver cancer in this type of patients. Meanwhile, expression or high expression of FGFR4 is also closely related to many other tumors, such as gastric cancer, prostate cancer, skin cancer, ovarian cancer, lung cancer, breast cancer, colon cancer, etc.

The incidence of liver cancer in China is the highest in the world, and the number of new patients and dead patients each year is about half of the total number of liver cancer in the world. At present, the incidence of liver cancer in China is about 28.7 per 100 thousand people, and 394770 new cases were found in 2012, therefore liver cancer becomes the third malignant tumor after gastric cancer and lung cancer.

The onset of primary liver cancer with the features of high invasiveness and poor prognosis is a multi-factor, multi-step complex process. Surgical treatment such as liver resection and liver transplantation can improve the survival rate of some patients, but only limited patients can undergo surgical treatment and most patients have a poor prognosis due to recurrence and metastasis afer surgery. Sorafenib is the only drug approved on the market for the treatment of liver cancer, but the clinically overall survival can only be extended for about 3 months, and the treatment effect is not satisfying. Therefore, it is urgent to develop a liver cancer system treatment drug with new molecules. Since FGFR4 is a major carcinogenic factor of a considerable part of liver cancer, the development of small molecule inhibitors of FGFR4 has significant potentiality in clinical application.

At present, some FGFR inhibitors as anti-tumor drugs have entered into the clinical research phase, but these drugs are mainly inhibitors of FGFR1, 2 and 3, the inhibition of FGFR4 activity is weak, and the inhibition of FGFR1-3 has target-related side effects such as hyperphosphatemia. Highly selective inhibitors of FGFR4 can be effective in the treatment of cancer diseases caused by abnormal FGFR4 signaling pathway, and can avoid the side effects such as caused by the inhibition of FGFR1-3. Therefore, highly selective small molecule inhibitors against FGFR4 have great application prospects in the field of tumor targeted therapy.

SUMMARY OF THE INVENTION

During the course of research, the inventors found a FGFR4 inhibitor having the structure of formula (I), which has a strong inhibitory effect on FGFR4 kinase activity and has a very high selectivity, and can be used as a medicant to treat cancer, specially liver cancer, gastric cancer, prostate cancer, skin cancer, ovarian cancer, lung cancer, breast cancer or colon cancer and is expected to be developed into a new generation of FGFR4 inhibitor drugs.

In the first aspect, the present invention provides a compound of formula (I), a stereoisomer or a pharmaceutically acceptable salt thereof:

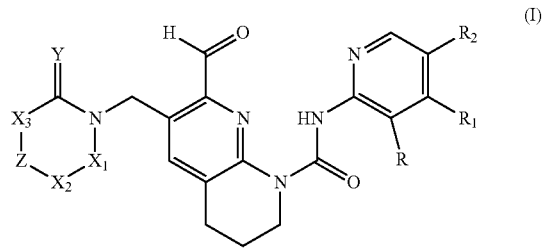

(I)

wherein:

$X_1$ is —$(CR_3R_4)m_1$—; $X_2$ is —$(CR_5R_6)m_2$—; $X_3$ is —$(CR_7R_8)m_3$—;

Y is selected from the group consisting of O and S;

Z is selected from the group consisting of $NX_4$, O and S;

$X_4$ is selected from the group consisting of hydrogen, deuterium, $C_{1-8}$ alkyl, $C_{3-8}$ cycloalkyl and halo$C_{1-8}$ alkyl;

R is selected from the group consisting of hydrogen, deuterium, halogen, hydroxy, thiol, cyano, nitro, azido, $C_{1-8}$ alkyl, halo$C_{1-8}$ alkyl, $C_{3-8}$ cycloalkyl, 3-8 membered heterocyclyl, 3-8 membered heterocyclyloxy, 3-8 membered heterocyclylthio, —$C_{0-8}$—S(O)$_r$$R_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —N($R_{12}$)—C(O)$R_{11}$ and —N($R_{12}$)—C(O)O$R_{10}$;

$R_1$ is selected from the group consisting of hydrogen, deuterium, halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3-8 membered heterocyclyl, 3-8 membered heterocyclyloxy, 3-8 membered heterocyclylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$, optionally substituted by one or more groups selected from the group consisting of halogen, hydroxy, alkyl, alkoxy, haloC$_{1-8}$ alkyl, C$_{3-8}$ cycloalkyl, 3-8 membered heterocyclyl, 3-8 membered heterocyclyloxy, 3-8 membered heterocyclylthio, C$_{1-8}$ alkoxy-substituted 3-8 membered heteroaryl, C$_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$;

R$_2$ is selected from the group consisting of halogen, hydroxy, thiol, cyano, thiocyano, nitro, azido, C$_{1-8}$ alkyl, C$_{2-8}$ alkenyl, C$_{2-8}$ alkynyl, C$_{3-8}$ cycloalkyl, 3-8 membered heterocyclyl, C$_{1-8}$ alkyloxy, C$_{3-8}$ cycloalkoxy and 3-8 membered heterocyclyloxy, optionally substituted by one or more groups selected from the group consisting of halogen, hydroxy, thiol, cyano, nitro, azido, C$_{1-8}$ alkyl, C$_{2-8}$ alkenyl, C$_{2-8}$ alkynyl, haloC$_{1-8}$ alkyl, C$_{3-8}$ cycloalkyl, 3-8 membered heterocyclyl, 3-8 membered heterocyclyloxy, 3-8 membered heterocyclylthio, C$_{5-10}$ aryl, C$_{5-10}$ aryloxy, C$_{5-10}$ arylthio, 5-10 membered heteroaryl, 5-10 membered heteroaryloxy, 5-10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$;

R$_3$, R$_4$, R$_5$, R$_6$, R$_7$ and R$_8$ are each independently selected from the group consisting of hydrogen, deuterium, halogen, C$_{1-8}$ alkyl, C$_{2-8}$ alkenyl, C$_{2-8}$ alkynyl, haloC$_{1-8}$ alkyl, C$_{3-8}$ cycloalkyl, 3-8 membered heterocyclyl, C$_{1-8}$ alkoxy, haloC$_{1-8}$ alkoxy, C$_{3-8}$ cycloalkoxy and 3-8 membered heterocyclyloxy, or, R$_3$ and R$_4$, R$_5$ and R$_6$, R$_7$ and R$_8$ together with the carbon atom to which they are directly attached form a 3-5 membered cycloalkyl or 3-5 membered heterocyclyl;

R$_9$ is selected from the group consisting of hydrogen, deuterium, C$_{1-8}$ alkyl, C$_{2-8}$ alkenyl, C$_{3-8}$ cycloalkyl, 3-8 membered heterocyclyl, haloC$_{1-8}$ alkyl, phenyl, p-methylphenyl, amino, mono C$_{1-8}$ alkylamino, di C$_{1-8}$ alkylamino and C$_{1-8}$ alkanoylamino;

R$_{10}$ is selected from the group consisting of hydrogen, deuterium, C$_{1-8}$ alkyl, C$_{3-8}$ cycloalkyl, C$_{5-10}$ aryl, 3-8 membered heterocyclyl, haloC$_{1-8}$ alkyl and hydroxyC$_{1-8}$ alkyl;

R$_{11}$ is selected from the group consisting of hydrogen, deuterium, C$_{1-8}$ alkyl, C$_{1-8}$ alkoxy, C$_{3-8}$ cycloalkyl, C$_{3-8}$ cycloalkoxy, haloC$_{1-8}$ alkyl, haloC$_{1-8}$alkoxy, hydroxyC$_{1-8}$ alkyl and hydroxyC$_{1-8}$ alkoxy;

R$_{12}$ and R$_{13}$ are each independently selected from the group consisting of hydrogen, deuterium, C$_{1-8}$ alkyl, C$_{1-8}$ alkoxy-substituted C$_{1-8}$ alkyl, C$_{3-8}$ cycloalkyl-substituted C$_{1-8}$ alkyl, C$_{2-8}$ alkenyl, C$_{2-8}$ alkynyl, C$_{3-8}$ cycloalkyl, 3-8 membered heterocyclyl, C$_{5-10}$ aryl, 5-10 membered heteroaryl and C$_{1-8}$ alkanoyl;

m$_1$, m$_2$ and m$_3$ are each independently selected from the group consisting of 0, 1 and 2, provided that m$_1$ and m$_2$ are not 0 at the same time; and r is 0, 1 or 2.

In a further preferred embodiment, the compound of formula (I), the stereoisomer or the pharmaceutically acceptable salt thereof, is a compound of formula (II):

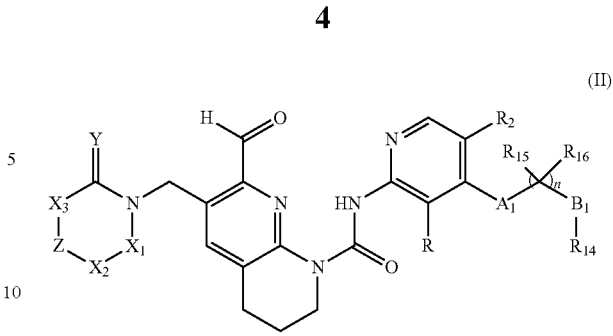

(II)

wherein:

A$_1$ is selected from the group consisting of a bond, NX$_4$, O and S;

B$_1$ is selected from the group consisting of a bond, O and a cycle, and the cycle is selected from the group consisting of C$_{3-8}$ cycloalkyl, 3-8 membered heterocyclyl, C$_{3-8}$ cycloalkyl-substituted C$_{1-8}$ alkyl, C$_{5-10}$ aryl and 5-10 membered heteroaryl;

R is selected from the group consisting of hydrogen, deuterium, halogen, hydroxy, thiol, cyano, nitro, azido, C$_{1-8}$ alkyl, haloC$_{1-8}$ alkyl, C$_{3-8}$ cycloalkyl and 3-8 membered heterocyclyl;

R$_{14}$ is selected from the group consisting of hydrogen, halogen, C$_{1-8}$ alkyl, haloC$_{1-8}$ alkyl, C$_{1-8}$ alkoxy, C$_{3-8}$ cycloalkyl, 3-8 membered heterocyclyl, 3-8 membered heterocyclyloxy, 3-8 membered heterocyclylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$;

R$_{15}$ and R$_{16}$ are each independently selected from the group consisting of hydrogen, halogen, hydroxy, alkyl, haloC$_{1-8}$ alkyl, C$_{3-8}$ cycloalkyl, 3-8 membered heterocyclyl, 3-8 membered heterocyclyloxy, 3-8 membered heterocyclylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$;

or R$_{15}$ and R$_{16}$ together with the carbon atom to which they are directly attached form a cycloalkyl or heterocyclyl, and the cycloalkyl or heterocyclyl is optionally substituted by one or more groups selected from the group consisting of C$_{1-8}$ alkyl, haloC$_{1-8}$ alkyl, halogen, hydroxy, C$_{1-8}$ alkoxy and hydroxyC$_{1-8}$ alkyl;

n is selected from the group consisting of 0, 1, 2, 3 and 4;

Z, Y, X$_1$-X$_3$ and R$_2$ are as defined in the compound of formula (I).

In a more further preferred embodiment, in the compound of formula (II), the stereoisomer or the pharmaceutically acceptable salt thereof, R is selected from the group consisting of hydrogen and fluorine; R$_2$ is selected from the group consisting of cyano and thiocyano;

B$_1$ is selected from the group consisting of cyclopropyl, cyclobutyl, cyclopentyl, oxetanyl, thietanyl, azetidinyl, furanyl, thienyl, pyrrolyl, imidazolyl, pyrazolyl, pyridyl, oxazolyl, thiazolyl, tetrahydrofuranyl, tetrahydrothienyl, tetrahydropyrrolyl, tetrahydroimidazolyl, tetrahydropyranyl, piperazinyl and morpholinyl;

R$_{14}$ is selected from the group consisting of hydrogen, fluorine, chlorine, methoxy, ethoxy, trifluoromethyl, cyclopropyl, —$C_{0-8}$—O—R$_{10}$, —$C_{0-8}$—C(O)OR$_{10}$, —$C_{0-8}$—C(O)R$_{11}$ and —$C_{0-8}$—O—C(O)R$_{11}$;

preferably, when R$_{14}$ and —(CR$_{15}$R$_{16}$)$_n$— are attached to the adjacent ring atoms of B$_1$, the stereoisomer includes the following configurations: (R)—R$_{14}$ and (S)—(CR$_{15}$R$_{16}$)$_n$—, (S)—R$_{14}$ and (R)—(CR$_{15}$R$_{16}$)$_n$—, (R)—R$_{14}$ and (R)—(CR$_{15}$R$_{16}$)$_n$—, or (S)—R$_{14}$ and (S)—(CR$_{15}$R$_{16}$)$_n$—;

preferably, when —R$_{14}$ and —(CR$_{15}$R$_{16}$)$_n$ are attached to the same ring atom of B$_1$, the stereoisomer includes the following configurations: (R)—R$_{14}$ and (S)—(CR$_{15}$R$_{16}$)$_n$—, or (S)—R$_{14}$ and (R)—(CR$_{15}$R$_{16}$)n—;

Z, Y, X$_1$-X$_3$, A$_1$, R$_{15}$ and R$_{16}$ are as defined in the compound of formula (II).

In the most preferred embodiment, the compound of formula (I), the stereoisomer or the pharmaceutically acceptable salt thereof is selected from the group consisting of:

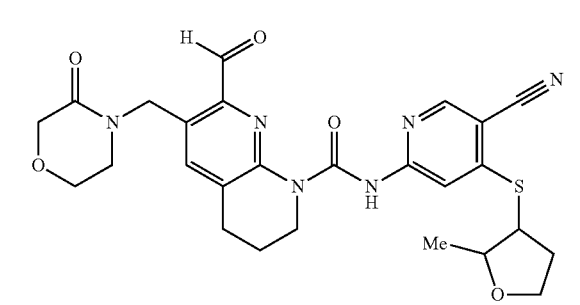

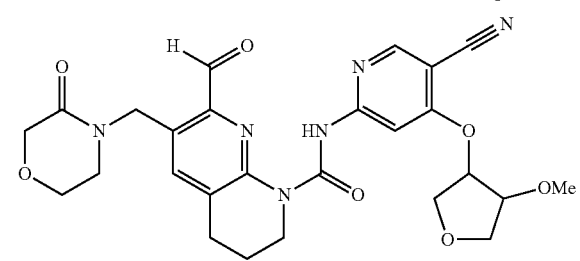

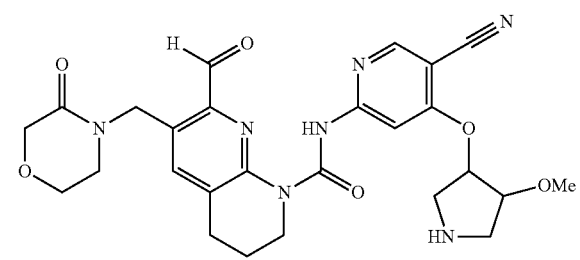

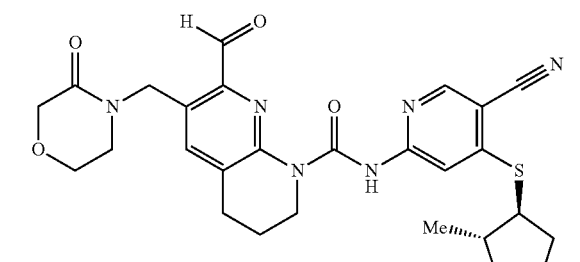

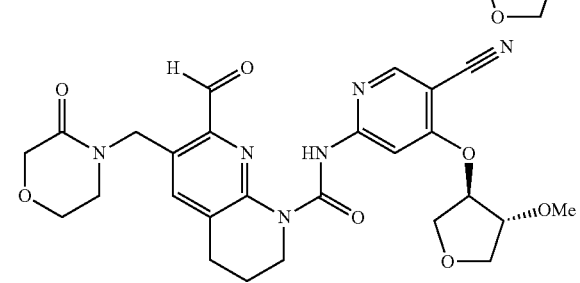

-continued

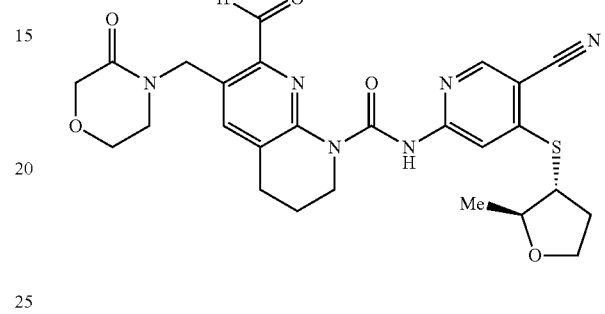

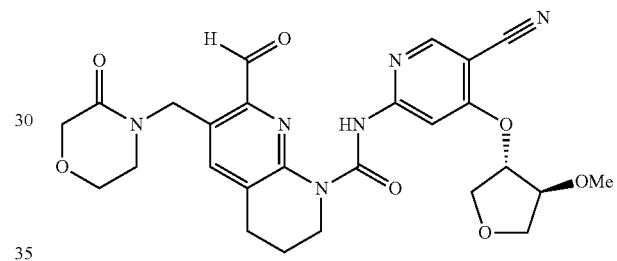

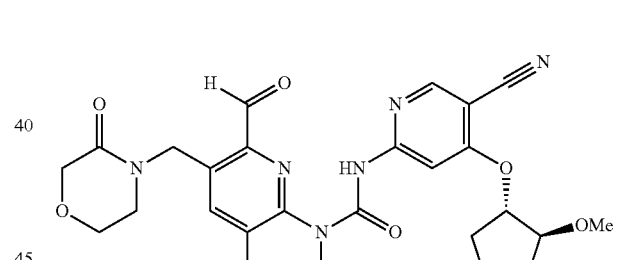

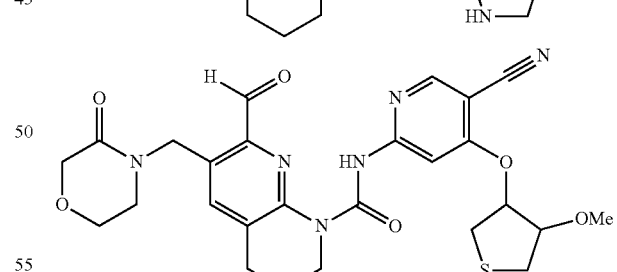

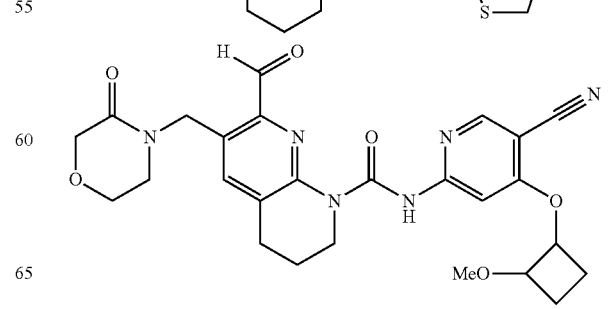

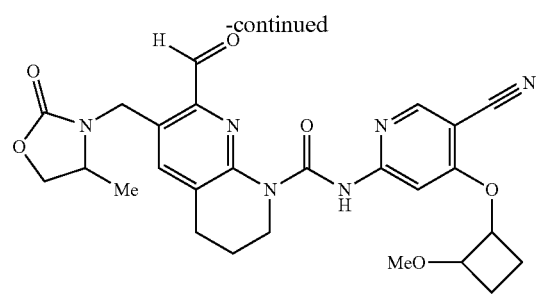
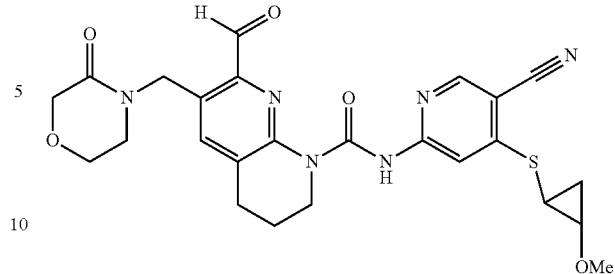
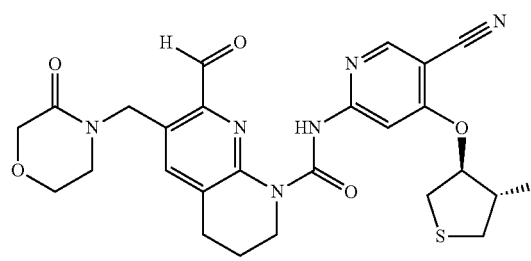
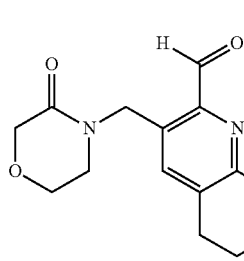
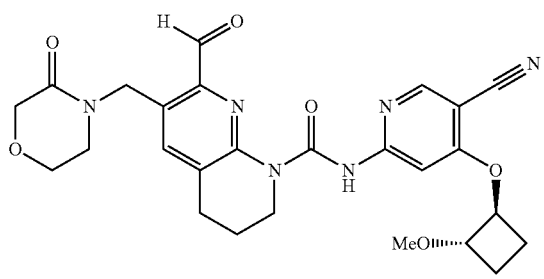
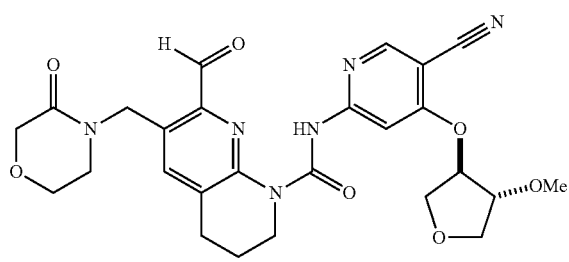
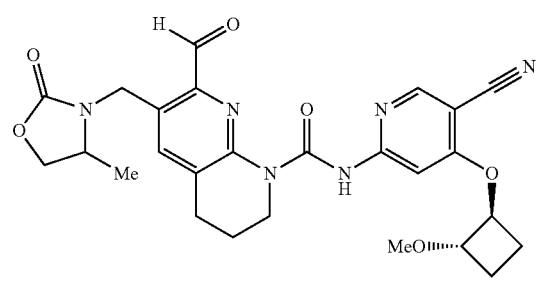
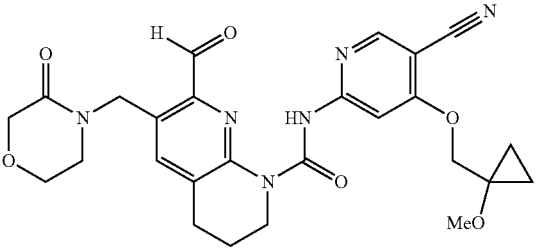
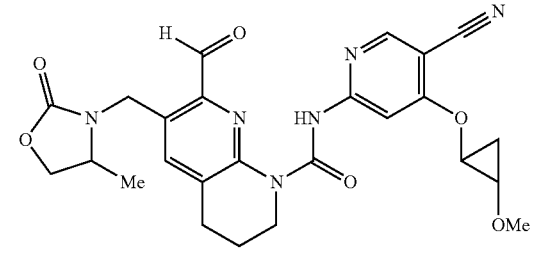
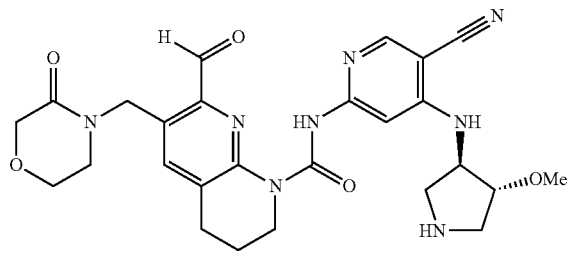
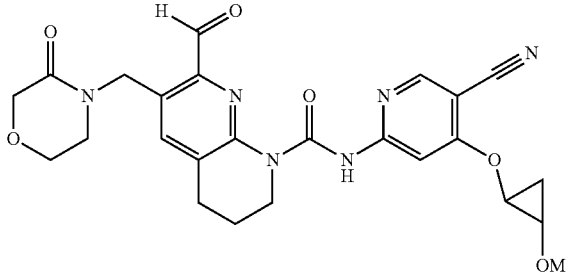
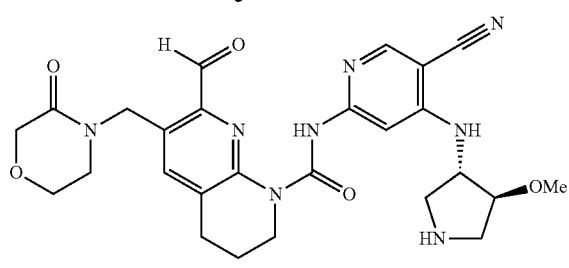

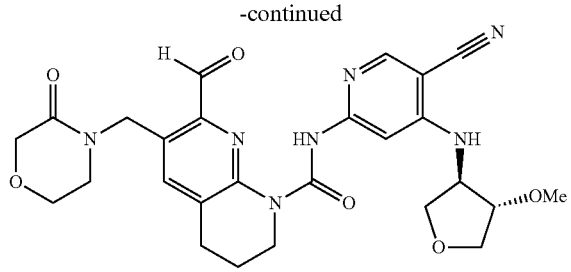
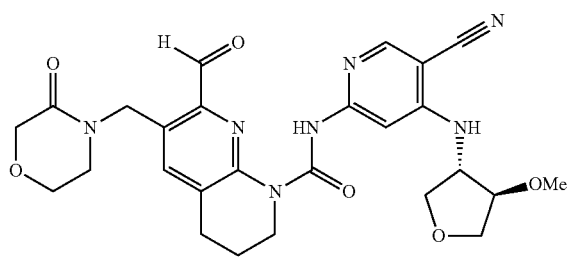
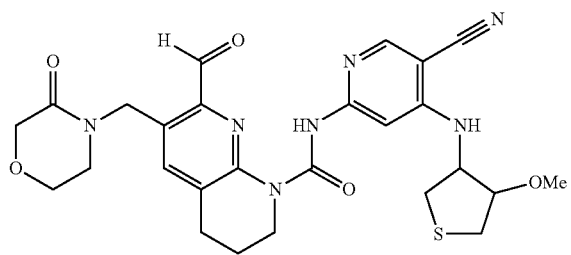
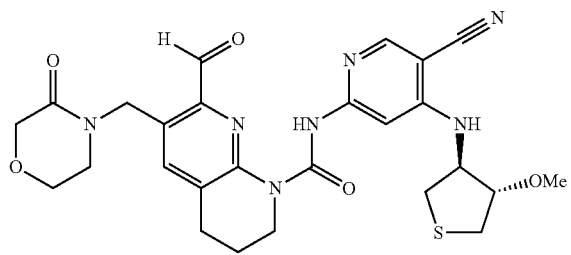
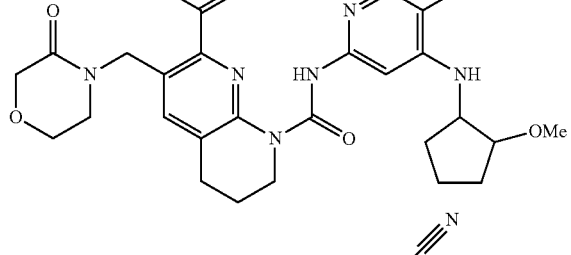
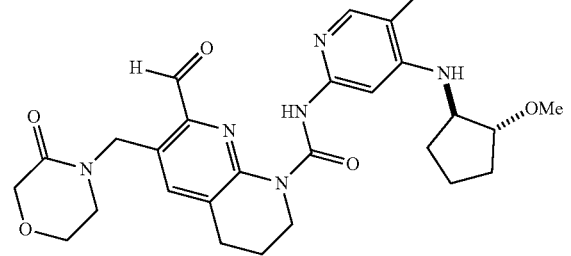
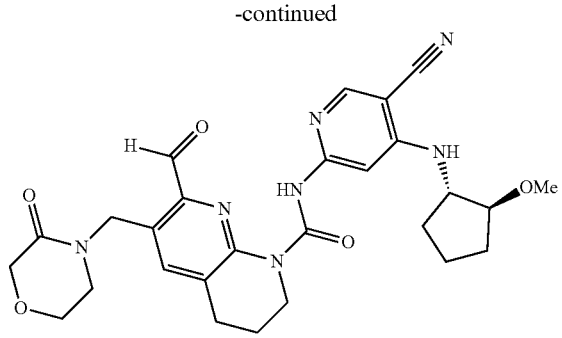
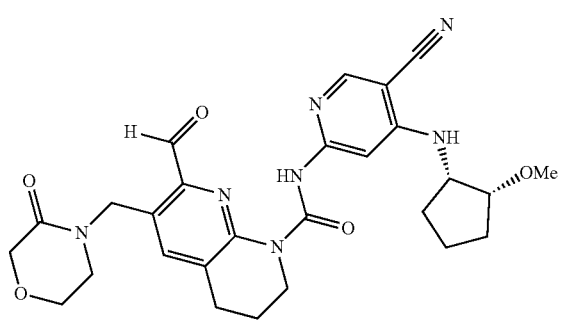
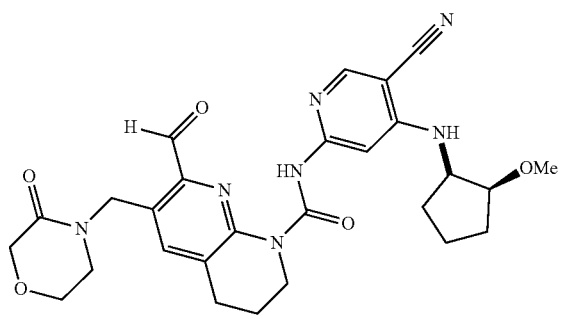
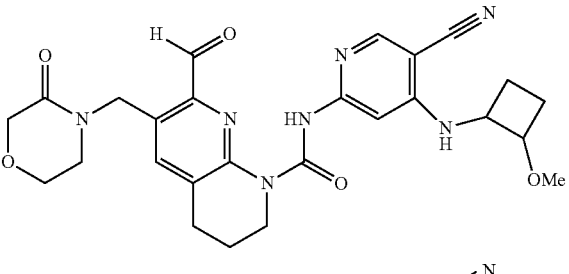
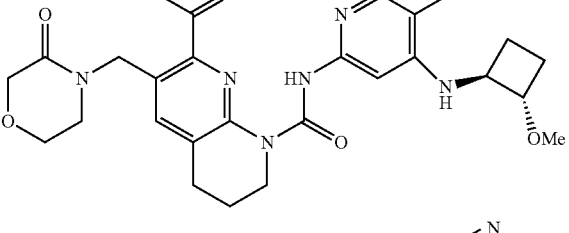
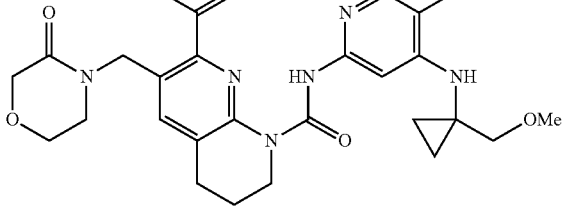

11
-continued
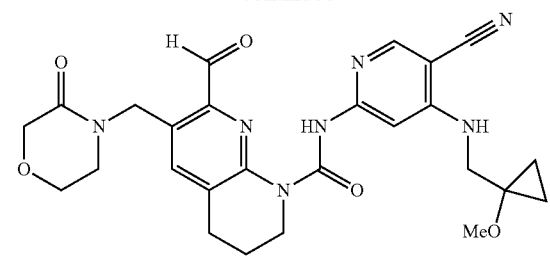
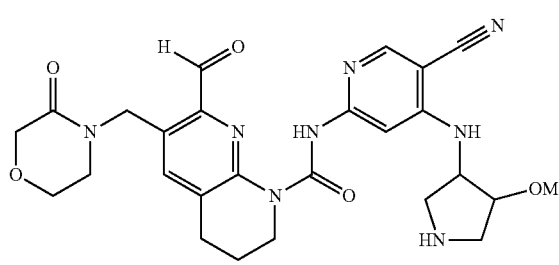
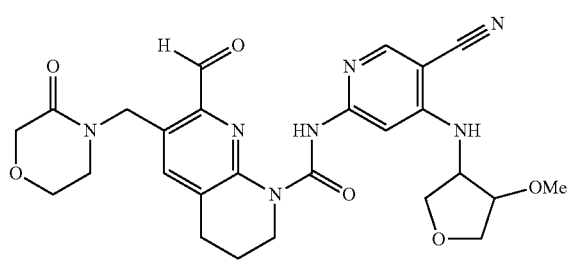
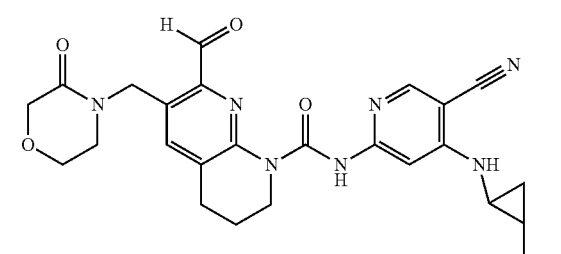
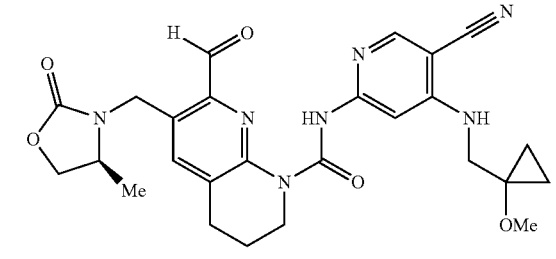
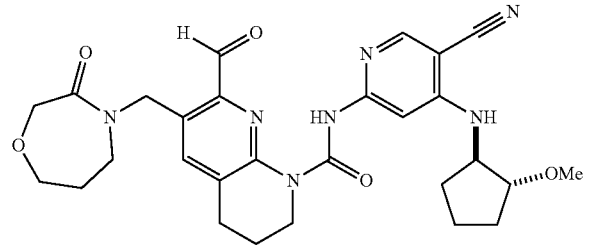
12
-continued
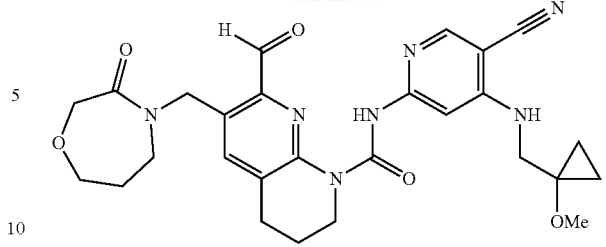
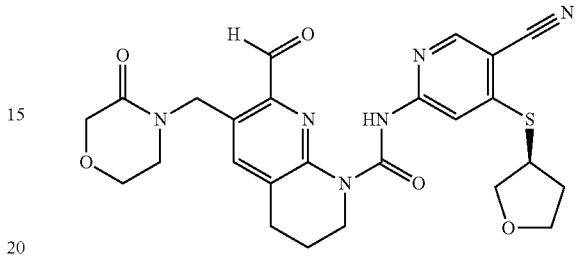
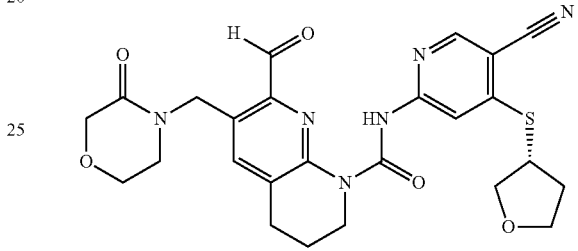
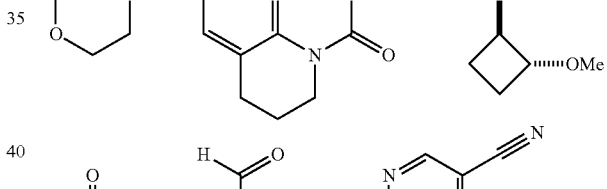
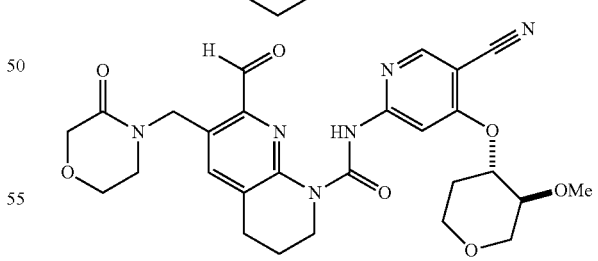
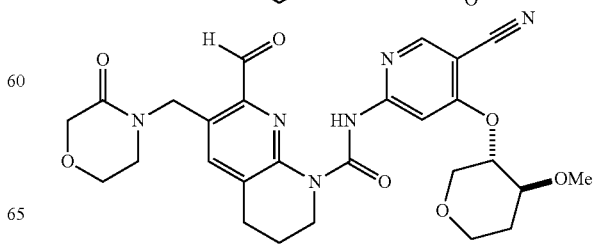

-continued

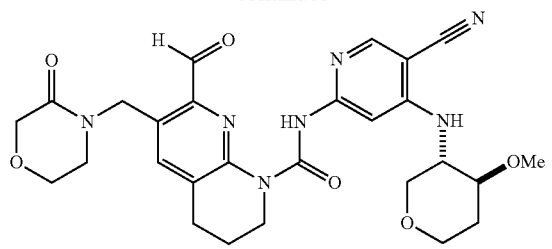

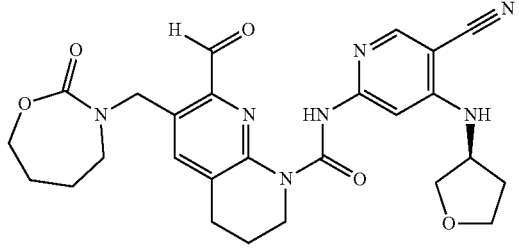

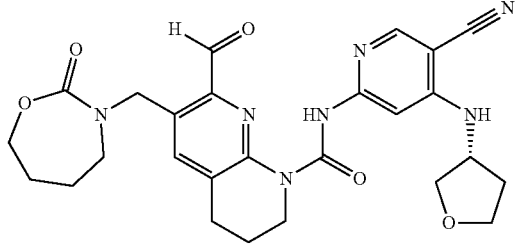

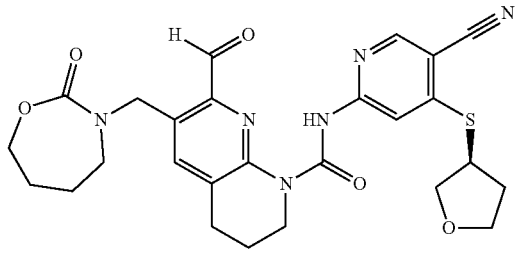

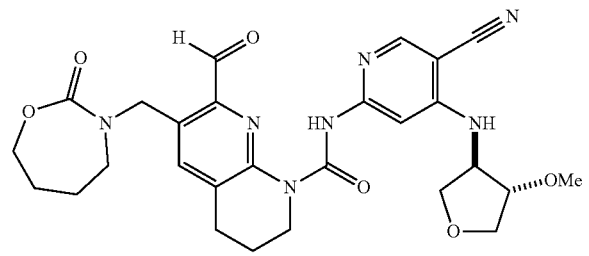

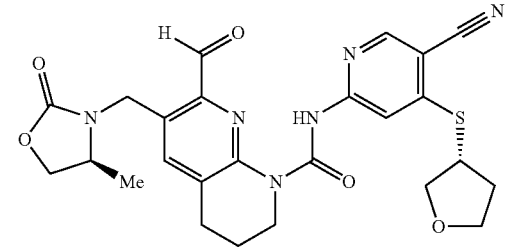

-continued

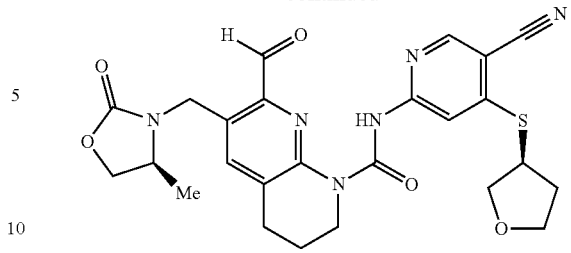

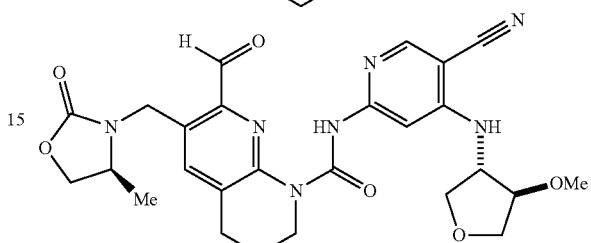

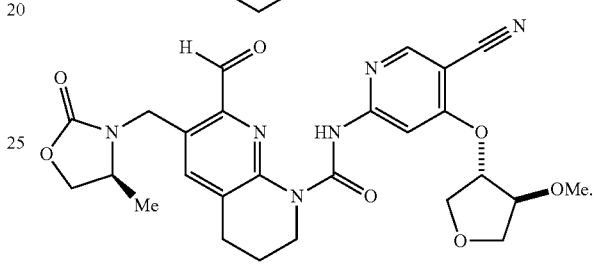

In a more further preferred embodiment, the compound of formula (II), the stereoisomer or the pharmaceutically acceptable salt thereof, characterized in that:

R is selected from the group consisting of hydrogen and fluorine; $R_2$ is selected from the group consisting of cyano and thiocyano; $B_1$ is selected from the group consisting of phenyl and pyridyl;

$R_{14}$ is selected from the group consisting of fluorine, chlorine, methoxy, ethoxy, trifluoromethyl, cyclopropyl, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —N($R_{12}$)—C(O)$R_{11}$ and —N($R_{12}$)—C(O)O$R_{10}$;

n is selected from the group consisting of 0 and 1;

more preferably, when —$R_{14}$ and —$A_1$— are attached to the adjacent carbon atoms of phenyl, the stereoisomer includes the following configurations: (R)—$R_{14}$ and (S)—$A_1$—, (S)—$R_{14}$ and (R)—$A_1$—, (R)—$R_{14}$ and (R)—$A_1$—, or (S)—$R_{14}$ and (S)—$A_1$—;

Z, Y, $X_1$-$X_3$, $A_1$, $R_{15}$ and $R_{16}$ are as defined in the compound of formula (II).

In the most preferred embodiment, the compound of formula (I), the stereoisomer or the pharmaceutically acceptable salt thereof is selected from the group consisting of:

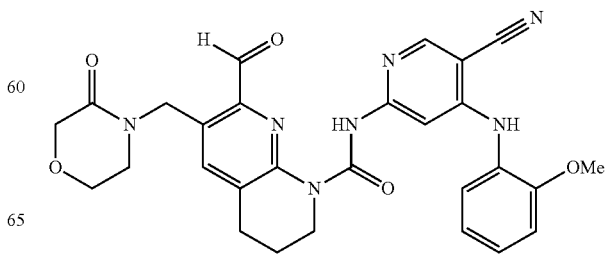

-continued

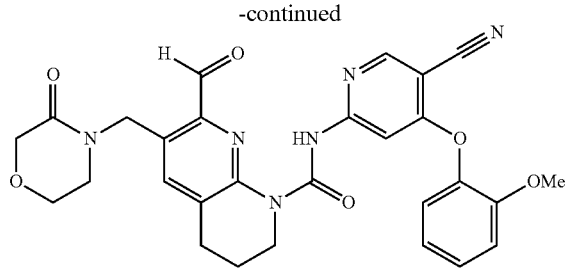

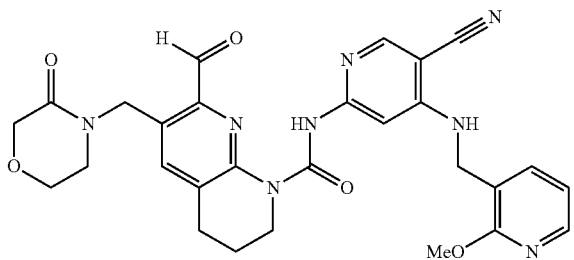

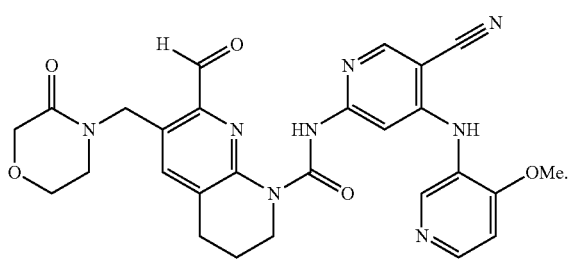

In a further preferred embodiment, the compound of formula (I), the stereoisomer or the pharmaceutically acceptable salt thereof is a compound of formula (III):

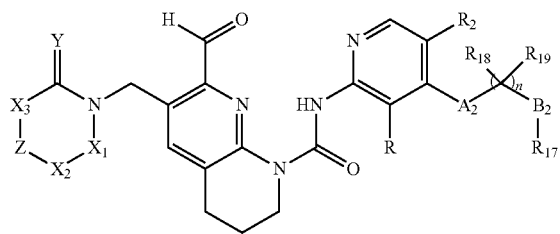

(III)

wherein:

A$_2$ is selected from the group consisting of a bond, NX$_4$, O and S;

B$_2$ is selected from the group consisting of C$_{1-8}$ alkyl, C$_{1-8}$ alkoxy and C$_{1-8}$ alkoxy-substituted C$_{1-8}$ alkyl;

R is selected from the group consisting of hydrogen, deuterium, halogen, hydroxy, thiol, cyano, nitro, azido, C$_{1-8}$ alkyl, haloC$_{1-8}$ alkyl, C$_{3-8}$ cycloalkyl and 3-8 membered heterocyclyl;

R$_{17}$ is selected from the group consisting of hydrogen, C$_{1-8}$ alkyl, halogen, haloC$_{1-8}$ alkyl, C$_{3-8}$ cycloalkyl, 3-8 membered heterocyclyl, 3-8 membered heterocyclyloxy, 3-8 membered heterocyclylthio, —C$_{0-8}$—S(O)$_r$R$_9$, —C$_{0-8}$—O—R$_{10}$, —C$_{0-8}$—C(O)OR$_{10}$, —C$_{0-8}$—C(O)R$_{11}$, —C$_{0-8}$—O—C(O)R$_{11}$, —C$_{0-8}$—NR$_{12}$R$_{13}$, —C$_{0-8}$—C(O)NR$_{12}$R$_{13}$, —N(R$_{12}$)—C(O)R$_{11}$ and —N(R$_{12}$)—C(O)OR$_{10}$;

R$_{18}$ and R$_{19}$ are each independently selected from the group consisting of halogen, hydroxy, alkyl, haloC$_{1-8}$ alkyl, C$_{3-8}$ cycloalkyl, 3-8 membered heterocyclyl, 3-8 membered heterocyclyloxy, 3-8 membered heterocyclylthio, —C$_{0-8}$—S(O)$_r$R$_9$, —C$_{0-8}$—O—R$_{10}$, —C$_{0-8}$—C(O)OR$_{10}$, —C$_{0-8}$—C(O)R$_{11}$, —C$_{0-8}$—O—C(O)R$_{11}$, —C$_{0-8}$—NR$_{12}$R$_{13}$, —C$_{0-8}$—C(O)NR$_{12}$R$_{13}$, —N(R$_{12}$)—C(O)R$_{11}$ and —N(R$_{12}$)—C(O)OR$_{10}$;

or R$_{18}$ and R$_{19}$ together with the carbon atom to which they are directly attached form a cycloalkyl or heterocyclyl, wherein the cycloalkyl or heterocyclyl is optionally substituted by one or more groups selected from the group consisting of C$_{1-8}$ alkyl, haloC$_{1-8}$ alkyl, halogen, hydroxy, C$_{1-8}$ alkoxy and hydroxyC$_{1-8}$ alkyl;

n is selected from the group consisting of 0, 1, 2, 3, and 4.

In a more further preferred embodiment, in the compound of formula (III), the stereoisomer or the pharmaceutically acceptable salt thereof, R is selected from the group consisting of hydrogen and fluorine; R$_2$ is selected from the group consisting of cyano and thiocyano;

B$_2$ is selected from the group consisting of methyl, ethyl, methoxy, ethoxy, methoxyethyl, ethoxymethyl and ethoxyethyl;

R$_{17}$ is selected from the group consisting of hydrogen, methyl, methoxy, ethoxy, isopropoxy, cyclopropyl, cyclobutyl, cyclopentyl, cyclopropyloxy, cyclobutyloxy, cyclopentyloxy, furanyl, thienyl, pyrrolyl, imidazolyl, tetrahydrofuranyl, tetrahydrothienyl, tetrahydropyrrolyl, tetrahydroimidazolyl, piperazinyl and morpholinyl; and R$_3$, R$_4$, R$_5$, R$_6$, R$_7$ and R$_8$ are each independently selected from the group consisting of hydrogen, deuterium, fluorine, chlorine, methyl, ethyl, isopropyl, methoxy, ethoxy and isopropoxy.

In the most preferred embodiment, the compound of formula (I), the stereoisomer or the pharmaceutically acceptable salt thereof is selected from the group consisting of:

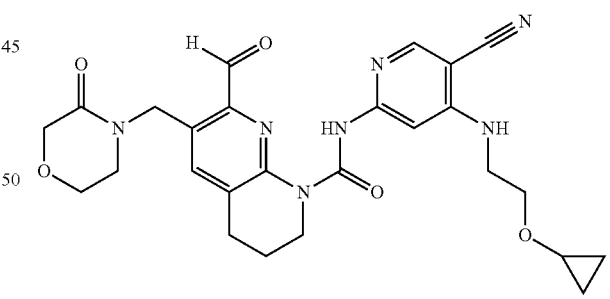

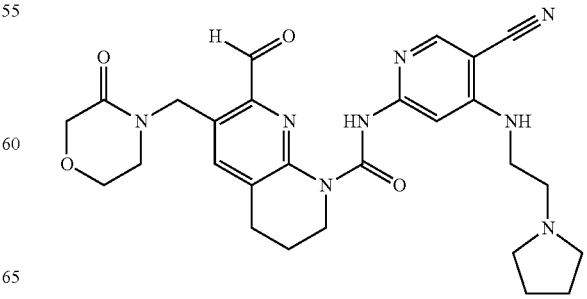

17
-continued
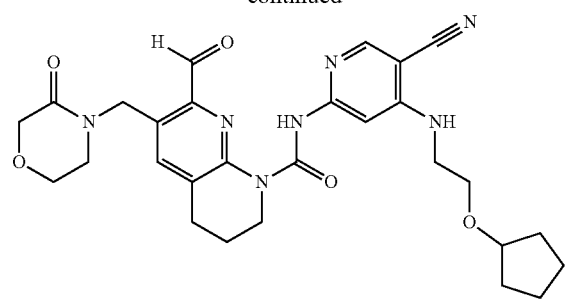
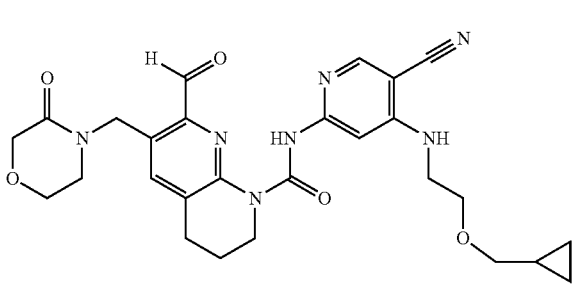
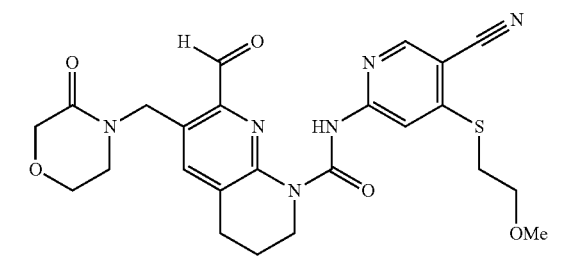
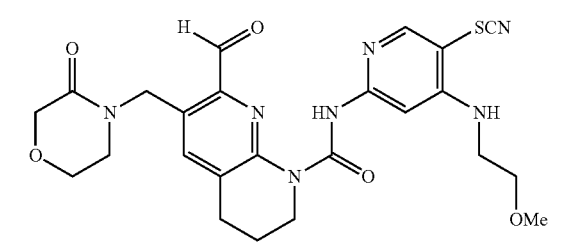
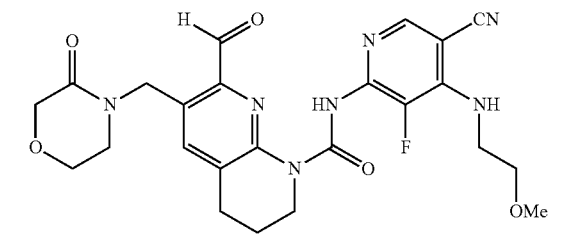
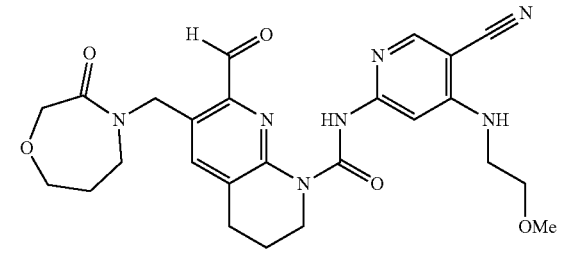
18
-continued
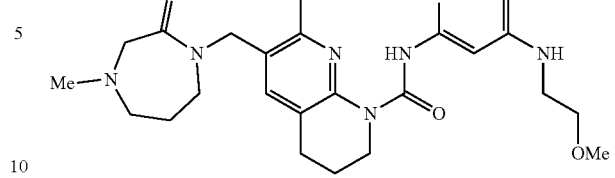
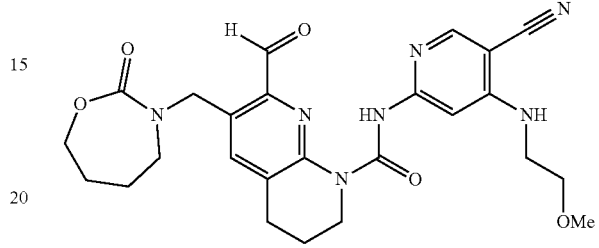
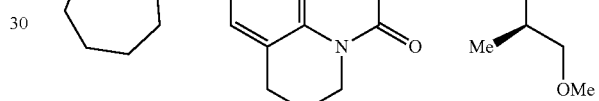
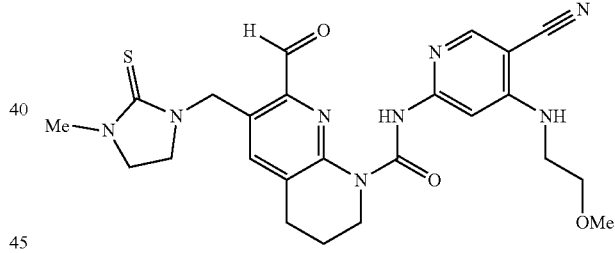
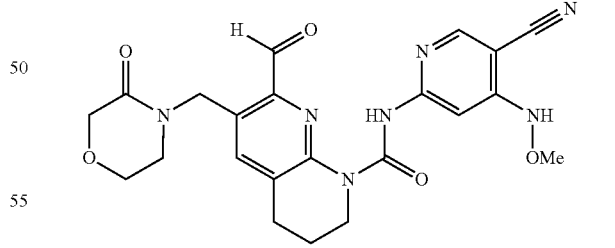
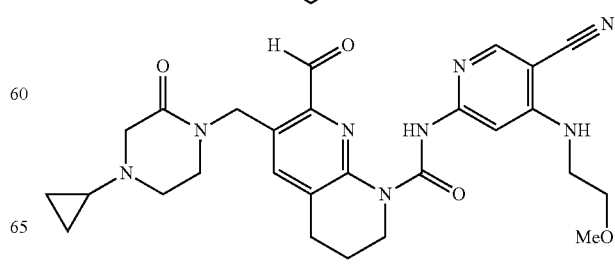

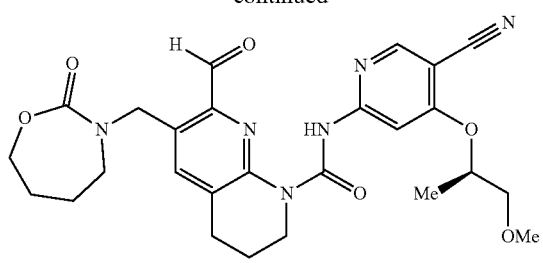

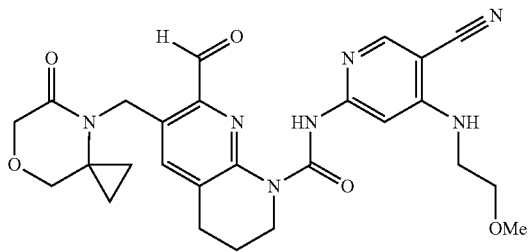

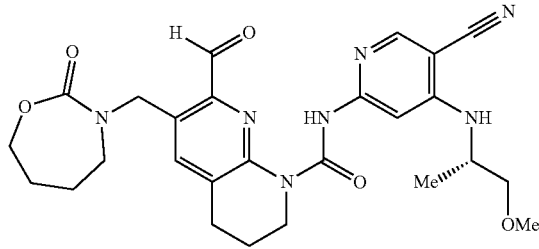

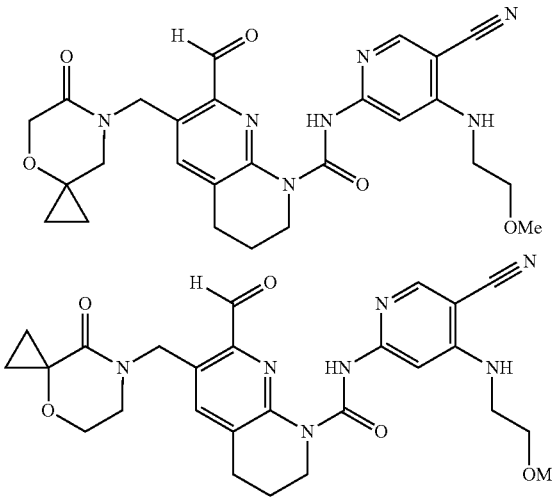

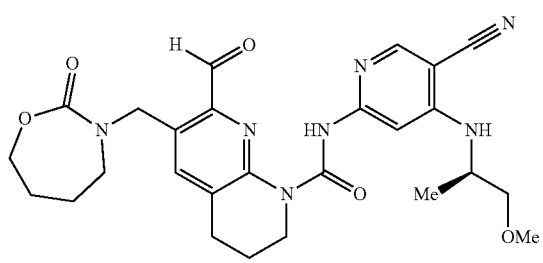

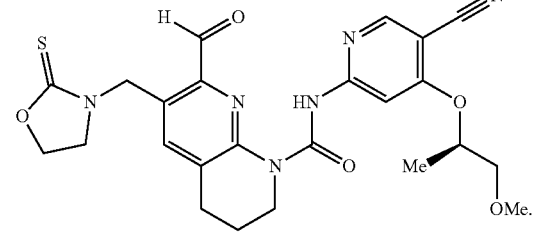

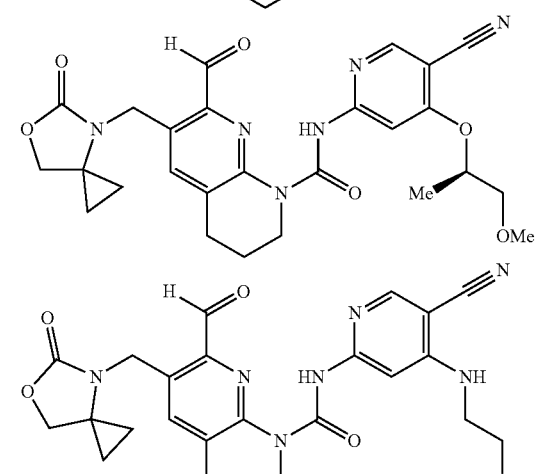

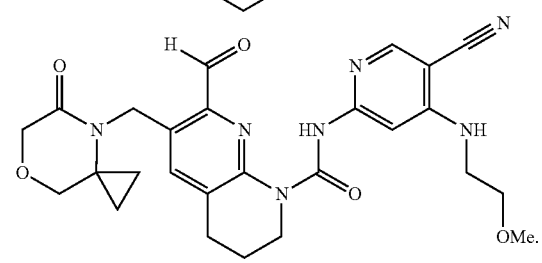

In a further preferred embodiment, in the compound of formula (III), the stereoisomer or the pharmaceutically acceptable salt thereof, R is selected from the group consisting of hydrogen and fluorine; $R_2$ is selected from the group consisting of cyano and thiocyano;

$B_2$ is selected from the group consisting of methyl, ethyl, methoxy, ethoxy, methoxyethyl, ethoxymethyl and ethoxyethyl;

$R_{17}$ is selected from the group consisting of methyl, methoxy, ethoxy, isopropoxy, cyclopropyl, cyclobutyl, cyclopentyl, furanyl, thienyl, pyrrolyl, imidazolyl, tetrahydrofuranyl, tetrahydrothienyl, tetrahydropyrrolyl, tetrahydroimidazolyl, piperazinyl and morpholinyl;

or $R_3$ and $R_4$, $R_5$ and $R_6$, $R_7$ and $R_8$ together with the carbon atom to which they are directly attached form a cyclopropyl or cyclobutyl.

In the most preferred embodiment, the compound of formula (I), the stereoisomer or the pharmaceutically acceptable salt thereof is selected from the group consisting of:

In a further preferred embodiment, in the compound of formula (I), the stereoisomer or the pharmaceutically acceptable salt thereof, R is selected from the group consisting of hydrogen and fluorine;

$R_1$ is selected from the group consisting of hydrogen, deuterium, furanyl, thienyl, pyrrolyl, pyrazolyl, imidazolyl, azetidinyl, tetrahydrofuranyl, tetrahydrothienyl, tetrahydropyrrolyl, tetrahydropyrazolyl and tetrahydroimidazolyl;

optionally substituted by one or more groups selected from the group consisting of halogen, hydroxy, alkyl, haloC$_{1-8}$ alkyl, C$_{3-8}$ cycloalkyl, 3-8 membered heterocyclyl, 3-8 membered heterocyclyloxy, 3-8 membered heterocyclylthio, —C$_{0-8}$—S(O)$_r$R$_9$, —C$_{0-8}$—O—R$_{10}$, —C$_{0-8}$—C(O)OR$_{10}$, —C$_{0-8}$—C(O)R$_{11}$, —C$_{0-8}$—O—C(O)R$_{11}$, —C$_{0-8}$—NR$_{12}$R$_{13}$, —C$_{0-8}$—C(O)NR$_{12}$R$_{13}$, —N(R$_{12}$)—C(O)R$_{11}$ and —N(R$_{12}$)—C(O)OR$_{10}$; and R$_2$ is cyano.

In the most preferred embodiment, the compound of formula (I), the stereoisomer or the pharmaceutically acceptable salt thereof is selected from the group consisting of:

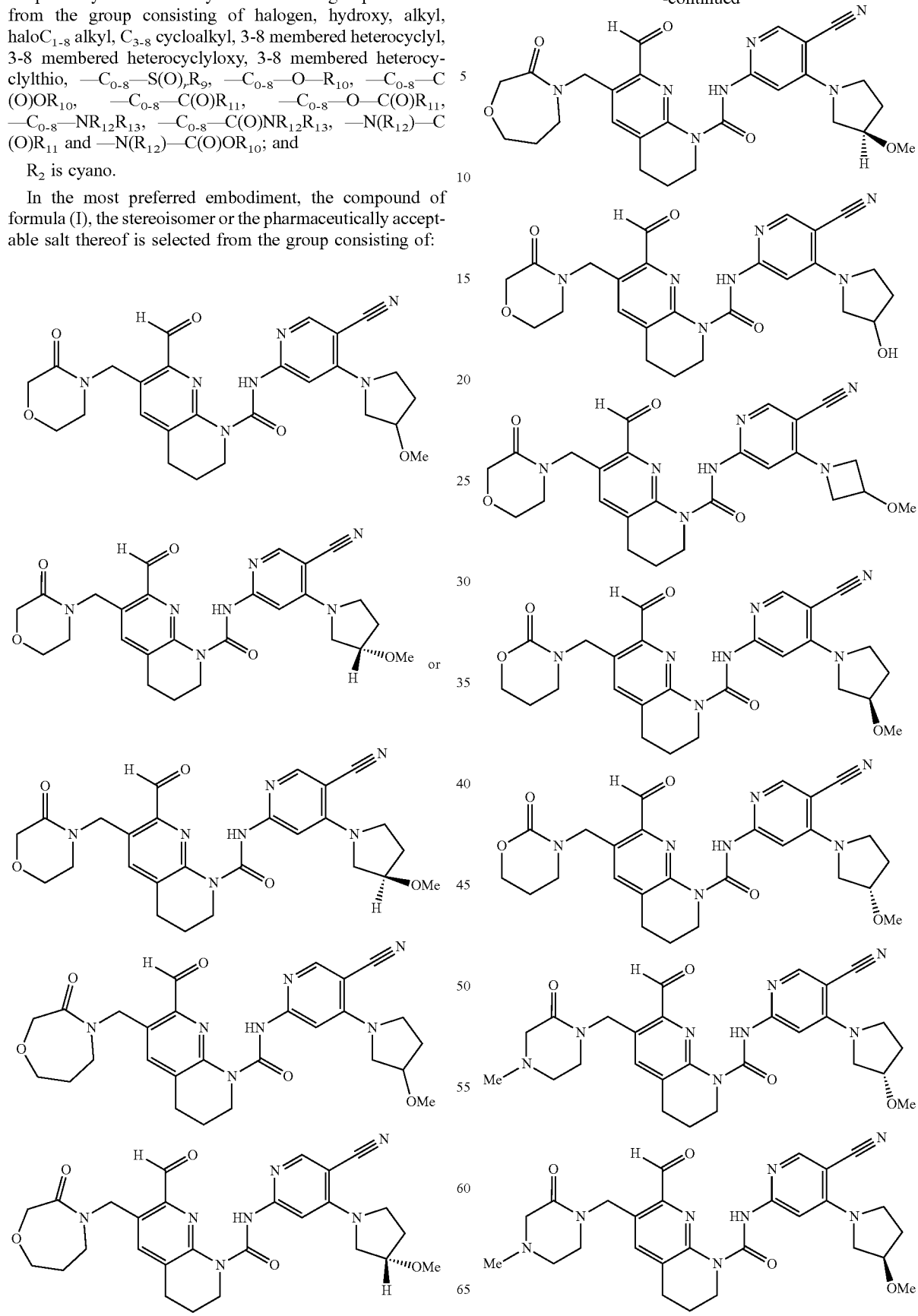

-continued

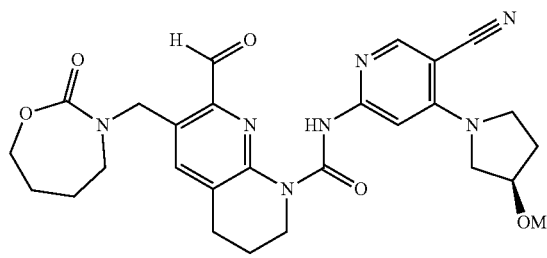

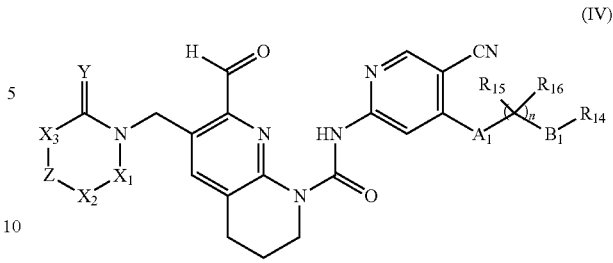

wherein:

Z, Y, A$_1$, B$_1$, X$_1$-X$_3$, R$_{14}$-R$_{16}$ and n are as defined in the compound of formula (II).

In a preferred embodiment of the present invention, the compound of formula (I), the stereoisomer or the pharmaceutically acceptable salt thereof is a compound of formula (V):

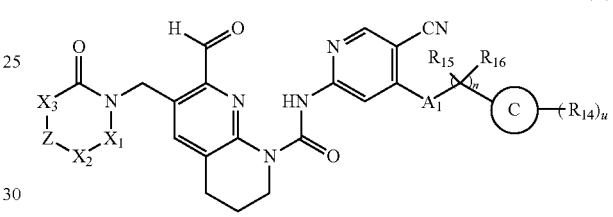

wherein:

ring C is selected from the group consisting of C$_{3-8}$ cycloalkyl, 3-8 membered heterocyclyl, C$_{5-10}$ aryl and 5-10 membered heteroaryl;

u is 0, 1, 2, 3, 4 or 5; and

Z, A$_1$, X$_1$-X$_3$, R$_{14}$-R$_{16}$ and n are as defined in the compound of formula (II).

In a preferred embodiment of the present invention, the compound of formula (I), the stereoisomer or the pharmaceutically acceptable salt thereof is a compound of formula (VI):

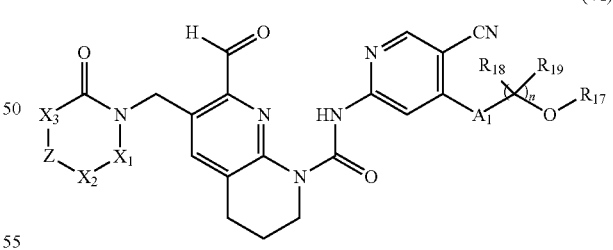

wherein:

A$_1$ is selected from the group consisting of a bond, NX$_4$, oxygen and sulfur;

X$_1$ is —(CR$_3$R$_4$)m$_1$—; X$_2$ is —(CR$_5$R$_6$)m$_2$—; X$_3$ is —(CR$_7$R$_8$)m$_3$—;

R$_3$, R$_4$, R$_5$, R$_6$, R$_7$ and R$_8$ are each independently selected from the group consisting of hydrogen, deuterium, halogen, hydroxy, carboxy, amino, C$_{1-8}$ alkyl, haloC$_{1-8}$ alkyl, C$_{3-8}$ cycloalkyl, C$_{1-8}$ alkoxy and haloC$_{1-8}$ alkoxy, wherein the C$_{1-8}$ alkyl, haloC$_{1-8}$ alkyl, C$_{3-8}$ cycloalkyl, C$_{1-8}$ alkoxy and haloC$_{1-8}$ alkoxy are each optionally substituted by one or In a preferred embodiment of the present invention, the compound of formula (I), the stereoisomer or the pharmaceutically acceptable salt thereof is a compound of formula (IV):

more groups selected from the group consisting of halogen, hydroxy, carboxy, amino, $C_{1-8}$ alkyl, halo$C_{1-8}$ alkyl, $C_{3-8}$ cycloalkyl, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$;

or $R_3$ and $R_4$, $R_5$ and $R_6$, $R_7$ and $R_8$ together with the carbon atom to which they are directly attached form a cycloalkyl or heterocyclyl, wherein the cycloalkyl or heterocyclyl is optionally substituted by one or more groups selected from the group consisting of $C_{1-8}$ alkyl, halo$C_{1-8}$ alkyl, halogen, hydroxy, $C_{1-8}$ alkoxy and hydroxy$C_{1-8}$ alkyl; and Z, $m_1$-$m_3$, $R_{17}$-$R_{19}$ and n are as defined in the compound of formula (III).

In a preferred embodiment of the present invention, the compound of formula (I), the stereoisomer or the pharmaceutically acceptable salt thereof is a compound of formula (VII):

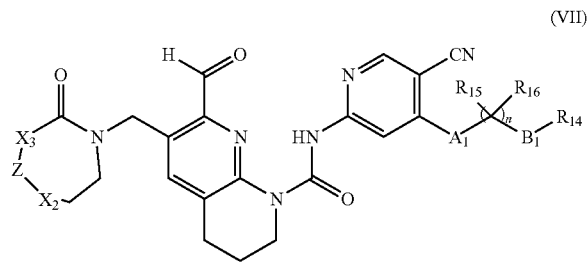

(VII)

wherein:

Z, $A_1$, $B_1$, $X_2$, $X_3$, $R_{14}$-$R_{16}$ and n are as defined in the compound of formula (II).

In a preferred embodiment of the present application, the compound of formula (I), the stereoisomer or the pharmaceutically acceptable salt thereof is a compound of formula (VIII):

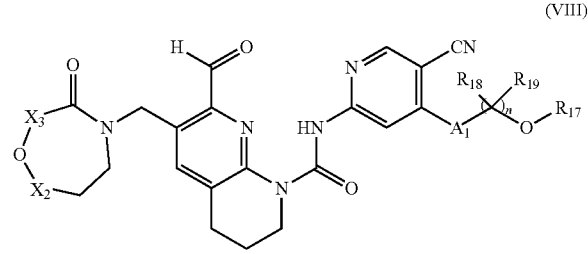

(VIII)

wherein:

$A_1$ is selected from the group consisting of a bond, NX$_4$, oxygen and sulfur;

Z, $X_2$, $X_3$, $R_{17}$-$R_{19}$ and n are as defined in the compound of formula (III).

In a preferred embodiment of the present invention, the compound of formula (I), the stereoisomer or the pharmaceutically acceptable salt thereof is a compound of formula (IX):

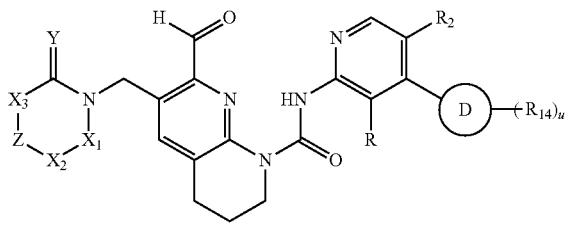

(IX)

wherein:

ring D is selected from the group consisting of $C_{3-8}$ cycloalkyl, 3-8 membered heterocyclyl, $C_{5-10}$ aryl and 5-10 membered heteroaryl;

R is selected from the group consisting of hydrogen and fluorine;

$R_2$ is cyano;

u is 0, 1, 2, 3, 4 or 5; and

Z, Y, $X_1$-$X_3$, $R_{14}$ are as defined in the compound of formula (II).

In a preferred embodiment of the present invention, in the compound of formula (I), the stereoisomer or the pharmaceutically acceptable salt thereof, $R_{14}$ is selected from the group consisting of hydrogen, $C_{1-8}$ alkyl, $C_{1-8}$ alkoxy, halo$C_{1-8}$ alkyl, $C_{3-8}$ cycloalkyl, 3-8 membered heterocyclyl, 3-8 membered heterocyclyloxy, 3-8 membered heterocyclylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$.

In a preferred embodiment of the present invention, in the compound of formula (I), the stereoisomer or the pharmaceutically acceptable salt thereof, $R_{17}$ is selected from the group consisting of hydrogen, $C_{1-8}$ alkyl, $C_{1-8}$ alkoxy, halo$C_{1-8}$ alkyl, $C_{3-8}$ cycloalkyl, 3-8 membered heterocyclyl, 3-8 membered heterocyclyloxy and 3-8 membered heterocyclylthio, wherein the $C_{1-8}$ alkyl, $C_{1-8}$ alkoxy, halo$C_{1-8}$ alkyl, $C_{3-8}$ cycloalkyl, 3-8 membered heterocyclyl, 3-8 membered heterocyclyloxy and 3-8 membered heterocyclylthio are each optionally substituted by $C_{1-8}$ alkyl, $C_{1-8}$ alkoxy, halo$C_{1-8}$ alkyl, $C_{3-8}$ cycloalkyl or 3-8 membered heterocyclyl.

In the second aspect, the present invention provides a process for preparing the aforementioned compound of formula (I), the stereoisomer or the pharmaceutically acceptable salt thereof, comprising the steps of:

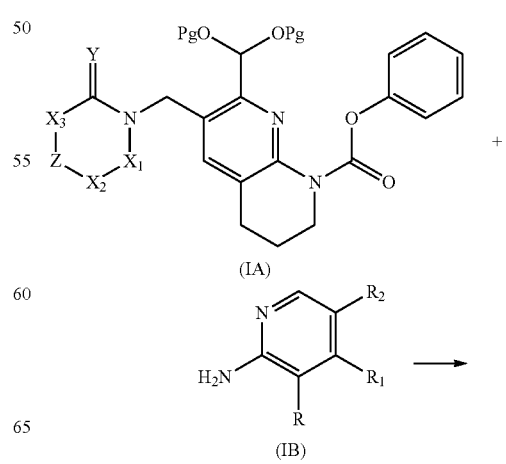

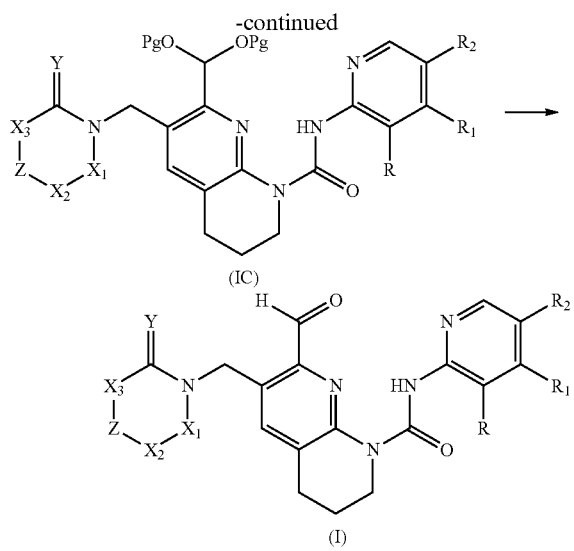

wherein: $X_1$, $X_2$, $X_3$, R, $R_1$, $R_2$, $R_3$, $R_4$, $R_5$, $R_6$, $R_7$, $R_8$, $R_9$, $R_{10}$, $R_{11}$, $R_{12}$, $R_{13}$, r, Z, $m_1$, $m_2$, $m_3$ and Y are as defined in the compound of formula (I); and Pg is a hydroxy protecting group, preferably $C_{1-8}$ alkyl or benzyl.

In the third aspect, the present invention provides a pharmaceutical composition comprising a therapeutically effective amount of the aforementioned compound of formula (I), the stereoisomer or the pharmaceutically acceptable salt thereof and a pharmaceutically acceptable carrier.

In the fourth aspect, the present invention relates to a use of the aforementioned compound of formula (I), the stereoisomer or the pharmaceutically acceptable salt thereof, or the aforementioned pharmaceutical composition in the preparation of a FGFR4 inhibitor medicament.

In the fifth aspect, the present invention relates to a use of the aforementioned compound of formula (I), the stereoisomer or the pharmaceutically acceptable salt thereof, or the aforementioned pharmaceutical composition in the preparation of a medicament for treating cancer. Preferably, the cancer is selected from the group consisting of liver cancer, gastric cancer, prostate cancer, skin cancer, ovarian cancer, lung cancer, breast cancer, colon cancer, glioma and rhabdomyosarcoma.

The present invention also relates to a method for treating and/or preventing diseases related to FGFR4 inhibitors, comprising administering to a patient a therapeutically effective amount of the compound of formula (I), the stereoisomer or the pharmaceutically acceptable salt thereof, or a pharmaceutical compsition comprsing the same.

In another aspect, the present invention relates to a method for treating cancer, comprising administering to a patient a therapeutically effective amount of the compound of formula (I) of the present application, the stereoisomer or the pharmaceutically acceptable salt thereof. The method exhibits outstanding efficacy and fewer side effects, and the cancer is selected from the group consisting of liver cancer, gastric cancer, prostate cancer, skin cancer, ovarian cancer, lung cancer, breast cancer, colon cancer, glioma and rhabdomyosarcoma.

DETAILED DESCRIPTION OF THE INVENTION

Detailed description: unless otherwise stated, the following terms which are used in the description and the claims have the following meanings.

"$C_{1-8}$ alkyl" refers to a straight chain or branched chain alkyl group having 1 to 8 carbon atoms, for example, methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl and various branched chain isomers thereof and the like, preferably, methyl, ethyl or propyl. "Cycloalkyl" refers to a saturated or partially unsaturated monocyclic or polycyclic hydrocarbon group, "$C_{3-8}$ cycloalkyl" refers to a cycloalkyl group having 3 to 8 carbon atoms, for example:

Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, preferably cyclopropyl, cyclobutyl, cyclopentyl or cyclopentenyl, and more preferably cyclopropyl.

Polycyclic cycloalkyl includes a cycloalkyl having a spiro ring, fused ring and bridged ring. "Spiro cycloalkyl" refers to a polycyclic group with rings connected through one common carbon atom (called a spiro atom), wherein these rings can contain one or more double bonds, but none of the rings has a completely conjugated π electronic system. According to the number of the spiro atoms shared between the rings, spiro cycloalkyl can be divided into mono-spiro cycloalkyl, di-spiro cycloalkyl or poly-spiro cycloalkyl. Non-limiting examples of spiro cycloalkyl include:

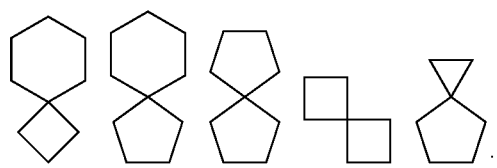

"Fused cycloalkyl" refers to an all-carbon polycyclic group in which each ring in the system shares an adjacent pair of carbon atoms with another ring, wherein one or more rings can contain one or more double bonds, but none of the rings has a completely conjugated π electronic system. According to the number of membered rings, fused-cycloalkyl can be divided into bicyclic, tricyclic, tetracyclic or polycyclic fused cycloalkyl. Non-limiting examples of fused cycloalkyl include:

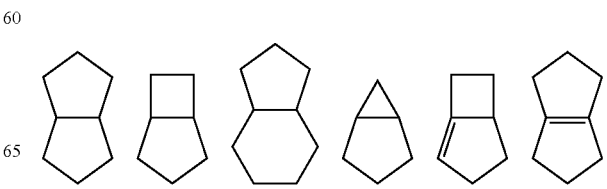

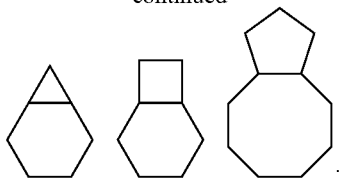

"Bridged cycloalkyl" refers to an all-carbon polycyclic group in which any two rings in the system share two disconnected carbon atoms, wherein these rings can contain one or more double bonds, but none of the rings has a completely conjugated π electronic system. According to the number of membered rings, bridged cycloalkyl can be divided into bicyclic, tricyclic, tetracyclic or polycyclic bridged cycloalkyl. Non-limiting examples of bridged cycloalkvl include:

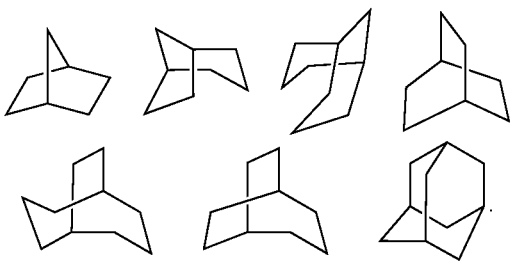

The cycloalkyl ring can be fused to the ring of aryl, heteroaryl or heterocyclyl, wherein the ring connected with the parent structure is the cycloalkyl. Non-limiting examples include indanyl, tetrahydronaphthyl, benzocycloheptylalkyl and the like.

The cycloalkyl can be optionally substituted or unsubstituted. When the cycloalkyl is substituted, the substituent is preferably one or more groups independently selected from the group consisting of halogen, hydroxy, thiol, cyano, nitro, oxo, azido, $C_{1-8}$ alkyl, $C_{2-8}$ alkenyl, $C_{2-8}$ alkynyl, $C_{3-8}$ cycloalkyl, 3-8 membered heterocyclyl, 3-8 membered heterocyclyloxy, 3-8 membered heterocyclylthio, $C_{5-10}$ aryl, $C_{5-10}$ aryloxy, $C_{5-10}$ arylthio, 5-10 membered heteroaryl, 5-10 membered heteroaryloxy, 5-10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$.

"Heterocyclyl" refers to a saturated or partially unsaturated monocyclic or polycyclic hydrocarbon group, wherein one or more ring atoms are heteroatoms selected from the group consisting of nitrogen, oxygen and S(O)$_r$ (wherein r is an integer of 0, 1, and 2), but the cyclic part does not include —O—O—, —O—S— or —S—S—, and the remaining ring atoms are carbon. "5-10 membered heterocyclyl" refers to a heterocyclyl group having 5 to 10 ring atoms, "3-8 membered heterocyclyl" refers to a heterocyclyl group having 3 to 8 ring atoms.

Non-limiting examples of monocyclic heterocyclyl include pyrrolidinyl, piperidinyl, piperazinyl, morpholinyl, thiomorpholinyl, oxazolidinyl, tetrahydrothienyl, oxoazepanyl, homopiperazinyl and the like, preferably oxoazepanyl, pyrrolidinyl, morphinyl, oxazolidinone, oxazolidinethione and piperazinyl.

Polycyclic heterocyclyl includes a heterocyclyl having a spiro ring, fused ring and bridged ring. "Spiro heterocyclyl" refers to a polycyclic heterocyclyl group with rings connected through one common atom (called a spiro atom), wherein one or more ring atoms are heteroatoms selected from the group consisting of nitrogen, oxygen and S(O)$_r$ (wherein r is an integer of 0, 1, and 2), and the remaining ring atoms are carbon. These rings can contain one or more double bonds, but none of the rings has a completely conjugated π electronic system. According to the number of the spiro atoms shared between the rings, spiro cycloalkyl can be divided into mono-spiro heterocyclyl, di-spiro heterocyclyl or poly-spiro heterocyclyl. Non-limiting examples of spiro heterocyclyl include:

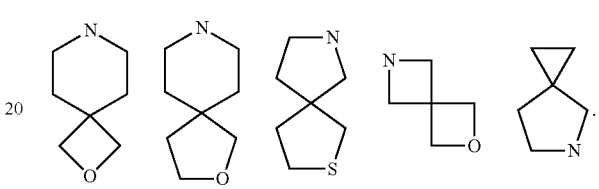

"Fused heterocyclyl" refers to a polycyclic heterocyclyl group in which each ring in the system shares an adjacent pair of atoms with another ring, wherein one or more rings can contain one or more double bonds, but none of the rings has a completely conjugated π electronic system, and wherein one or more ring atoms are heteroatoms selected from the group consisting of nitrogen, oxygen and S(O)$_r$ (wherein r is an integer of 0, 1, and 2), and the remaining ring atoms are carbon. According to the number of membered rings, fused heterocyclyl can be divided into bicyclic, tricyclic, tetracyclic or polycyclic fused heterocyclyl. Non-limiting examples of fused heterocyclyl include:

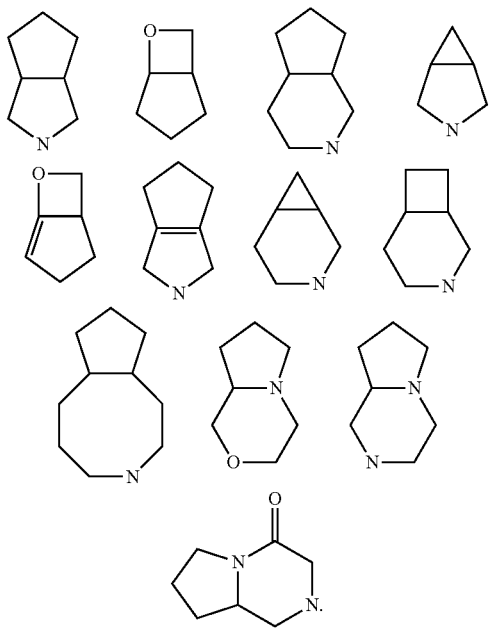

"Bridged heterocyclyl" refers to a polycyclic heterocyclic group in which any two rings in the system share two disconnected atoms, wherein the rings can contain one or more double bonds, but none of the rings has a completely conjugated π electronic system, and one or more ring atoms are heteroatoms selected from the group consisting of nitrogen, oxygen and S(O)$_r$ (wherein r is an integer of 0, 1, and 2), and the remaining ring atoms are carbon. According to the number of membered rings, bridged heterocyclyl can be divided into bicyclic, tricyclic, tetracyclic or polycyclic bridged heterocyclyl. Non-limiting examples of bridged heterocyclyl include:

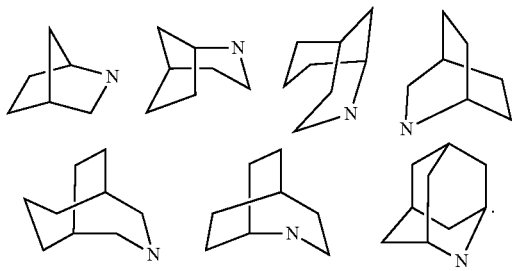

The heterocyclyl ring can be fused to the ring of aryl, heteroaryl or cycloalkyl, wherein the ring connected with the parent structure is the heterocyclyl. Non-limiting examples include:

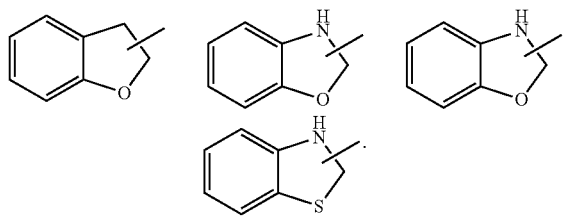

The heterocyclyl can be optionally substituted or unsubstituted. When the heterocyclyl is substituted, the substituent is preferably one or more groups independently selected from the group consisting of halogen, hydroxy, thiol, cyano, nitro, oxo, azido, $C_{1-8}$ alkyl, $C_{2-8}$ alkenyl, $C_{2-8}$ alkynyl, $C_{3-8}$ cycloalkyl, 3-8 membered heterocyclyl, 3-8 membered heterocyclyloxy, 3-8 membered heterocyclylthio, $C_{5-10}$ aryl, $C_{5-10}$ aryloxy, $C_{5-10}$ arylthio, 5-10 membered heteroaryl, 5-10 membered heteroaryloxy, 5-10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$.

"Aryl" refers to an all-carbon monocycle or fused polycycle (i. e., a ring in the system shares an adjacent pair of carbon atoms with another ring) with a conjugated π electronic system. "$C_{5-10}$ aryl" refers to an all-carbon aryl group having 5 to 10 carbon atoms, "5 to 10-membered aryl" refers to an all-carbon aryl group having 5 to 10 carbon atoms, for example, phenyl and naphthyl. The aryl ring can be fused to the ring of heteroaryl, heterocyclyl or cycloalkyl, wherein the ring connected with the parent structure is aryl. Non-limiting examples include:

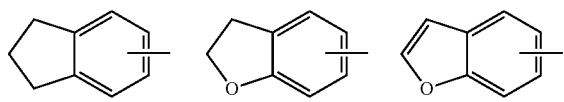

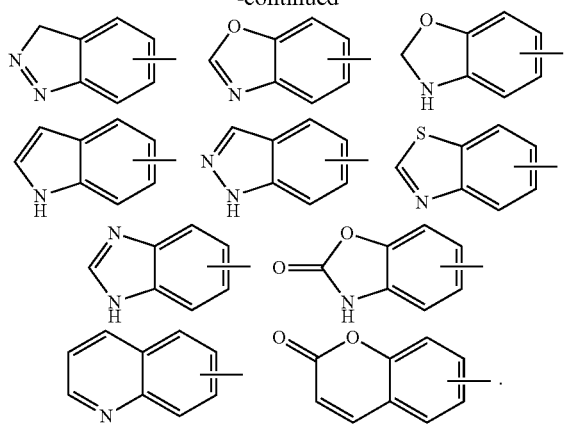

The aryl can be substituted or unsubstituted. When the alkyl is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3-8 membered heterocyclyl, 3-8 membered heterocyclyloxy, 3-8 membered heterocyclylthio, $C_{5-10}$ aryl, $C_{5-10}$ aryloxy, $C_{5-10}$ arylthio, 5-10 membered heteroaryl, 5-10 membered heteroaryloxy, 5-10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$.

"Heteroaryl" refers to a heteroaromatic system having 1 to 4 heteroatoms, wherein the heteroatoms include nitrogen, oxygen and S(O)r (wherein r is an integer of 0, 1, and 2). 5-7 membered heteroaryl refers to a heteroaromatic system having 5 to 7 ring atoms, 5-10 membered heteroaryl refers to a heteroaromatic system having 5 to 10 ring atoms, for example, furanyl, thienyl, pyridyl, pyrrolyl, N-alkyl pyrrolyl, pyrimidinyl, pyrazinyl, imidazolyl, tetrazolyl and the like, preferably pyridyl. The heteroaryl ring can be fused to the ring of aryl, heterocyclyl or cycloalkyl, wherein the ring connected with the parent structure is heteroaryl. Non-limiting examples include:

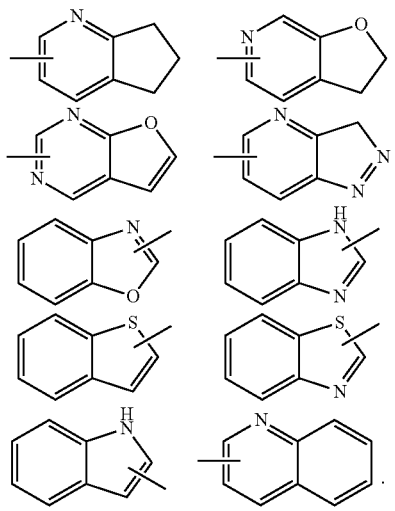

The heteroaryl can be optionally substituted or unsubstituted. When the heteroaryl is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3-8 membered heterocyclyl, 3-8 membered heterocyclyloxy, 3-8 membered heterocyclylthio, $C_{5-10}$ aryl, $C_{5-10}$ aryloxy, $C_{5-10}$ arylthio, 5-10 membered heteroaryl, 5-10 membered heteroaryloxy, 5-10 membered heteroarylthio, —$C_{0-8}$—S(O)$_r$$R_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —N($R_{12}$)—C(O)$R_{11}$ and —N($R_{12}$)—C(O)O$R_{10}$.

"Alkenyl" refers to an alkyl group as defined above that has at least two carbon atoms and at least one carbon-carbon double bond. $C_{2-8}$ alkenyl refers to a straight chain or branched chain alkenyl group having 2 to 8 carbon atoms, for example, vinyl, 1-propenyl, 2-propenyl, 1-, 2- or 3-butenyl and the like.

The alkenyl can be substituted or unsubstituted. When the alkenyl is substituted, the substituent is preferably one or more groups independently selected from the group consisting of halogen, hydroxy, thiol, cyano, nitro, azido, C1-8 alkyl, C2-8 alkenyl, C2-8 alkynyl, C3-8 cycloalkyl, 3-8 membered heterocyclyl, 3-8 membered heterocyclyloxy, 3-8 membered heterocyclylthio, $C_{5-10}$ aryl, $C_{5-10}$ aryloxy, $C_{5-10}$ arylthio, 5-10 membered heteroaryl, 5-10 membered heteroaryloxy, 5-10 membered heteroarylthio, —$C_{0-8}$—S(O)$_r$$R_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —N($R_{12}$)—C(O)$R_{11}$ and —N($R_{12}$)—C(O)O$R_{10}$.

"Alkynyl" refers to an alkyl group as defined above that has at least two carbon atoms and at least one carbon-carbon triple bond. $C_{2-8}$ alkynyl refers to a straight chain or branched chain alkynyl group having 2 to 8 carbons, for example, ethynyl, 1-propynyl, 2-propynyl, 1-, 2- or 3-butynyl and the like.

The alkynyl can be substituted or unsubstituted. When the alkynyl is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3-8 membered heterocyclyl, 3-8 membered heterocyclyloxy, 3-8 membered heterocyclylthio, $C_{5-10}$ aryl, $C_{5-10}$ aryloxy, $C_{5-10}$ arylthio, 5-10 membered heteroaryl, 5-10 membered heteroarylthio, —$C_{0-8}$—S(O)$_r$$R_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —N($R_{12}$)—C(O)$R_{11}$ and —N($R_{12}$)—C(O)O$R_{10}$.

"Alkoxy" refers to an —O—(alkyl) group, wherein the alkyl is as defined above. "$C_{1-8}$ alkoxy" refers to an alkoxy having 1 to 8 carbon. Non-limiting examples include methoxy, ethoxy, propoxy, butoxy and the like.

The alkoxy can be optionally substituted or unsubstituted. When the alkoxy is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3-8 membered heterocyclyl, 3-8 membered heterocyclyloxy, 3-8 membered heterocyclylthio, $C_{5-10}$ aryl, $C_{5-10}$ aryloxy, $C_{5-10}$ arylthio, 5-10 membered heteroaryl, 5-10 membered heteroarylthio, —$C_{0-8}$—S(O)$_r$$R_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —N($R_{12}$)—C(O)$R_{11}$ and —N($R_{12}$)—C(O)O$R_{10}$.

"Cycloalkoxy" refers to an —O—(unsubstituted cycloalkyl) group, wherein the cycloalkyl is as defined above. "$C_{3-8}$ cycloalkoxy" refers to a cycloalkoxy group having 3 to 8 carbons. Non-limiting examples include cyclopropoxy, cyclobutyloxy, cyclopentyloxy, cyclohexyloxy and the like.

The cycloalkoxy can be optionally substituted or unsubstituted. When the cycloalkoxy is substituted, the substituent is preferably one or more groups independently selected from the group consisting of halogen, hydroxy, thiol, cyano, nitro, azido, $C_{1-8}$ alkyl, $C_{2-8}$ alkenyl, $C_{2-8}$ alkynyl, $C_{3-8}$ cycloalkyl, 3-8 membered heterocyclyl, 3-8 membered heterocyclyloxy, 3-8 membered heterocyclylthio, $C_{5-10}$ aryl, $C_{5-10}$ aryloxy, $C_{5-10}$ arylthio, 5-10 membered heteroaryl, 5-10 membered heteroaryloxy, 5-10 membered heteroarylthio, —$C_{0-8}$—S(O)$_r$$R_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —N($R_{12}$)—C(O)$R_{11}$ and —N($R_{12}$)—C(O)O$R_{10}$. "halo$C_{1-8}$ alkyl" refers to a $C_{1-8}$ alkyl group, wherein hydrogen(s) in the alkyl is substituted by fluorine, chlorine, bromine and/or iodine atom(s), for example, difluoromethyl, dichloromethyl, dibromomethyl, trifluoromethyl, trichloromethyl, tribromomethyl and the like.

"halo$C_{1-8}$ alkoxy" refers to a $C_{1-8}$ alkoxy group wherein hydrogen(s) in the alkyl is substituted by fluorine, chlorine, bromine and/or iodine atom(s), for example, difluoromethoxy, dichloromethoxy, dibromomethoxy, trifluoromethoxy, trichloromethoxy, tribromomethoxy and the like.

"Halogen" refers to fluorine, chlorine, bromine or iodine.
"THF", refers to tetrahydrofuran.
"EtOAc" refers to ethyl acetate.
"MeOH" refers to methanol.
"DMF" refers to N,N-dimethylformamide.
"DIPEA" refers to diisopropylethylamine.
"TFA" refers to trifluoroacetic acid.
"MeCN" refers to acetonitrile.
"DMA" refers to N,N-dimethylacetamide.
"Et$_2$O" refers to diethyl ether.
"DCE" refers to 1,2 dichloroethane.
"DIPEA" refers to N,N-diisopropylethylamine.
"NBS" refers to N-bromosuccinimide.
"NIS" refers to N-iodosuccinimide.
"Cbz-Cl" refers to benzyl chloroformate.
"Pd$_2$(dba)$_3$" refers to tris (dibenzylideneacetone) dipalladium.
"Dppf" refers to 1,1'-bisdiphenylphosphinoferrocene.
"HATU" refers to 2-(7-oxobenzotriazole)-N,N,N',N'-tetramethyluronium hexafluorophosphate.
"KHMDS" refers to potassium hexamethyldisilazide.
"LiHMDS" refers to lithium bis(trimethylsilyl)amide.
"MeLi" refers to methyl lithium.
"n-BuLi" refers to n-butyl lithium.
"NaBH(OAc)$_3$" refers to sodium triacetoxyborohydride.
"Stereoisomerism" includes three types: geometric isomerism (cis-trans isomerization), optical isomerism, and conformational isomerism.

Different terms such as "X is selected from the group consisting of A, B or C", "X is selected from the group consisting of A, B and C", "X is A, B or C", and "X is A, B and C" express the same meaning, that is, X can be any one or more of A, B, and C.

The hydrogen atom of the present invention can be substituted by its isotope deuterium, and any one of the hydrogen atoms in the compounds of the examples of the present invention can also be substituted by deuterium atom.

"Optional" or "optionally" means that the subsequently described event or the circumstance can, but need not occur, and such a description includes the instances in which the event or the circumstance does or does not occur. For example, "heterocyclyl optionally substituted by alkyl" means that the alkyl group can be, but need not be present, and such a description includes the instances in which the heterocyclyl group is substituted by alkyl and the heterocyclyl group is not substituted by alkyl.

"Substituted" means that one or more hydrogen atoms in the group are each independently substituted by the corresponding number of the substituents. Apparently, the substituents are only positioned at their possible chemical positions, and the possible or impossible substitutions can be determined (through experiments or theory) by those skilled in the art without paying excessive efforts. For example, the combination of amino or hydroxy having free hydrogen and carbon atoms having unsaturated bonds (such as olefinic) can be unstable. "Pharmaceutical composition" refers to a mixture comprising one or more of the compounds described herein or the physiological/pharmaceutical salts or prodrugs thereof and other chemical components, and other components such as physiological/pharmaceutical carriers and excipients. The purpose of a pharmaceutical composition is to facilitate administration of a compound to an organism, which will help absorption of the active ingredient, thereby realizing biological activity.

The following examples serve to illustrate the present invention in detail and completely, but these examples should not be considered as limiting the scope of the present invention, and the present invention is not limited to the examples.

The structures of compounds in the present invention were identified by nuclear magnetic resonance (NMR) and/or liquid chromatography-mass spectrometry (LC-MS). The chemical shift of NMR is given in $10^{-6}$(ppm). NMR was determined by a Bruker AVANCE-400 machine, the solvents for determination are deuterated dimethylsulfoxide (DMSO-d6), deuterated methanol (CD$_3$OD) and deuterated chloroform (CDCl$_3$), and the internal standard is tetramethylsilane (TMS).

Liquid chromatography-mass spectrometry (LC-MS) was determined by an Agilent 1200 Infinity Series mass spectrometer. HPLC was determined on an Agilent 1200DAD high pressure liquid chromatographic instrument (Sunfire C18 150×4.6 mm chromatographic column) and a Waters 2695-2996 high pressure liquid chromatographic instrument (Gimini C18 150×4.6 mm chromatographic column).

For thin-layer silica gel chromatography (TLC), Yantai Huanghai HSGF254 or Qingdao GF254 silica gel plate was used. The dimension of the plates used in TLC was 0.15 mm to 0.2 mm, and the dimension of the plates used in product purification was 0.4 mm to 0.5 mm. Column chromatography generally used Yantai Huanghai 200 to 300 mesh silica gel as carrier.

The starting materials used in the examples of the present invention are known and commercially available, or can be synthesized by adopting or according to known methods in the art.

Unless otherwise stated, all reactions of the present invention are carried out under continuous magnetic stirring in a dry nitrogen or argon atmosphere, the solvent is dry, and the reaction temperature is in degrees Celsius.

Preparation of Intermediate

Intermediate 1: Preparation of 6-amino-4-fluoronicotinonitrile

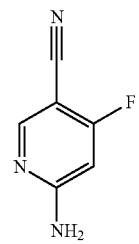

Step 1: Preparation of 4-fluoro-5-iodopyridin-2-amine

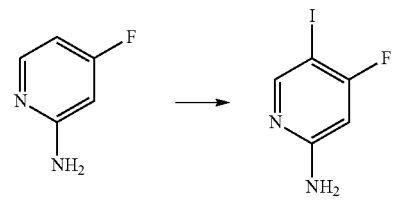 [SMILES: Nc1cc(F)ccn1 ; Nc1cc(F)c(I)cn1]

4-Fluoropyridin-2-amine (9 g, 80 mmol), NIS (19.8 g, 88 mmol) and TFA (3.65 g, 32 mmol) were mixed in MeCN (290 mL), and then the reaction was carried out at room temperature overnight. The reaction solution was diluted with ethyl acetate (300 mL), and washed with saturated aqueous Na$_2$SO$_3$ solution (150 mL×2). The organic phase was washed with saturated brine, dried over anhydrous sodium sulfate and concentrated to obtain the title compound 4-fluoro-5-iodopyridin-2-amine (15.8 g, 83%).

MS m/z (ESI): 238.9 [M+H]$^+$.

Step 2: Preparation of 6-amino-4-fluoronicotinonitrile

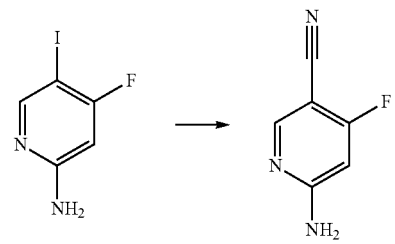 [SMILES: Nc1cc(F)c(I)cn1 ; N#Cc1cnc(N)cc1F]

4-Fluoro-5-iodopyridin-2-amine (15.8 g, 66.4 mmol), Zn(CN)$_2$ (8.2 g, 69.8 mmol) and Zn (0.87 g, 13.3 mmol) were mixed in DMA (55 mL), followed by addition of Pd$_2$(dba)$_3$ (2.4 g, 2.62 mmol) and dppf (7.4 g, 13.35 mmol) in a nitrogen atmosphere. The reaction system was purged 3 times with nitrogen, and then warmed up to 110° C. for 3 hours in the nitrogen atmosphere. Then the reaction solution was cooled to room temperature, and diluted with ethyl acetate (100 mL), followed by addition of saturated aqueous NaHCO₃ solution (200 mL). Two phases were separated, and the aqueous phase was extracted with ethyl acetate (150 mL×3). The organic phases were combined, washed with saturated brine, dried over anhydrous sodium sulfate and concentrated to obtain the title compound 6-amino-4-fluoronicotinonitrile (7.3 g, 80%).

MS m/z (ESI): 138.1 [M+H]⁺.

Intermediate 2: Preparation of 6-amino-4-((2-methoxyethyl)amino)nicotinonitrile

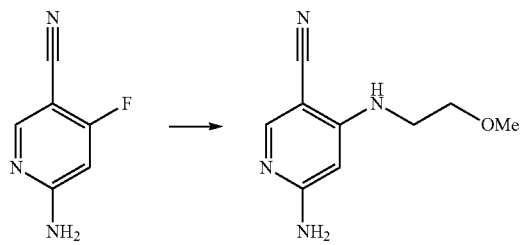 [SMILES: N#Cc1cnc(N)cc1F ; COCCNc1cc(N)ncc1C#N]

6-Amino-4-fluoronicotinonitrile (4.11 g, 30 mmol), 2-methoxyethane-1-amine (4.5 g, 60 mmol), and DIPEA (1.16 g, 90 mmol) were mixed in DMA (120 mL). The mixture was stirred at 60° C. overnight. Then the reaction solution was concentrated. The resulting residue was dissolved in dichloromethane (100 mL), followed by addition of saturated aqueous NaHCO₃ solution (100 mL) to separate phases. Two phases were separated, and the organic phase was washed with saturated aqueous NaCl solution (50 mL×2), dried over anhydrous sodium sulfate and concentrated. The resulting residue was subjected to column chromatography to obtain the title compound 6-amino-4-((2-methoxyethyl)amino)nicotinonitrile (3.84 g, 67%).

¹H NMR (400 MHz, DMSO) δ 7.93 (s, 1H), 6.39 (s, 2H), 6.14 (t, J=5.6 Hz, 1H), 5.62 (s, 1H), 3.47 (t, J=6.0 Hz, 2H), 3.29-3.22 (m, 5H);

MS m/z (ESI): 193.1 [M+H]⁺.

Intermediate 3: Preparation of 6-amino-4-((2-(pyrrolidin-1-yl)ethyl)amino)nicotinonitrile

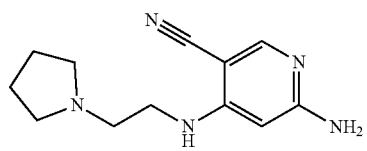 [SMILES: N#Cc1cnc(N)cc1NCCN1CCCC1]

6-Amino-4-((2-(pyrrolidin-1-yl)ethyl)amino)nicotinonitrile was prepared in accordance with the method of Intermediate 2.

MS m/z (ESI): 232.1 [M+H]⁺.

Intermediate 4: Preparation of 6-amino-4-((2-(cyclopentyloxy)ethyl)amino)nicotinonitrile

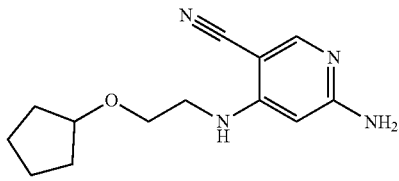 [SMILES: N#Cc1cnc(N)cc1NCCOC1CCCC1]

6-Amino-4-((2-(cyclopentyloxy)ethyl)amino)nicotinonitrile was prepared in accordance with the method of Intermediate 2.

MS m/z (ESI): 247.1 [M+H]⁺.

Intermediate 5: Preparation of 6-amino-4-(3-methoxypyrrolidin-1-yl)nicotinonitrile

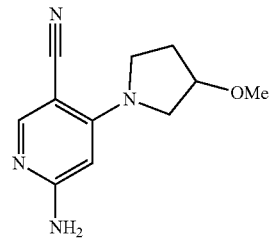

6-Amino-4-(3-methoxypyrrolidin-1-yl)nicotinonitrile was prepared in accordance with the method of Intermediate 2.

MS m/z (ESI): 219.1 [M+H]⁺.

Intermediate 6: Preparation of 6-amino-4-(((trans)-2-methoxycyclopentyl)amino)nicotinonitrile

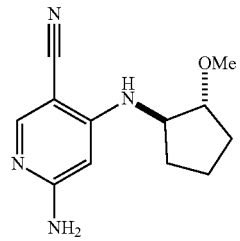

Step 1: Preparation of benzyl ((trans)-2-hydroxycyclopentyl)carbamate

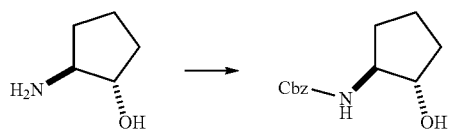 [SMILES: N[C@H]1CCC[C@@H]1O ; O=C(N[C@H]1CCC[C@@H]1O)OCc1ccccc1]

(Trans)-2-aminocyclopentane-1-ol (1 g, 10 mmol) and Na₂CO₃ (3.4 g, 30 mmol) were mixed in water (20 mL), followed by dropwise addition of Cbz-Cl (3.4 g, 20 mmol) at 0° C. The reaction solution was warmed up to room temperature naturally and stirred overnight, then diluted with water (30 mL), and extracted with ethyl acetate (50 mL×2). The organic phase was washed with saturated brine, dried over anhydrous sodium sulfate, and concentrated. The resulting residue was subjected to column chromatography to obtain the title compound benzyl ((trans)-2-hydroxycyclopentyl)carbamate (1.32 g, 56%).

MS m/z (ESI): 236.2 [M+H]$^+$.

Step 2: Preparation of benzyl ((trans)-2-methoxycyclopentyl)carbamate

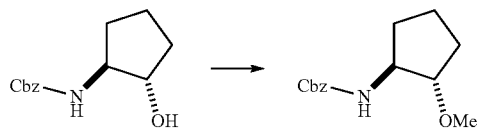 [SMILES: O=C(N[C@H]1CCC[C@@H]1O)OCc1ccccc1 ; CO[C@H]1CCC[C@@H]1NC(=O)OCc1ccccc1]

Benzyl ((trans)-2-hydroxycyclopentyl)carbamate (470 mg, 2 mmol) was dissolved in THF (20 mL), followed by addition of NaH (96 mg, 2.4 mmol) at 0° C. After the reaction was carried out for 30 min, CH$_3$I (312 mg, 30 mmol) was added dropwise. The reaction solution was warmed up to room temperature naturally and stirred overnight, then added with saturated aqueous NH$_4$Cl solution (50 mL), and extracted with ethyl acetate (50 mL×2). The organic phase was washed with saturated brine, dried over anhydrous sodium sulfate and concentrated. The resulting residue was subjected to column chromatography to obtain the title compound benzyl ((trans)-2-methoxycyclopentyl) carbamate (300 mg, 60%).

MS m/z (ESI): 250.1 [M+H]$^+$.

Step 3: Preparation of (trans)-2-methoxycyclopentan-1-amine

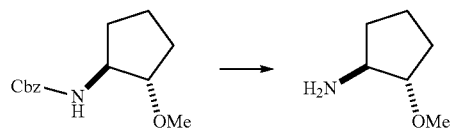 [SMILES: CO[C@H]1CCC[C@@H]1NC(=O)OCc1ccccc1 ; CO[C@H]1CCC[C@@H]1N]

Benzyl ((trans)-2-methoxycyclopentyl)carbamate (300 mg, 1.2 mmol) was dissolved in methanol (30 mL), followed by addition of 10% Pd/C (60 mg). The reaction was carried out in a hydrogen atmosphere for 2 hours. Then the reaction solution was filtered and concentrated to obtain the title compound (trans)-2-methoxycyclopentan-1-amine (70 mg, 50%).

MS m/z (ESI): 116.2 [M+H]$^+$.

Step 4: Preparation of 6-amino-4-(((trans)-2-methoxycyclopentyl)amino)nicotinonitrile

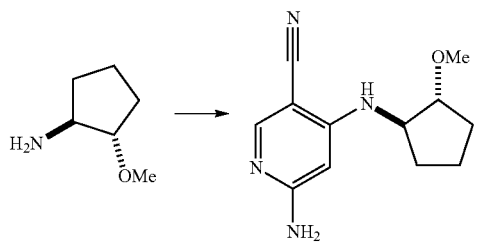

6-Amino-4-(((trans)-2-methoxycyclopentyl)amino)nicotinonitrile was prepared in accordance with the method of Intermediate 2.

MS m/z (ESI): 233.2 [M+H]$^+$.

Intermediate 7: Preparation of 6-amino-4-((2-methyltetrahydrofuran-3-yl)thio)nicotinonitrile

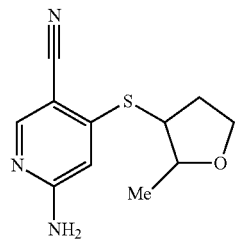 [SMILES: CC1OCCC1Sc1cc(N)ncc1C#N]

2-Methyltetrahydrofuran-3-thiol (142 mg, 1.2 mmol) was dissolved in THF (5 mL), followed by addition of KHMDS (1.2 mL, 1.2 mmol) in a nitrogen atmosphere. The solution was stirred at room temperature for 30 min, and then a solution of 6-amino-4-fluoronnibronitrile (82.2 mg, 0.6 mmol) in THF (1 mL) was added dropwise. The reaction was carried out at room temperature overnight. The reaction solution was added with saturated aqueous NH$_4$Cl solution (50 mL), and extracted with ethyl acetate (50 mL×2). The organic phase was washed with saturated brine, dried over anhydrous sodium sulfate, and concentrated. The resulting residue was subjected to column chromatography to obtain the title compound 6-amino-4-((2-methyltetrahydrofuran-3-yl)thio)nicotinonitrile (80 mg, 57%).

MS m/z (ESI): 236.1 [M+H]$^+$.

Intermediate 8: Preparation of 6-amino-4-((2-methoxyphenyl)amino)nicotinonitrile

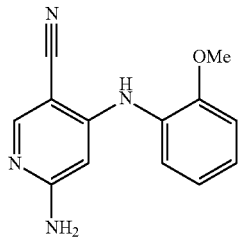

6-Amino-4-((2-methoxyphenyl)amino)nicotinonitrile was prepared in accordance with the method of Intermediate 7.

MS m/z (ESI): 241.1 [M+H]+.

Intermediate 9: Preparation of 6-amino-4-(((1-methoxycyclopropyl)methyl)amino)nicotinonitrile

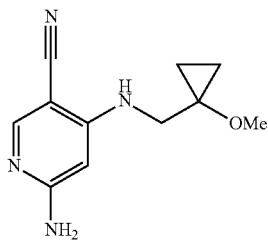 [SMILES: COC1(CNc2cc(N)ncc2C#N)CC1]

Step 1: Preparation of ethyl N-(diphenylmethyl)glycinate

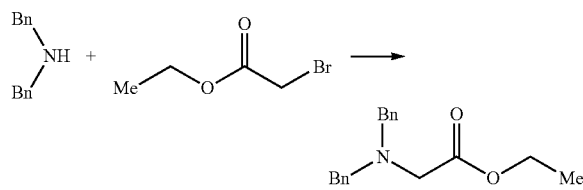

Dibenzylamine (10.0 g, 51 mmol) and ethyl bromide (6.77 g, 41 mmol) were dissolved in ethanol (100 mL). The solution was heated to 70° C. and stirred for 12 hours. The reaction solution was concentrated, then the resulting residue was dissolved in $CH_2Cl_2$, washed with saturated $NH_4Cl$ aqueous solution and saturated brine successively, dried over anhydrous sodium sulfate, and concentrated. The resulting residue was subjected to column chromatography to obtain the title compound ethyl N-(diphenylmethyl)glycinate (6.5 g, 57%).

MS m/z (ESI): 284.2 [M+H]+.

Step 2: Preparation of 1-((diphenylmethylamino)methyl)cyclopropan-1-ol

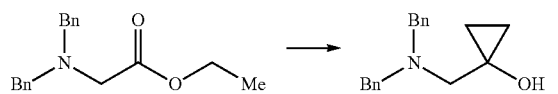 [SMILES: CCOC(=O)CN(Cc1ccccc1)Cc1ccccc1 ; OC1(CN(Cc2ccccc2)Cc2ccccc2)CC1]

Titanium isopropoxide (622 mg, 2.33 mmol) was added to a solution of ethyl N-(phenylmethylene)glycinate (3.0 g, 11 mmol) in diethyl ether (100 mL) at room temperature. Ethylmagnesium bromide (3.0 M $Et_2O$ solution, 10.6 mL, 31.8 mmol) was added dropwise and slowly, and the mixture was stirred for 12 hours at room temperature. After the reaction was cooled to 0° C., hydrochloric acid (2M, 10 mL) was added slowly, and then the reaction was warmed up to room temperature slowly and stirred for 30 minutes. After addition of saturated $NaHCO_3$ aqueous solution (60 mL), the reaction solution was stirred for 10 minutes, extracted twice with $CH_2Cl_2$, and concentrated. The resulting residue was subjected to column chromatography to obtain the title compound 1-((diphenylmethylamino)methyl)cyclopropan-1-ol (1.7 g, 60%).

MS m/z (ESI): 268.2 [M+H]+.

Step 3: Preparation of N,N-dibenzylmethyl-1-(1-methoxycyclopropyl)methyl-amine

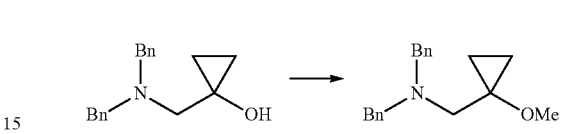

NaH (60% in oil, 179 mg, 4.5 mmol) was added in batches to a solution of 1-((diphenylmethylamino)methyl)cyclopropan-1-ol (1.0 g, 3.7 mmol) in DMF (100 mL) in an ice bath. The mixture was stirred at this temperature for 60 minutes, followed by addition of methyl iodide (584 mg, 4.1 mmol), and then warmed up to room temperature slowly and stirred for 2 hours. After addition of saturated $NH_4Cl$ aqueous solution (10 mL), the reaction solution was concentrated. The resulting residue was dissolved in $CH_2Cl_2$, washed with saturated aqueous $NH_4Cl$ solution and saturated brine successively, dried over anhydrous sodium sulfate, and concentrated. The resulting residue was subjected to column chromatography to obtain the title compound N,N-dibenzylmethyl -1-(1-methoxycycl opropyl)methyl amine (350 mg, 33%).

MS m/z (ESI): 282.2 [M+H]+.

Step 4: Preparation of (1-methoxycyclopropyl)methylamine

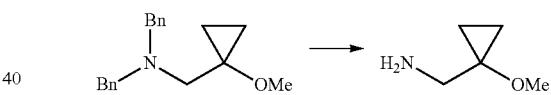

In a nitrogen atmosphere, acetic acid (2 mL) and $Pd(OH)_2$ (60 mg) were added to a solution of N,N-dibenzylmethyl -1-(1-methoxy cy cl opropyl)m ethyl amine (300 mg, 1.07 mmol) in MeOH (10 mL). In a hydrogen atmosphere (50 Psi), the reaction solution was stirred for 12 hours, concentrated and filtered to obtain the title compound (1-methoxycyclopropyl)methylamine which was directly used in the next step.

MS m/z (ESI): 102.1 [M+H]+.

Step 5: Preparation of 6-amino-4-(((1-methoxycyclopropyl)methyl)amino)nicotinonitrile

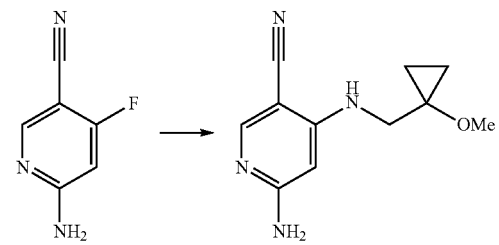 [SMILES: N#Cc1cnc(N)cc1F ; COC1(CNc2cc(N)ncc2C#N)CC1]

6-Amino-4-(((1-methoxycyclopropyl)methyl)amino)
nicotinonitrile was prepared in accordance with the method
of Intermediate 2.

MS m/z (ESI): 219.1 [M+H]⁺.

Intermediate 10: Preparation of 6-amino-4-((2-cyclopropoxyethyl)amino)nicotinonitrile

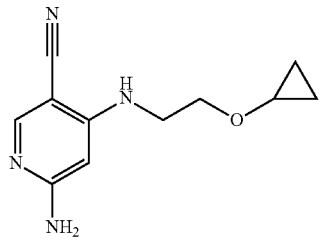 [SMILES: N#Cc1cnc(N)cc1NCCOC1CC1]

6-Amino-4-((2-cyclopropoxyethyl)amino)nicotinonitrile
was prepared in accordance with the method of Intermediate
2.

MS m/z (ESI): 219.1 [M+H]⁺.

Intermediate 11: Preparation of 6-amino-4-((2-(cyclopropylmethoxy)ethyl)amino)nicotinonitrile

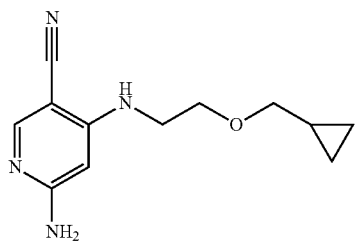 [SMILES: N#Cc1cnc(N)cc1NCCOCC1CC1]

6-Amino-4-((2-(cyclopropylmethoxy)ethyl)amino)nicotinonitrile was prepared in accordance with the method of
Intermediate 2.

MS m/z (ESI): 233.1 [M+H]⁺.

Intermediate 12: Preparation of 6-amino-4-((1-(methoxymethyl)cyclopropyl)amino)nicotinonitrile

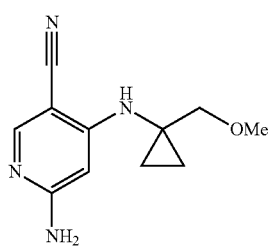 [SMILES: COCC1(Nc2cc(N)ncc2C#N)CC1]

6-Amino-4-((1-(methoxymethyl)cyclopropyl)amino)
nicotinonitrile was prepared in accordance with the method
of Intermediate 2.

MS m/z (ESI): 219.1 [M+H]⁺.

Intermediate 13: Preparation of 6-amino-4-(((cis)-2-methoxycyclopentyl)amino)nicotinonitrile

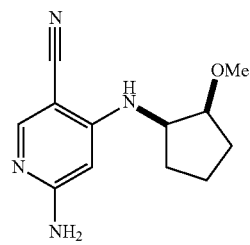

6-Amino-4-(((cis)-2-methoxycyclopentyl)amino)nicotinonitrile was prepared in accordance with the method of
Intermediate 2.

MS m/z (ESI): 233.1 [M+H]⁺.

Intermediate 14: Preparation of

N4-(2-methoxyethyl)-5-thiocyanatopyridine-2,4-diamine

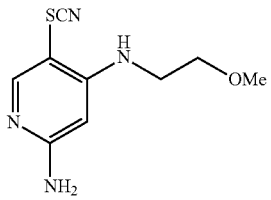

N4-(2-Methoxyethyl)-5-thiocyanatopyridine-2,4-diamine
was prepared in accordance with the method of Intermediate
2.

MS m/z (ESI): 225.1 [M+H]⁺.

Intermediate 15: Preparation of 6-amino-5-fluoro-4-((2-methoxyethyl)amino)nicotinonitrile

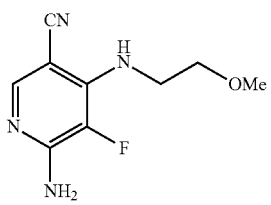

6-Amino-5-fluoro-4-((2-methoxyethyl)amino)nicotinonitrile was prepared in accordance with the method of Intermediate 2.

MS m/z (ESI): 211.1 [M+H]⁺.

Intermediate 16: Preparation of 6-amino-4-((tetrahydrofuran-3-yl)thio)nicotinonitrile

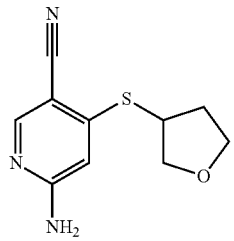 [SMILES: N#Cc1cnc(N)cc1SC1CCOC1]

6-Amino-4-((tetrahydrofuran-3-yl)thio)nicotinonitrile was prepared in accordance with the method of Intermediate 7.

MS m/z (ESI): 222.1 [M+H]⁺.

Intermediate 17: Preparation of 6-amino-4-((2-methoxyethyl)thio)nicotonitrile

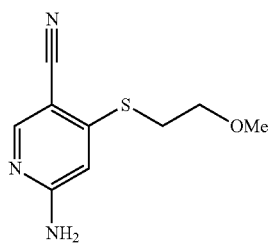 [SMILES: COCCSc1cc(N)ncc1C#N]

6-Amino-4-((2-methoxyethyl)thio)nicotinonitrile was prepared in accordance with the method of Intermediate 7.

MS m/z (ESI): 210.1 [M+H]⁺.

Intermediate 18: Preparation of 6-amino-4-((1-methoxycyclopropyl)methoxy)nicotinonitrile

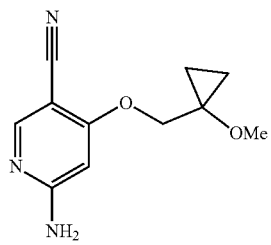

6-Amino-4-((1-methoxycyclopropyl)methoxy)nicotinonitrile was prepared in accordance with the method of Intermediate 7.

MS m/z (ESI): 220.2 [M+H]+.

Intermediate 19: Preparation of 6-amino-4-(((trans)-2-methoxycyclopentyl)oxy)nicotinonitrile

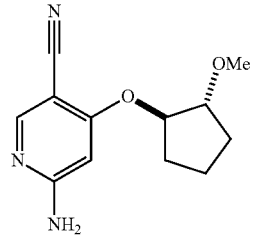

6-Amino-4-(((trans)-2-methoxycyclopentyl)oxy)nicotinonitrile was prepared in accordance with the method of Intermediate 7.

MS m/z (ESI): 234.1 [M+H]⁺.

Intermediate 20: Preparation of (R)-6-amino-4-((1-methoxypropan-2-yl)oxy)nicotinonitrile

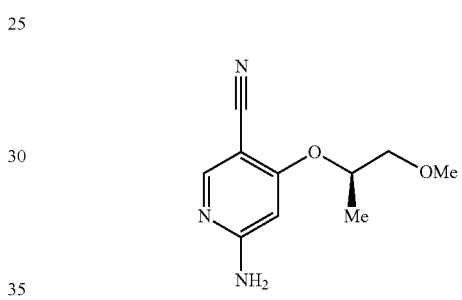

(R)-6-Amino-4-((1-methoxypropan-2-yl)oxy)nicotinonitrile was prepared in accordance with the method of Intermediate 7.

MS m/z (ESI): 208.1 [M+H]⁺.

Intermediate 21: Preparation of 2-(dimethoxymethyl)-5,6,7,8-tetrahydro-1,8-naphthyridin-3-carbaldehyde

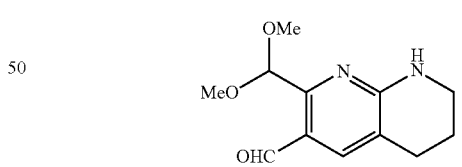

Step 1: Preparation of 2-(dimethoxymethyl)-1,8-naphthyridine

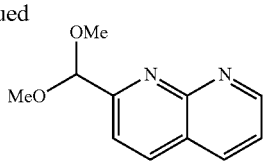

2-Aminonicotine aldehyde (25.0 g, 205 mmol) and 1,1-dimethoxypropan-2-one (31.4 g, 266 mmol) were mixed and dissolved in a mixed solvent of ethanol (500 mL) and water (50 mL), followed by addition of aqueous NaOH solution (3 M, 88.7 mL, 266 mmol). The reaction solution was stirred at room temperature for 3 hours, and then concentrated. The resulting residue was dissolved in EtOAc, washed twice with saturated brine, dried over anhydrous sodium sulfate, and concentrated to obtain the title compound 2-(dimethoxymethyl)-1,8-naphthyridine (42.3 g) which was directly used in the next step.

Step 2: Preparation of 7-(dimethoxymethyl)-1,2,3,4-tetrahydro-1,8-naphthyridine

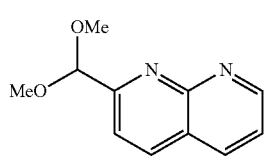

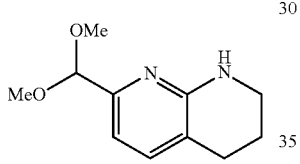

PtO$_2$ (1.25 g) was added to a solution of 2-(dimethoxymethyl)-1,8-naphthyridine (42.3 g, 205 mmol) in ethanol (600 mL). After stirring for 36 hours in a hydrogen atmosphere at room temperature and normal pressure, the reaction was filtered with diatomite to remove the catalyst. The filtrate was concentrated to obtain the title compound 7-(dimethoxymethyl)-1,2,3,4-tetrahydro-1,8-naphthyridine (42.7 g) which was directly used in the next step.

Step 3: Preparation of 6-bromo-7-(dimethoxymethyl)-1,2,3,4-tetrahydro-1,8-naphthyridine

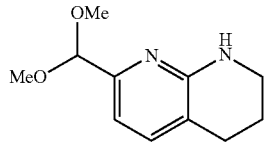

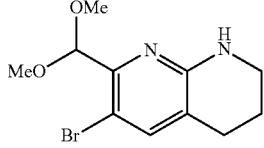

NBS (38.3 g, 215 mmol) was added in batches to a solution of 7-(dimethoxymethyl)-1,2,3,4-tetrahydro-1,8-naphthyridine (42.7 g, 205 mmol) in MeCN (1 L) at room temperature. The reaction solution was stirred for 1 hour and concentrated. The resulting residue was dissolved in CH$_2$Cl$_2$, washed with 1 M NaOH aqueous solution and saturated brine successively, dried over anhydrous sodium sulfate and concentrated. The resulting residue was subjected to column chromatography to obtain the title compound 6-bromo-7-(dimethoxymethyl)-1,2,3,4-tetrahydro-1,8-naphthyridine (47.5 g, total yield of three steps: 81%).

$^1$H NMR (400 MHz, CDCl$_3$): δ 7.27 (s, 1H), 5.55 (s, 1H), 5.39 (br s, 1H), 3.45 (s, 6H), 3.38 (m, 2H), 2.70 (t, J=6.0 Hz, 2H), 1.88 (m, 2H);

MS m/z (ESI): 287.0 [M+H]$^+$.

Step 4: Preparation of 2-(dimethoxymethyl)-5,6,7,8-tetrahydro-1,8-naphthyridin-3-carbaldehyde

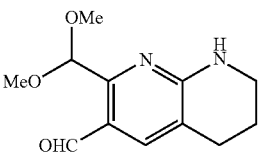 [SMILES: COC(OC)c1nc2c(cc1C=O)CCCN2]

MeLi (1.6 M THF solution, 0.30 mL, 0.48 mmol) was added dropwise to a solution of 6-bromo-7-(dimethoxymethyl)-1,2,3,4-tetrahydro-1,8-naphthyridine (114 mg, 0.397 mmol) in THF (3 mL) at −78° C. After the reaction solution was stirred at this temperature for 5 minutes, n-BuLi (1.6 M THF solution, 0.50 mL, 0.80 mmol) was added dropwise, and then the reaction solution was stirred for another 15 minutes. The reaction solution was warmed up slowly to room temperature and stirred for 30 minutes after dry DMF (0.12 mL, 1.6 mmol) was added dropwise and slowly. Saturated aqueous NH$_4$Cl solution was added, and then the reaction solution was stirred for 5 minutes, extracted twice with CH$_2$Cl$_2$. The organic phases were combined, dried over anhydrous sodium sulfate and concentrated. The resulting residue was subjected to column chromatography to obtain the title compound 2-(dimethoxymethyl)-5,6,7,8-tetrahydro-1,8-naphthyridin-3-carbaldehyde (73 mg, 78%).

1H NMR (400 MHz, CDCl$_3$): δ 10.32 (s, 1H), 7.75 (s, 1H), 5.93 (br s, 1H), 5.44 (s, 1H), 3.49 (m, 8H), 2.76 (t, J=6.0 Hz, 2H), 1.91 (m, 2H);

MS m/z (ESI): 237.1 [M+H]$^+$.

Intermediate 22: Preparation of phenyl 7-(dimethoxymethyl)-6-((3-carbonylmorpholino)methyl)-3,4-dihydro-1,8-naphthyridin -1(2H)-carboxylate

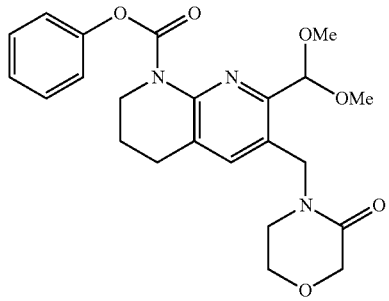 [SMILES: COC(OC)c1nc2c(cc1CN1CCOCC1=O)CCCN2C(=O)Oc1ccccc1]

Step 1: Preparation of 4-((2-(dimethoxymethyl)-5,6,7,8-tetrahydro-1,8-naphthyridin-3-yl)methyl)morpholin -3-one

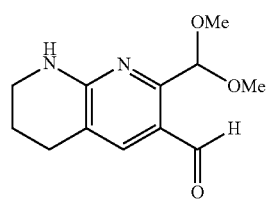 

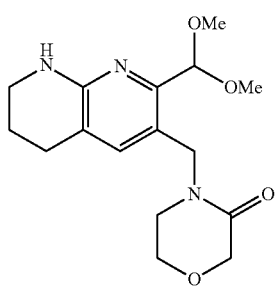

2-(Dimethoxymethyl)-5,6,7,8-tetrahydro-1,8-naphthyridin-3-carbaldehyde (8.1 g, 34.4 mmol), ethyl 2-(2-aminoethoxy)acetate hydrochloride (7.54 g, 41.2 mmol), TEA (6.5 mL, 48 mmol) and NaBH(OAc)$_3$ (11.6 g, 54.9 mmol) were mixed in DCE (150 mL), and then the reaction was carried out at room temperature overnight in a nitrogen atmosphere. The reaction solution was warmed up to 85° C. and stirred for 5 h, then diluted with dichloromethane (300 mL), and washed with saturated aqueous NaHCO$_3$ solution (300 mL×2). The organic phase was washed with saturated brine, dried over anhydrous sodium sulfate and concentrated. The resulting residue was subjected to column chromatography to obtain the title compound 4-((2-(dimethoxymethyl)-5,6,7,8-tetrahydro-1,8-naphthyridin-3-yl)methyl)morpholin -3-one (9.5 g, 86%).

MS m/z (ESI): 322.1 [M+H]$^+$.

Step 2: Preparation of phenyl 7-(dimethoxymethyl)-6-((3-carbonylmorpholino)methyl)-3,4-dihydro-1,8-naphthyridin -1(2H)-carboxylate

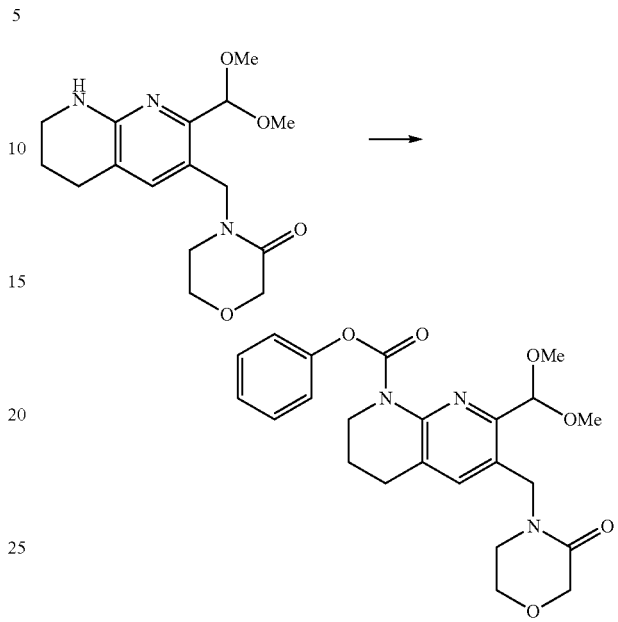

4-((2-(Dimethoxymethyl)-5,6,7,8-tetrahydro-1,8-naphthyridin-3-yl)methyl)morpholin -3-one (642 mg, 2 mmol) and diphenyl carbonate (643 mg, 3 mmol) were mixed in THF (15 mL). The mixture was cooled to −78° C. in a nitrogen atmosphere, followed by addition of a solution of LiHMDS in THF (4 mL, 4 mmol). The reaction solution was warmed up slowly to room temperature and stirred overnight. Saturated aqueous NH$_4$Cl solution (100 mL) was added, and then the mixture was extracted with ethyl acetate (100 mL×2). The organic phase was washed with saturated brine, dried over anhydrous sodium sulfate and concentrated. The resulting residue was subjected to column chromatography to obtain the title compound phenyl-7-(dimethoxymethyl)-6-((3-carbonylmorpholino)methyl)-3,4-dihydro-1,8-naphthyridin -1(2H)-carboxylate (400 mg, 45%).

MS m/z (ESI): 442.1 [M+H]$^+$.

Intermediate 23: Preparation of phenyl 7-(dimethoxymethyl)-6-((3-carbonyl-1,4-oxazepin-4-yl)methyl)-3,4-dihydro-1,8-naphthyridin-1(2H)-carboxylate

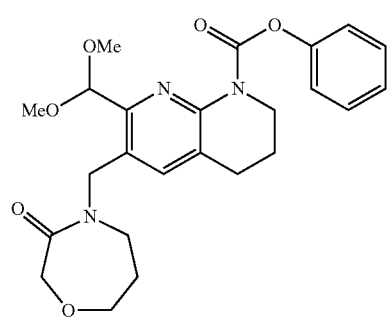 [SMILES: COC(OC)c1nc2c(cc1CN1CCCOCC1=O)CCCN2C(=O)Oc1ccccc1]

Step 1: Preparation of ethyl 2-(3-(((2-(dimethoxymethyl)-5,6,7,8-tetrahydro-1,8-naphthyridin-3-yl)methyl)amino)propoxy)acetate

Step 2: Preparation of 2-(3-(((2-(dimethoxymethyl)-5,6,7,8-tetrahydro-1,8-naphthyridin-3-yl)methyl)amino)propoxy)acetate

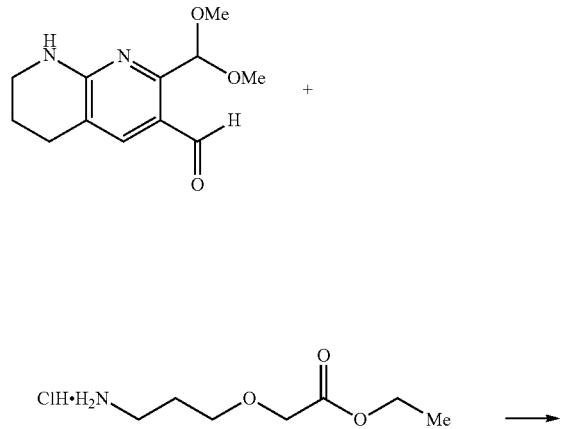

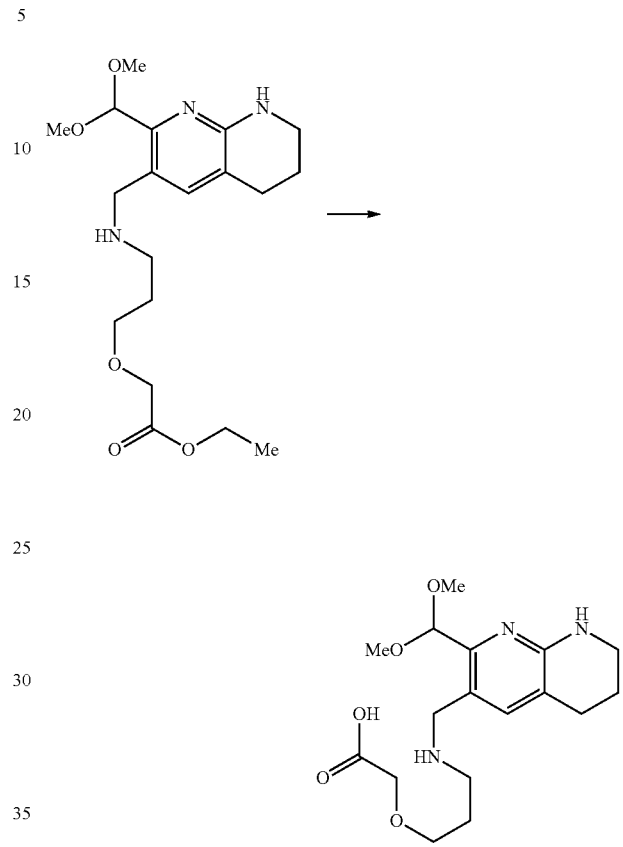

2-(Dimethoxymethyl)-5,6,7,8-tetrahydro-1,8-naphthyridin-3-carbaldehyde (118 mg, 0.5 mmol), ethyl 2-(3-aminopropoxy)acetate hydrochloride (118.2 mg, 0.6 mmol), TEA (0.15 mL, 0.7 mmol) and NaBH(OAc)$_3$ (169.6 mg, 0.8 mmol) were mixed in DCE (3 mL), and then the reaction was carried out overnight at room temperature in a nitrogen atmosphere. The mixture was diluted with dichloromethane (30 mL), and washed with saturated aqueous NaHCO$_3$ solution (30 mL×2). The organic phase was washed with saturated brine, dried over anhydrous sodium sulfate and concentrated.

The resulting residue was subjected to column chromatography to obtain the title compound ethyl 2-(3-(((2-(dimethoxymethyl)-5,6,7,8-tetrahydro-1,8-naphthyridin-3-yl)methyl)amino) propoxy)acetate (177 mg, 93%).

MS m/z (ESI): 382.1 [M+H]$^+$.

Ethyl 2-(3-(((2-(dimethoxymethyl)-5,6,7,8-tetrahydro-1,8-naphthyridin-3-yl)methyl)amino) propoxy)acetate (176.6 mg, 0.46 mmol) and LiOH (42 mg, 1 mmol) were mixed in a solution of methanol/THF/water (volume ratio: 2/1/1, 2 mL), and then the reaction was carried out overnight at room temperature. The reaction solution was concentrated to obtain the crude title compound 2-(3-(((2-(dimethoxymethyl)-5,6,7,8-tetrahydro-1,8-naphthyridin-3-yl)methyl) amino) propoxy)acetate (200 mg).

MS m/z (ESI): 354.1 [M+H]$^+$.

Step 3: Preparation of 4-((2-(dimethoxymethyl)-5,6,7,8-tetrahydro-1,8-naphthyridin-3-yl)methyl)-1,4-oxazepin-3-one

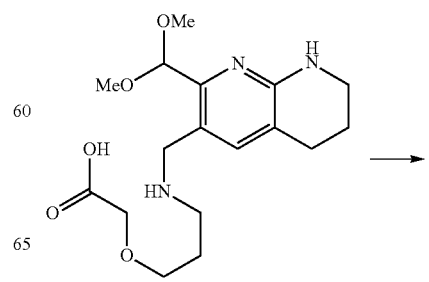

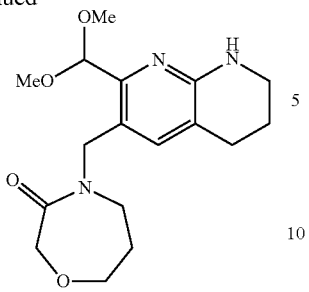

2-(3-((2-(Dimethoxymethyl)-5,6,7,8-tetrahydro-1,8-naphthyridin-3-yl)methyl)amino) propoxy)acetate (200 mg, 0.46 mmol), HATU (380 mg, 1 mmol) and DIPEA (0.26 mL, 1.5 mmol) were mixed in DMF (5 mL), and then the reaction was carried out for 2 hours at room temperature. After addition of saturated aqueous NaHCO₃ solution (50 mL), the mixture was extracted with ethyl acetate (50 mL×2). The organic phase was washed with saturated brine, dried over anhydrous sodium sulfate and concentrated. The resulting residue was subjected to column chromatography to obtain the title compound 4-((2-(dimethoxymethyl)-5,6,7,8-tetrahydro-1,8-naphthyridin-3-yl)methyl)-1,4-oxazepin-3-one (100 mg, 60%).

MS m/z (ESI): 336.1 [M+H]⁺.

Step 4: Preparation of phenyl 7-(dimethoxymethyl)-6-((3-carbonyl-1,4-oxazepin-4-yl)methyl)-3,4-dihydro-1,8-naphthyridin-1(2H)-carboxylate

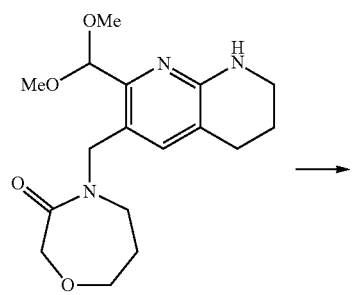

→

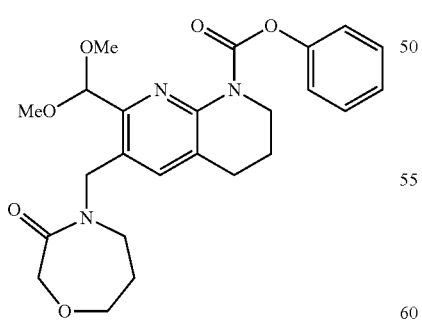

Phenyl 7-(dimethoxymethyl)-6-((3-carbonyl-1,4-oxazepin-4-yl)methyl)-3,4-dihydro-1,8-naphthyridin-1(2H)-carboxylate was prepared in accordance with the method of Intermediate 22.

MS m/z (ESI): 456.1 [M+H]⁺.

Intermediate 24: Preparation of phenyl 7-(dimethoxymethyl)-6-((4-methyl-2-carbonyl-1,4-diazoheptyl-1-yl)methyl)-3,4-dihydrogen -1,8-naphthyridin-1(2H)-carboxylate

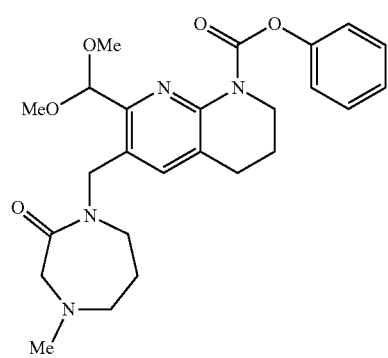 [SMILES: COC(OC)c1nc2c(cc1CN1CCCN(C)CC1=O)CCCN2C(=O)Oc1ccccc1]

Phenyl 7-(dimethoxymethyl)-6-((4-methyl-2-carbonyl-1,4-diazoheptyl-1-yl)methyl)-3,4-dihydrogen -1,8-naphthyridin-1(2H)-carboxylate was prepared in accordance with the method of Intermediate 23.

MS m/z (ESI): 469.1 [M+H]⁺.

Intermediate 25: Preparation of phenyl (S)-7-(dimethoxymethyl)-6-((4-methyl-2-carbonyloxazolidin-3-yl)methyl)-3,4-dihydro -1,8-naphthyridin-1(2H)-carboxylate

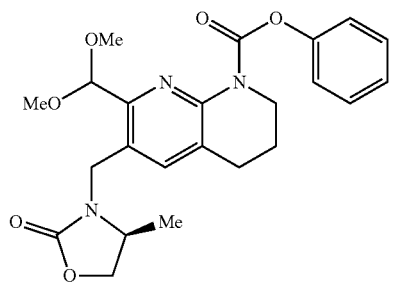 [SMILES: COC(OC)c1nc2c(cc1CN1C(=O)OC[C@@H]1C)CCCN2C(=O)Oc1ccccc1]

Phenyl (S)-7-(dimethoxymethyl)-6-((4-methyl-2-carbonyloxazolidin-3-yl)methyl)-3,4-dihydro -1,8-naphthyridin-1(2H)-carboxylate was prepared in accordance with the method of Intermediate 22.

MS m/z (ESI): 442.2 [M+H]⁺.

Intermediate 26: Preparation of phenyl 7-(dimethoxymethyl)-6-((8-carbonyl-4-oxa-7-azaspiro[2.5]octane-7-yl)methyl)-3,4-dihydrogen-1,8-naphthyridin-1(2H)-carboxylate

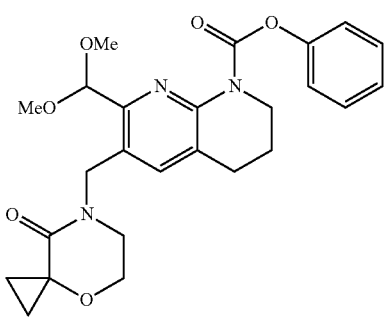 [SMILES: COC(OC)c1nc2c(cc1CN1CCOC3(CC3)C1=O)CCCN2C(=O)Oc1ccccc1]

Phenyl 7-(dimethoxymethyl)-6-((8-carbonyl-4-oxa-7-azaspiro[2.5]octane-7-yl)methyl)-3,4-dihydrogen -1,8-naphthyridin-1(2H)-carboxylate was prepared in accordance with the method of Intermediate 22.

MS m/z (ESI): 468.2 [M+H]$^+$.

Intermediate 27: Preparation of phenyl 7-(dimethoxymethyl)-6-((6-carbonyl-4-oxa-7-azaspiro[2.5]octane-7-yl)methyl)-3,4-dihydrogen-1,8-naphthyridin-1(2H)-carboxylate

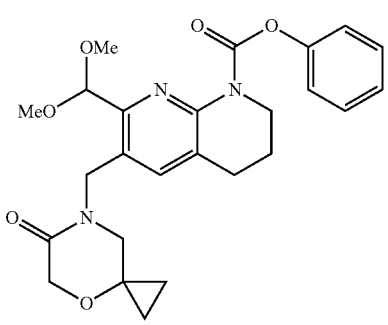 [SMILES: COC(OC)c1nc2c(cc1CN1CC3(CC3)OCC1=O)CCCN2C(=O)Oc1ccccc1]

Phenyl 7-(dimethoxymethyl)-6-((6-carbonyl-4-oxa-7-azaspiro[2.5]octane-7-yl)methyl)-3,4-dihydrogen -1,8-naphthyridin-1(2H)-carboxylate was prepared in accordance with the method of Intermediate 22.

MS m/z (ESI): 468.2 [M+H]$^+$.

Intermediate 28: Preparation of phenyl 7-(dimethoxymethyl)-6-((5-carbonyl-7-oxa-4-azaspiro[2.5]octane-4-yl)methyl)-3,4-dihydrogen-1,8-naphthyridin-1(2H)-carboxylate

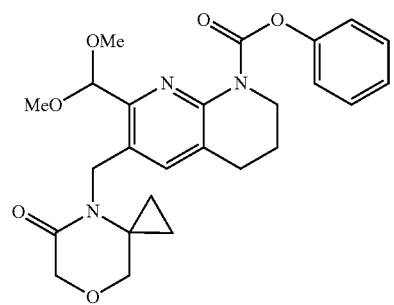 [SMILES: COC(OC)c1nc2c(cc1CN1C(=O)COCC13CC3)CCCN2C(=O)Oc1ccccc1]

Phenyl 7-(dimethoxymethyl)-6-((5-carbonyl-7-oxa-4-azaspiro[2.5]octane-4-yl)methyl)-3,4-dihydrogen-1,8-naphthyridin-1(2H)-carboxylate was prepared in accordance with the method of Intermediate 22.

MS m/z (ESI): 468.2 [M+H]$^+$.

Intermediate 29: Preparation of phenyl 7-(dimethoxymethyl)-6-((2-carbonyl-1,3-oxazepin-3-yl)methyl)-3,4-dihydro-1,8-naphthyridin -1(2H)-carboxylate

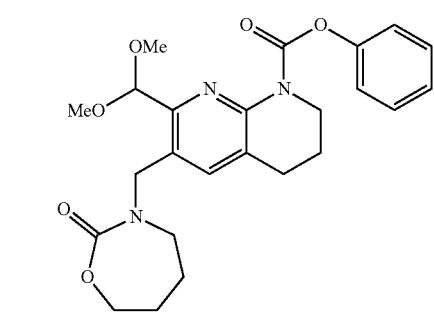 [SMILES: COC(OC)c1nc2c(cc1CN1CCCCOC1=O)CCCN2C(=O)Oc1ccccc1]

Step 1: Preparation of 4-(((2-(dimethoxymethyl)-5,6,7,8-tetrahydro-1,8-naphthyridin-3-yl)methyl)amino) butan-1-ol

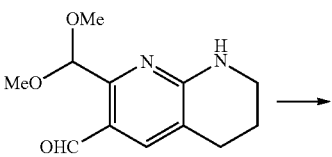

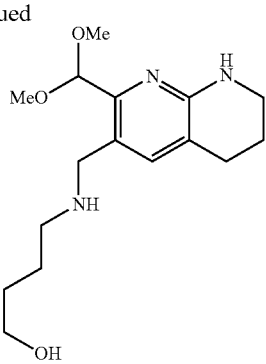

2-(Dimethoxymethyl)-5,6,7,8-tetrahydro-1,8-naphthyridin-3-carbaldehyde (1.0 g, 4.2 mmol) and 4-aminobutan-1-ol (0.45 g, 5.1 mmol) were dissolved in DCE (15 mL) at room temperature, and then the reaction solution was stirred for 2 hours. After addition of NaBH(OAc)₃ (1.35 g, 6.4 mmol), the reaction solution was stirred at room temperature overnight, and then diluted with CH₂Cl₂ (100 mL). The organic phase was washed with water (10 mL) and saturated brine (15 mL) successively, dried over anhydrous sodium sulfate and concentrated. The resulting residue was subjected to column chromatography to obtain the title compound 4-(((2-(dimethoxymethyl)-5,6,7,8-tetrahydro-1,8-naphthyridin-3-yl)methyl)amino)butan -1-ol (0.9 g, 69%).

¹H NMR (400 MHz, CDCl₃) δ 7.13 (s, 1H), 5.17 (s, 1H), 4.84 (s, 1H), 3.73 (s, 2H), 3.66-3.49 (m, 2H), 3.42 (s, 6H), 3.40-3.36 (m, 2H), 2.71 (t, J=6.3 Hz, 2H), 2.68-2.56 (m, 2H), 1.95-1.81 (m, 2H), 1.74-1.55 (m, 4H);

MS m/z (ESI): 310.2 [M+H]⁺.

Step 2: Preparation of 3-((2-(dimethoxymethyl)-5,6,7,8-tetrahydro-1,8-naphthyridin-3-yl)methyl)-1,3-oxazepine-2-one

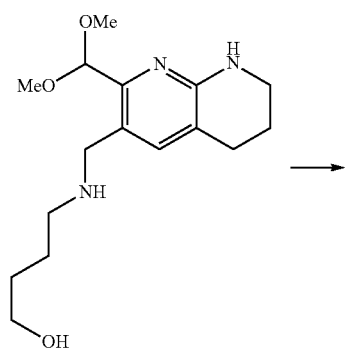

4-(((2-(Dimethoxymethyl)-5,6,7,8-tetrahydro-1,8-naphthyridin-3-yl)methyl)amino) butan-1-ol (0.6 g, 1.94 mmol) was dissolved in DCE (15 mL) in an ice water bath, followed by addition of bis(trichloromethyl)carbonate (0.22 g, 0.76 mmol). Triethylamine (0.78 g, 7.76 mmol) was added dropwise and slowly. The reaction solution was stirred for 3 hours at room temperature, then warmed up to 80° C., and stirred for 6 hours at 80° C. After cooling to room temperature, the reaction solution was diluted with CH₂Cl (100 mL). The organic phase was washed with water (10 mL) and saturated brine (15 mL) successively, dried over anhydrous sodium sulfate and concentrated. The resulting residue was subjected to column chromatography to obtain the title compound 3-((2-(dimethoxymethyl)-5,6,7,8-tetrahydro-1,8-naphthyridin-3-yl)methyl)-1,3-oxazepine -2-one (0.37 g, 57%).

MS m/z (ESI): 336.2 [M+H]⁺.

Step 3: Preparation of phenyl 7-(dimethoxymethyl)-6-((2-carbonyl-1,3-oxazepin-3-yl)methyl)-3,4-dihydro-1,8-naphthyridin -1(2H)-carboxylate

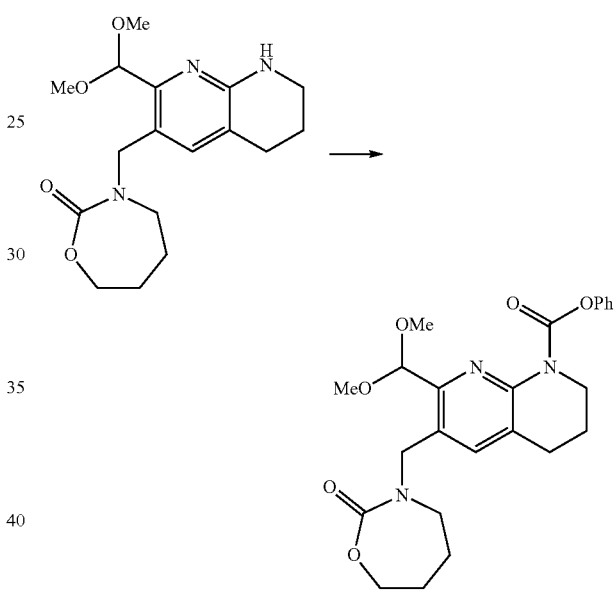

Phenyl 7-(dimethoxymethyl)-6-((2-carbonyl-1,3-oxazepin-3-yl)methyl)-3,4-dihydro-1,8-naphthyridin -1(2H)-carboxylate was prepared in accordance with the method of Step 4 of Intermediate 23.

¹H NMR (400 MHz, CDCl₃) δ 7.56 (s, 1H), 7.38(m, 2H), 7.21 (m, 3H), 5.22 (s, 1H), 4.77 (s, 2H), 4.16 (m, 2H), 3.95 (m, 2H), 3.39 (s, 6H), 3.25 (m, 2H), 2.84 (t, J=6.5 Hz, 2H), 1.87 (m, 2H), 1.64 (m, 4H);

MS m/z (ESI): 456.2 [M+H]⁺.

Intermediate 30: Preparation of (R)-6-amino-4-((1-methoxypropan-2-yl)amino)nicotinonitrile

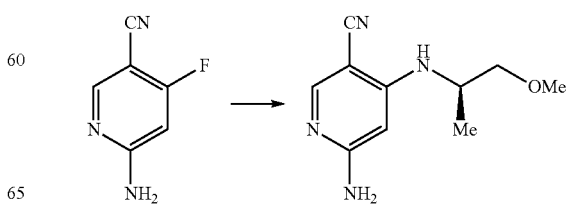

6-Amino-4-fluoronicotinonitrile (1.5 g, 10.9 mmol) and (R)-1-methoxypropan-2-amine (1.2 g, 13 mmol) were dissolved in DMA (10 mL), followed by addition of DIPEA (4.2 g, 33 mmol). The reaction solution was warmed up to 130° C., stirred for 12 hours and concentrated. The resulting residue was subjected to column chromatography to obtain the title compound (R)-6-amino-4-((1-methoxypropan-2-yl)amino)nicotinonitrile (2 g, 89%).

$^1$H NMR (400 MHz, DMSO) δ 7.94 (s, 1H), 6.41 (s, 2H), 5.75 (d, J=8.2 Hz, 1H), 5.66 (s, 1H), 3.70-3.60 (m, 1H), 3.45-3.40 (m, 1H), 3.35-3.32 (m, 1H), 3.28 (s, 3H), 1.14 (d, J=6.5 Hz, 3H);

MS m/z (ESI): 207.1 [M+H]$^+$.

Intermediate 31: Preparation of (3,4)-trans-3-methoxytetrahydro-2H-pyran-4-ol and (3,4)-trans-4-methoxytetrahydro-2H-pyran-3-ol

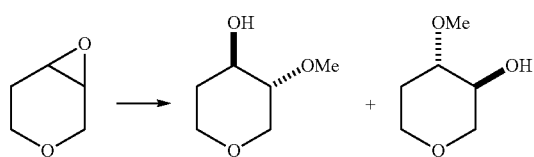 [SMILES: C1CC2OC2CO1 ; CO[C@@H]1COCC[C@H]1O ; CO[C@H]1CCOC[C@@H]1O]

3,7-Dioxabicyclo[4.1.0]heptane (500 mg, 5.0 mmol) was dissolved in a solution of 0.2 N H$_2$SO$_4$ in MeOH (46 mL), and then the reaction solution was stirred for 2 hours. The reaction solution was neutralized with saturated aqueous sodium bicarbonate solution (20 mL), and then concentrated to remove most of the methanol. The reaction solution was extracted with ethyl acetate (20 mL×3). The combined organic phase was washed with saturated brine, dried over anhydrous sodium sulfate and concentrated. The resulting residue was subjected to column chromatography to obtain a mixture of title compounds (3,4)-trans-3-methoxytetrahydro-2H-pyran-4-ol and (3,4)-trans-4-methoxytetrahydro-2H-pyran-3-ol (260 mg, the ratio was about 3:7 and the yield was 39%).

Intermediate 32: Preparation of (3,4)-trans-4-methoxytetrahydro-2H-pyran-3-amine

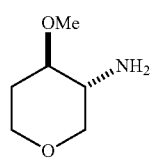

Step 1: Preparation of (3,4)-trans-3-azidotetrahydro-2H-pyran-4-ol

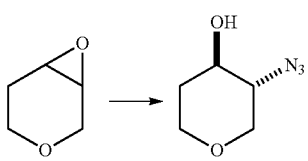 [SMILES: C1CC2OC2CO1 ; [N-]=[N+]=N[C@@H]1COCC[C@H]1O]

3,7-Dioxabicyclo[4.1.0]heptane (500 mg, 5.0 mmol), NaN$_3$ (1.6 g, 25.0 mmol), and ammonium chloride (535 mg, 10.0 mmol) were mixed in a solution of MeOH in water (50 mL, v/v=1:8). The reaction solution was stirred at 80° C. for 4 hours in a nitrogen atmosphere, neutralized with saturated aqueous sodium bicarbonate solution (50 mL), and extracted with ethyl acetate (50 mL×3). The organic phases were combined, washed with saturated brine, dried over anhydrous sodium sulfate and concentrated. The resulting residue was purified by column chromatography to obtain (3,4)-trans-3-azidotetrahydro-2H-pyran-4-ol (280 mg, 39%).

Step 2: Preparation of (3,4)-trans-3-azido-4-methoxytetrahydro-2H-pyran

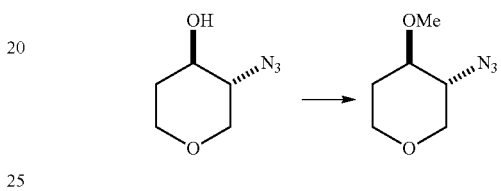

(3,4)-Trans-3-azidotetrahydro-2H-pyran-4-ol (280 mg, 2.0 mmol) was dissolved in dry THF (5 mL). The reaction flask was placed in an ice water bath in a nitrogen atmosphere, and NaH (120 mg, 3.0 mmol) was added in batches. The reaction solution was warmed up to room temperature slowly, stirred for 30 minutes, and cooled in an ice water bath. CH$_3$I (0.4 mL, 6.0 mmol) was added dropwise, and the reaction solution was warmed up to room temperature and stirred for 40 min. Then the reaction solution was diluted with ethyl acetate (10 mL), and saturated aqueous NaHCO$_3$ solution (15 mL) was added. The two phases were separated, and then the aqueous phase was extracted with ethyl acetate (10 mL×3). The organic phases were combined, washed with saturated brine, dried over anhydrous sodium sulfate and concentrated. The resulting residue was subjected to column chromatography to obtain (3,4)-trans-3-azido-4-methoxytetrahydro-2H-pyran (230 mg, 75%).

Step 3: Preparation of (3,4)-trans-4-methoxytetrahydro-2H-pyran-3-amine

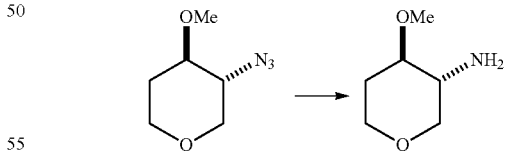

(3,4)-Trans-3-azido-4-methoxytetrahydro-2H-pyran (230 mg, 1.5 mmol) was dissolved in MeOH (6 mL), followed by addition of 10% Pd/C (23 mg). The reaction was carried out for 4 hours at room temperature in a hydrogen atmosphere. Then the reaction solution was filtered. The filter cake was washed 3 times with MeOH (3 mL). The filtrate was combined and concentrated to obtain the title compound (3,4)-trans-4-methoxytetrahydro-2H-pyran-3-amine (178 mg, 93%).

MS m/z (ESI): 132.2 [M+H]$^+$.

Preparation of Specific Example Compounds

Example 1

N-(5-Cyano-4-(((trans)-2-methoxycyclopentyl)amino)pyridin-2-yl)-7-formyl-6-((3-carbonylmorpholino)methyl)-3,4-dihydro-1,8-naphthyridin-1(2H)-carboxamide

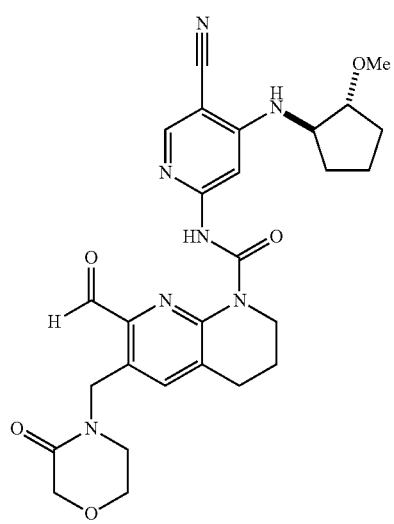

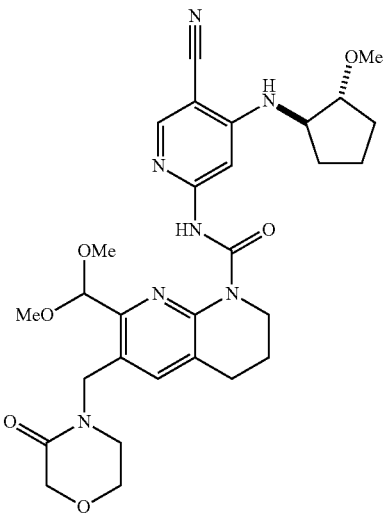

Step 1: Preparation of N-(5-cyano-4-(((trans)-2-methoxycyclopentyl)amino)pyridin-2-yl)-7-(dimethoxymethyl)-6-((3-carbonylmorpholino)methyl)-3,4-dihydro-1,8-naphthyridin-1(2H)-carboxamide

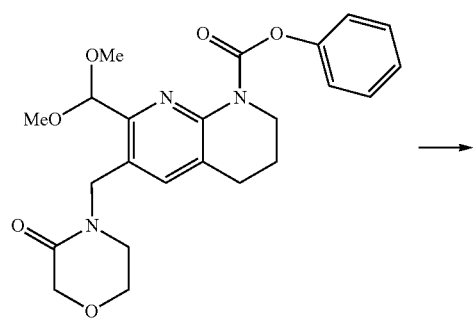

6-Amino-4-(((trans)-2-methoxycyclopentyl)amino)nicotinonitrile (20 mg, 0.09 mmol), and phenyl 7-(dimethoxymethyl)-6-((3-carbonylmorpholino)methyl)-3,4-dihydro-1,8-naphthyridin -1(2H)-carboxylate (38 mg, 0.09 mmol) were mixed in THF (5 mL). The mixture was cooled to −78° C. in a nitrogen atmosphere, followed by addition of a solution of LiHMDS in THF (0.2 mL, 0.2 mmol). The reaction solution was warmed up to room temperature naturally, and stirred overnight. After addition of saturated aqueous NH$_4$Cl solution (50 mL), the reaction solution was extracted with ethyl acetate (50 mL×2). The organic phase was washed with saturated brine, dried over anhydrous sodium sulfate and concentrated. The resulting residue was subjected to column chromatography to obtain the title compound N-(5-cyano-4-(((trans)-2-methoxycyclopentyl)amino)pyridin-2-yl)-7-(dimethoxymethyl) -6-((3-carbonylmorpholino)methyl)-3,4-dihydro-1,8-naphthyridin-1(2H)-carboxamide (23 mg, 46%).

MS m/z (ESI): 580.2 [M+H]$^+$.

Step 2: Preparation of N-(5-cyano-4-(((trans)-2-methoxycyclopentyl)amino)pyridin-2-yl)-7-formyl-6-((3-carbonylmorpholino)methyl)-3,4-dihydro-1,8-naphthyridin-1(2H)-carboxamide

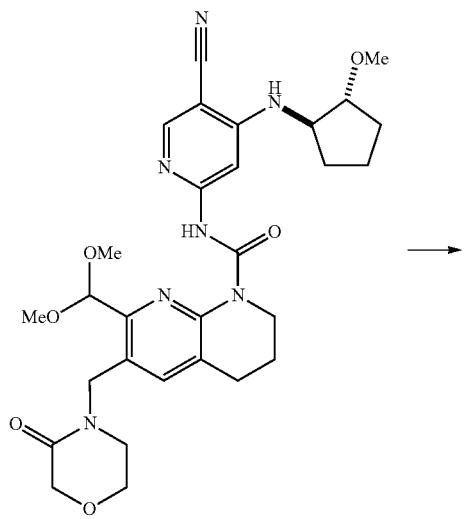

→ reaction was carried out for 2 hours at room temperature. After addition of saturated aqueous NaHCO$_3$ solution (50 mL), the reaction solution was extracted with ethyl acetate (50 mL×2). The organic phase was washed with saturated brine, dried over anhydrous sodium sulfate and concentrated. The resulting residue was subjected to column chromatography to obtain the title compound N-(5-cyano-4-(((trans)-2-methoxycyclopentyl)amino)pyridin-2-yl)-7-formyl-6-((3-carbonylmorpholino) methyl)-3,4-dihydro-1,8-naphthyridin-1(2H)-carboxamide (15 mg, 70%).

$^1$H NMR (400 MHz, CDCl$_3$) δ 13.56 (s, 1H), 10.23 (s, 1H), 8.17 (s, 1H), 7.73 (s, 1H), 7.66 (s, 1H), 5.11 (s, 2H), 4.87 (m, 1H), 4.26 (s, 2H), 4.09 (m, 2H), 3.93-3.85 (m, 3H), 3.69 (m, 1H), 3.42-3.39 (m, 4H), 2.93 (m, 2H), 2.33 (m, 1H), 2.07-2.01 (m, 2H), 1.95-1.50 (m, 6H);

MS m/z (ESI): 534.1 [M+H]$^+$.

Example 2

N-(5-Cyano-4-((2-(pyrrolidin-1-yl)ethyl)amino)pyridin-2-yl)-7-formyl-6-((3-carbonylmorpholino)methyl)-3,4-dihydro-1,8-naphthyridin-1(2H)-carboxamide

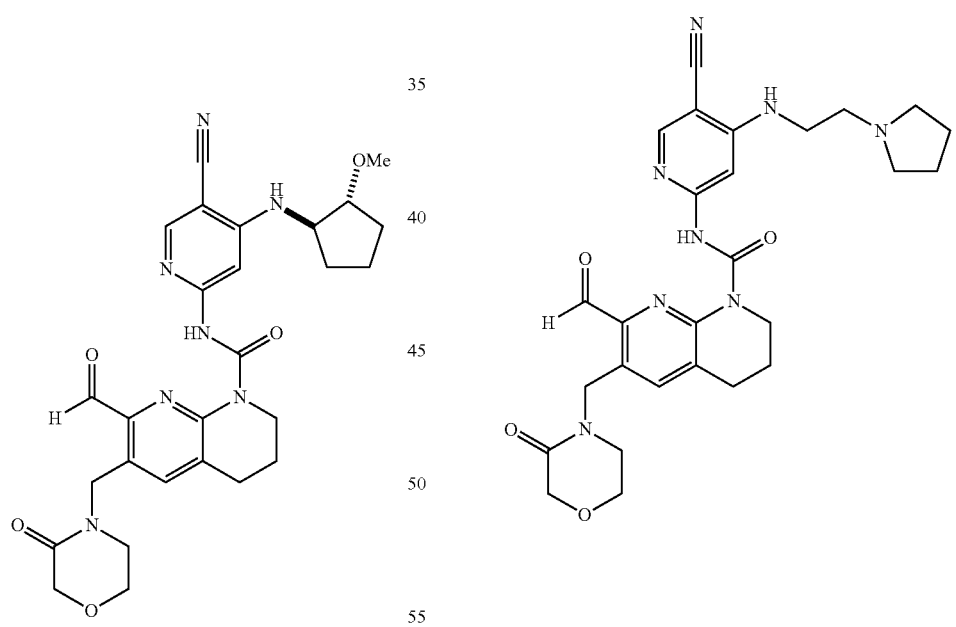

N-(5-Cyano-4-(((trans)-2-methoxycyclopentyl)amino)pyridin-2-yl)-7-(dimethoxymethyl) -6-((3-carbonylmorpholino)methyl)-3,4-dihydro-1,8-naphthyridin-1(2H)-carboxamide (23 mg, 0.04 mmol) was dissolved in a mixture of THF and water (volume ratio: 11/4, 1.5 mL), followed by addition of concentrated HCl (0.15 mL, 1.8 mmol). The N-(5-Cyano-4-((2-(pyrrolidin-1-yl)ethyl)amino)pyridin-2-yl)-7-formyl-6-((3-carbonylmorpholino) methyl)-3,4-dihydro-1,8-naphthyridin-1(2H)-carboxamide was prepared in accordance with the method of Example 1.

$^1$H NMR (400 MHz, CDCl$_3$) δ 13.56 (s, 1H), 10.23 (s, 1H), 8.17 (s, 1H), 7.67 (s, 1H), 7.53 (s, 1H), 5.83 (s, 1H), 5.11 (s, 2H), 4.26 (s, 2H), 4.11-4.05 (m, 2H), 3.91-3.86 (m, 2H), 3.47-3.38 (m, 4H), 2.94 (m, 2H), 2.87 (m, 2H), 2.68 (m, 4H), 2.08-2.01 (m, 2H), 1.86 (m, 4H);

MS m/z (ESI): 533.2 [M+H]$^+$.

Example 3

N-(5-Cyano-4-((2-methyltetrahydrofuran-3-yl)thio)pyridin-2-yl)-7-formyl-6-((3-carbonylmorpholino)methyl)-3,4-dihydro-1,8-naphthyridin-1(2H)-carboxamide

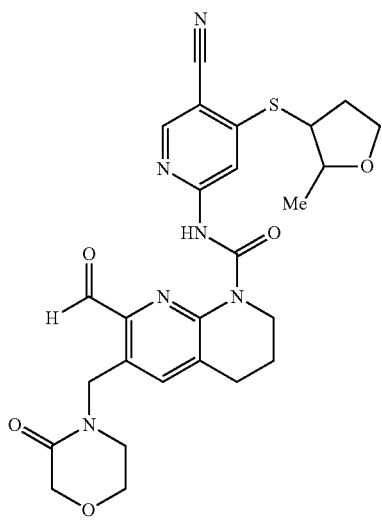 [SMILES: CC1OCCC1Sc1cc(NC(=O)N2CCCc3cc(CN4CCOCC4=O)c(C=O)nc32)ncc1C#N]

N-(5-Cyano-4-((2-methyltetrahydrofuran-3-yl)thio)pyridin-2-yl)-7-formyl-6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$) δ 13.83 (s, 1H), 10.16 (s, 1H), 8.30 (s, 1H), 8.25 (s, 1H), 7.62 (s, 1H), 5.04 (s, 2H), 4.34 (m, 1H), 4.19 (s, 2H), 4.06-3.99 (m, 4H), 3.80 (m, 3H), 3.39-3.32 (m, 2H), 2.88 (m, 2H), 2.60 (m, 1H), 2.09-1.95 (m, 3H), 1.29 (d, J=6.4 Hz, 3H);

MS m/z (ESI): 537.1 [M+H]$^+$.

Example 4

N-(5-Cyano-4-(3-methoxypyrrolidin-1-yl)pyridin-2-yl)-7-formyl-6-((3-carbonylmorpholino)methyl)-3,4-dihydro-1,8-naphthyridin-1(2H)-carboxamide

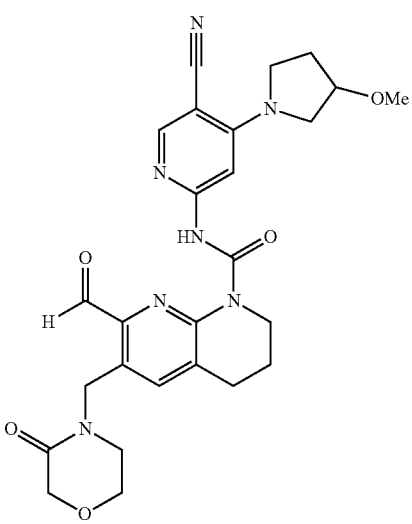 [SMILES: COC1CCN(c2cc(NC(=O)N3CCCc4cc(CN5CCOCC5=O)c(C=O)nc43)ncc2C#N)C1]

N-(5-Cyano-4-(3-methoxypyrrolidin-1-yl)pyridin-2-yl)-7-formyl-6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$) δ 13.50 (s, 1H), 10.23 (s, 1H), 8.20 (s, 1H), 7.66 (s, 1H), 7.48 (s, 1H), 5.11 (s, 2H), 4.25 (s, 2H), 4.08 (m, 3H), 3.91-3.87 (m, 2H), 3.80 (m, 4H), 3.43-3.39 (m, 2H), 3.37 (s, 3H), 2.93 (m, 2H), 2.26-2.19 (m, 1H), 2.08-2.01 (m, 3H);

MS m/z (ESI): 520.2 [M+H]$^+$.

Example 5

N-(5-Cyano-4-((2-(cyclopentyloxy)ethyl)amino) pyridin-2-yl)-7-formyl-6-((3-carbonylmorpholino) methyl)-3,4-dihydro-1,8-naphthyridin-1(2H)-carboxamide

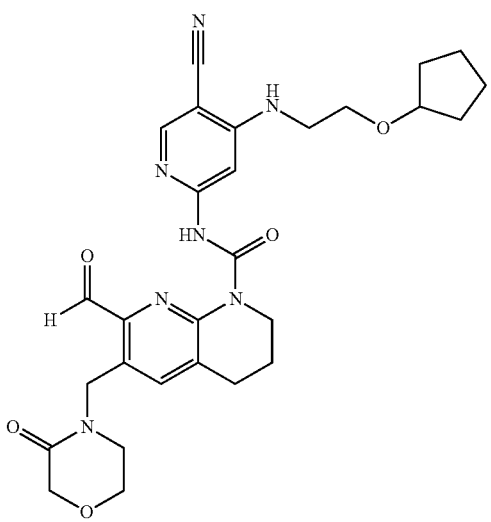 [SMILES: N#Cc1cnc(NC(=O)N2CCCc3cc(CN4CCOCC4=O)c(C=O)nc32)cc1NCCOC1CCCC1]

N-(5-Cyano-4-((2-(cyclopentyloxy)ethyl)amino)pyridin-2-yl)-7-formyl-6-((3-carbonylmorpholino) methyl)-3,4-dihydro-1,8-naphthyridin-1(2H)-carboxamide was prepared in accordance with the method of Example 1.

$^1$H NMR (400 MHz, CDCl$_3$) δ 13.56 (s, 1H), 10.23 (s, 1H), 8.17 (s, 1H), 7.66 (s, 1H), 7.55 (s, 1H), 5.35 (m, 1H), 5.11 (s, 2H), 4.26 (s, 2H), 4.11-4.06 (m, 2H), 3.95 (m, 1H), 3.91-3.86 (m, 2H), 3.64 (m, 2H), 3.48-3.39 (m, 4H), 2.94 (m, 2H), 2.04 (m, 2H), 1.71 (m, 6H), 1.56 (m, 2H);

MS m/z (ESI): 548.2 [M+H]$^+$.

Example 6

N-(5-Cyano-4-((2-methoxyethyl)amino)pyridin-2-yl)-7-formyl-6-((3-carbonyl-1,4-oxazepin-4-yl) methyl)-3,4-dihydro-1,8-naphthyridin-1(21$^{-1}$)-carboxamide

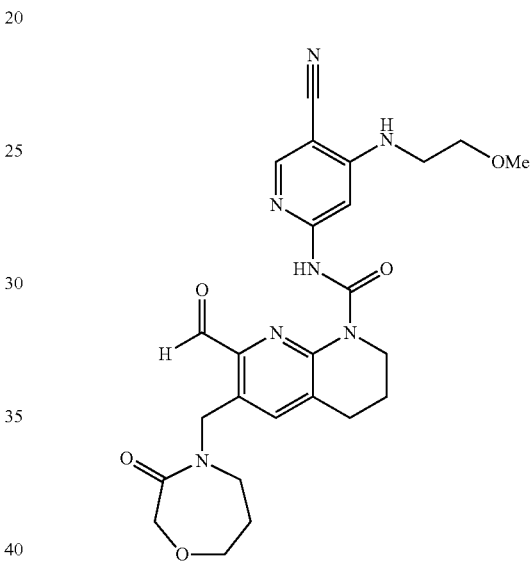

N-(5-Cyano-4-((2-methoxyethyl)amino)pyridin-2-yl)-7-formyl-6-((3-carbonyl-1,4-oxazepin-4-yl)methyl)-3,4-dihydro-1,8-naphthyridin-1(2H)-carboxamide was prepared in accordance with the method of Example 1.

$^1$H NMR (400 MHz, CDCl$_3$) δ 13.53 (s, 1H), 10.16 (s, 1H), 8.11 (s, 1H), 7.57 (s, 1H), 7.50 (s, 1H), 5.01 (s, 2H), 4.25 (s, 2H), 4.04-3.98 (m, 2H), 3.78 (m, 2H), 3.57 (m, 2H), 3.49-3.45 (m, 2H), 3.42 (m, 2H), 3.34 (s, 3H), 3.20 (s, 1H), 2.86 (m, 2H), 1.96 (m, 2H), 1.84 (m, 2H);

MS m/z (ESI): 508.1 [M+H]$^+$.

Example 7

N-(5-Cyano-4-((2-methoxyethyl)amino)pyridin-2-yl)-7-formyl-6-((4-methyl-2-carbonyl-1,4-diazoheptyl-1-yl)methyl)-3,4-dihydro-1,8-naphthyridin-1(2H)-carboxamide

Example 8

N-(5-Cyano-4-((2-methoxyphenyl)amino)pyridin-2-yl)-7-formyl-6-((3-carbonylmorpholino) methyl)-3,4-dihydro-1,8-naphthyridin-1(2H)-carboxamide

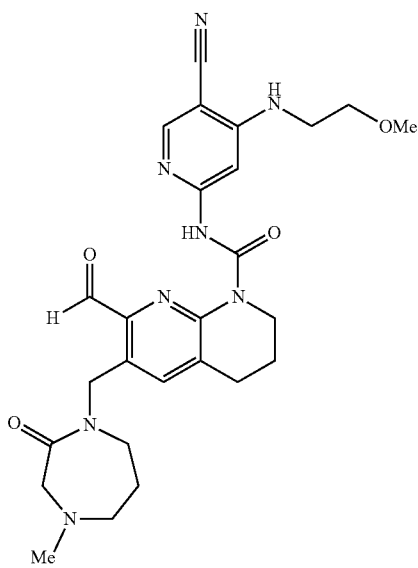 [SMILES: COCCNc1cc(NC(=O)N2CCCc3cc(CN4CCCN(C)CC4=O)c(C=O)nc32)ncc1C#N]

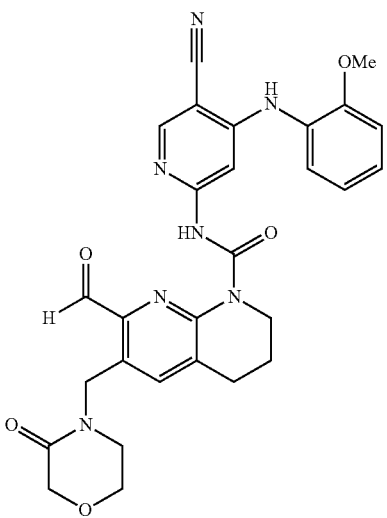 [SMILES: COc1ccccc1Nc1cc(NC(=O)N2CCCc3cc(CN4CCOCC4=O)c(C=O)nc32)ncc1C#N]

N-(5-Cyano-4-((2-methoxyethyl)amino)pyridin-2-yl)-7-formyl-6-((4-methyl-2-carbonyl -1,4-diazoheptyl-1-yl) methyl)-3,4-dihydro-1,8-naphthyridin-1(2H)-carboxamide was prepared in accordance with the method of Example 1.

$^1$H NMR (400 MHz, CDCl$_3$) δ 13.55 (s, 1H), 10.16 (s, 1H), 8.11 (s, 1H), 7.60 (s, 1H), 7.50 (s, 1H), 4.98 (s, 2H), 4.00 (m, 2H), 3.57 (m, 2H), 3.45-3.36 (m, 6H), 3.34 (s, 3H), 3.20 (s, 1H), 2.85 (m, 2H), 2.81-2.75 (m, 2H), 2.37 (s, 3H), 1.98-1.93 (m, 2H), 1.69-1.65 (m, 2H);

MS m/z (ESI): 521.2 [M+H]$^+$.

N-(5-Cyano-4-((2-methoxyphenyl)amino)pyridin-2-yl)-7-formyl-6-((3-carbonylmorpholino) methyl)-3,4-dihydro-1,8-naphthyridin-1(2H)-carboxamide was prepared in accordance with the method of Example 1.

$^1$H NMR (400 MHz, CDCl$_3$) δ 13.62 (s, 1H), 10.23 (s, 1H), 8.30 (s, 1H), 8.06 (s, 1H), 7.65 (s, 1H), 7.50 (m, 1H), 7.17 (m, 1H), 7.07 (m, 1H), 6.98 (m, 1H), 6.90 (s, 1H), 5.10 (s, 2H), 4.25 (s, 2H), 4.08-4.00 (m, 2H), 3.88 (m, 5H), 3.44-3.37 (m, 2H), 2.91 (m, 2H), 2.04-1.96 (m, 2H);

MS m/z (ESI): 542.0 [M+H]$^+$.

71

Example 9

N-(5-Cyano-4-(((1-methoxycyclopropyl)methyl)amino)pyridin-2-yl)-7-formyl-6-((3-carbonylmorpholino) methyl)-3,4-dihydro-1,8-naphthyridin-1(2H)-carboxamide

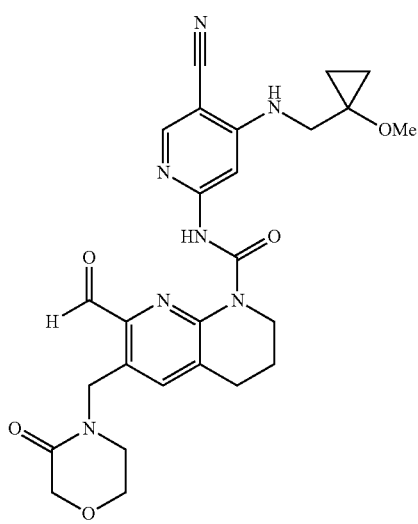 [SMILES: COC1(CNc2cc(NC(=O)N3CCCc4cc(CN5CCOCC5=O)c(C=O)nc43)ncc2C#N)CC1]

N-(5-Cyano-4-((1-methoxycyclopropyl)methyl)amino)pyridin-2-yl)-7-formyl-6-((3-carbonylmorpholino) methyl)-3,4-dihydro-1,8-naphthyridin-1(2H)-carboxamide was prepared in accordance with the method of Example 1.

$^1$H NMR (400 MHz, CDCl$_3$) δ 13.58 (s, 1H), 10.27 (s, 1H), 8.20 (s, 1H), 7.68 (s, 1H), 7.58 (s, 1H), 5.45 (s, 1H), 5.12 (s, 2H), 4.25 (s, 2H), 4.17-4.03 (m, 2H), 4.00-3.80 (m, 2H), 3.42 (t, J=5.0 Hz, 4H), 3.31 (s, 3H), 2.94 (t, J=6.2 Hz, 2H), 2.15-1.99 (m, 2H), 0.97 (m, 2H), 0.64 (m, 2H);

MS m/z (ESI): 520.2 [M+H]$^+$.

72

Example 10

N-(5-Cyano-4-((2-cyclopropoxyethyl)amino)pyridin-2-yl)-7-formyl-6-((3-carbonylmorpholino) methyl)-3,4-dihydro-1,8-naphthyridin-1(2H)-carboxamide

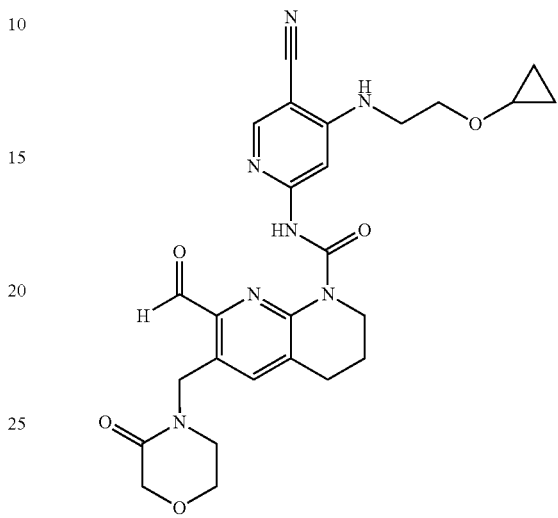

N-(5-Cyano-4-((2-cyclopropoxyethyl)amino)pyridin-2-yl)-7-formyl-6-((3-carbonylmorpholino) methyl)-3,4-dihydro-1,8-naphthyridin-1(2H)-carboxamide was prepared in accordance with the method of Example 1.

MS m/z (ESI): 520.2 [M+H]$^+$.

Example 11

N-(5-Cyano-4-((1-(methoxymethyl))cyclopropyl)amino)pyridin-2-yl)-7-formyl-6-((3-carbonylmorpholino) methyl)-3,4-dihydro-1,8-naphthyridin-1(2H)-carboxamide

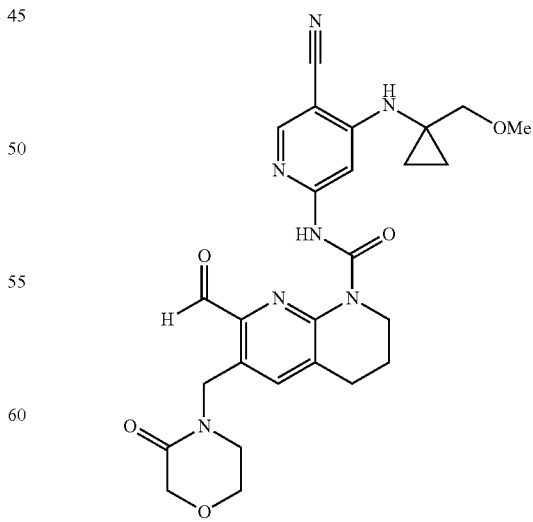

N-(5-Cyano-4-((1-(methoxymethyl))cyclopropyl)amino)pyridin-2-yl)-7-formyl-6-((3-carbonylmorpholino)methyl)-

3,4-dihydro-1,8-naphthyridin-1(2H)-carboxamide was prepared in accordance with the method of Example 1.

$^1$H NMR (400 MHz, CDCl$_3$) δ 13.53 (s, 1H), 10.18 (s, 1H), 8.12 (s, 1H), 7.84 (s, 1H), 7.60 (s, 1H), 5.59 (s, 1H), 5.04 (s, 2H), 4.19 (s, 2H), 4.03 (m, 2H), 3.82 (m, 2H), 3.41 (d, J=6.7 Hz, 2H), 3.35 (m, 2H), 3.28 (s, 3H), 2.87 (t, J=6.1 Hz, 2H), 1.98 (m, 2H), 0.98 (m, 2H), 0.91 (m, 2H);

MS m/z (ESI): 520.2 [M+H]$^+$.

Example 12

N-(5-Cyano-4-((2-(cyclopropylmethoxy)ethyl)amino)pyridin-2-yl)-7-formyl-6-((3-carbonylmorpholino)methyl)-3,4-dihydro-1,8-naphthyridin-1(2H)-carboxamide

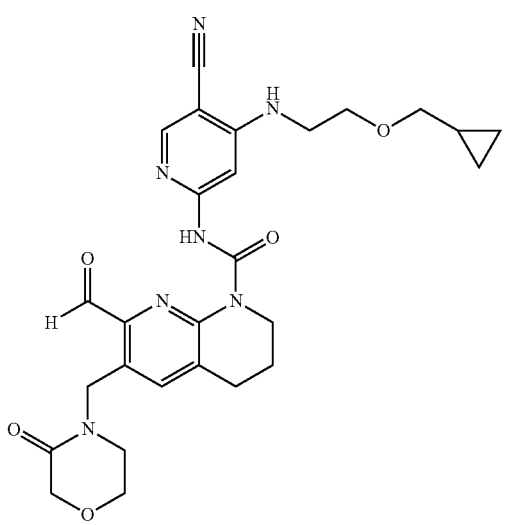 [SMILES: N#Cc1cnc(NC(=O)N2CCCc3cc(CN4CCOCC4=O)c(C=O)nc32)cc1NCCOCC1CC1]

N-(5-Cyano-4-((2-(cyclopropylmethoxy)ethyl)amino)pyridin-2-yl)-7-formyl-6-((3-carbonylmorpholino)methyl)-3,4-dihydro-1,8-naphthyridin-1(2H)-carboxamide was prepared in accordance with the method of Example 1.

MS m/z (ESI): 534.2 [M+H]$^+$.

Example 13

N-(5-Cyano-4-((2-methoxyethyl)thio)pyridin-2-yl)-7-formyl-6-((3-carbonylmorpholino) methyl)-3,4-dihydro-1,8-naphthyridin-1(2H)-carboxamide

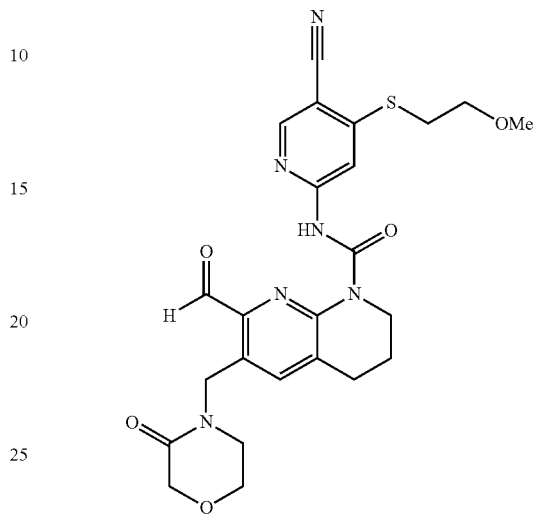

N-(5-Cyano-4-((2-methoxyethyl)thio)pyridin-2-yl)-7-formyl-6-((3-carbonylmorpholino) methyl)-3,4-dihydro-1,8-naphthyridin-1(2H)-carboxamide was prepared in accordance with the method of Example 1.

$^1$H NMR (400 MHz, CDCl$_3$) δ 13.87 (s, 1H), 10.23 (s, 1H), 8.35 (s, 1H), 8.27 (s, 1H), 7.69 (s, 1H), 5.11 (s, 2H), 4.26 (s, 2H), 4.11-4.08 (m, 2H), 3.91-3.88 (m, 2H), 3.77-3.74 (m, 2H), 3.46-3.39 (m, 5H), 3.36-3.32 (m, 2H), 2.93 (t, J=6.2 Hz, 2H), 2.10-2.02 (m, 2H);

MS m/z (ESI): 511.1 [M+H]$^+$.

Example 14

N-(5-Cyano-4-((tetrahydrofuran-3-yl)thio)pyridin-2-yl)-7-formyl-6-((3-carbonyl morpholino)methyl)-3,4-dihydro-1,8-naphthyridin-1(2H)-carboxamide

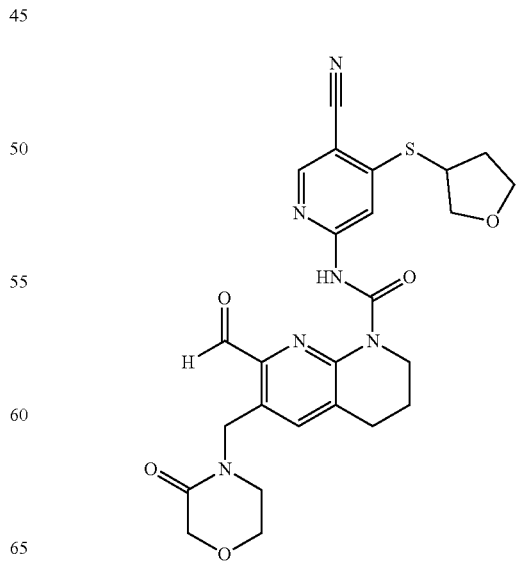

N-(5-Cyano-4-((tetrahydrofuran-3-yl)thio)pyridin-2-yl)-7-formyl-6-((3-carbonyl morpholino)methyl)-3,4-dihydro-1,8-naphthyridin-1(2H)-carboxamide was prepared in accordance with the method of Example 1.

¹H NMR (400 MHz, CDCl₃) δ 13.90 (s, 1H), 10.23 (s, 1H), 8.37 (s, 1H), 8.28 (s, 1H), 7.69 (s, 1H), 5.11 (s, 2H), 4.40-4.32 (m, 1H), 4.26 (s, 2H), 4.13-4.06 (m, 3H), 4.02-3.96 (m, 2H), 3.94-3.86 (m, 2H), 3.84-3.76 (m, 1H), 3.45-3.40 (m, 2H), 2.95 (t, J=6.2 Hz, 2H), 2.64-2.55 (m, 1H), 2.10-2.02 (m, 3H);

MS m/z (ESI): 523.1 [M+H]⁺.

Example 15

N-(5-Cyano-4-(((cis)-2-methoxycyclopentyl)amino)pyridin-2-yl)-7-formyl-6-((3-carbonylmorpholino)methyl)-3,4-dihydro-1,8-naphthyridin-1(2H)-carboxamide

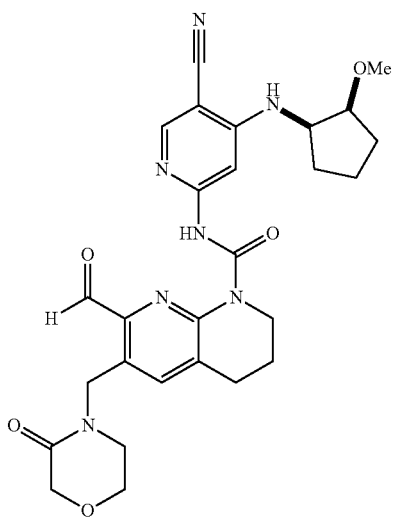

N-(5-Cyano-4-(((cis)-2-methoxycyclopentyl)amino)pyridin-2-yl)-7-formyl-6-((3-carbonylmorpholino)methyl)-3,4-dihydro-1,8-naphthyridin-1(2H)-carboxamide was prepared in accordance with the method of Example 1.

¹H NMR (400 MHz, CDCl₃): δ 13.53 (s, 1H), 10.24 (s, 1H), 8.16 (s, 1H), 7.67 (s, 1H), 7.56 (s, 1H), 5.87 (s, 1H), 5.11 (s, 2H), 4.25 (s, 2H), 4.08 (m, 2H), 3.88 (m, 3H), 3.86-3.79 (m, 1H), 3.45 (m, 2H), 3.38 (s, 3H), 2.93 (t, J=6.2 Hz, 2H), 2.30-2.18 (m, 1H), 2.10-2.00 (m, 3H), 1.94-1.77 (m, 3H), 1.65 (m, 2H);

MS m/z (ESI): 534.2 [M+H]⁺.

Example 16

N-(5-Cyano-4-(((trans)-2-methoxycyclopentyl)oxy)pyridin-2-yl)-7-formyl-6-((3-carbonylmorpholino)methyl)-3,4-dihydro-1,8-naphthyridin-1(2H)-carboxamide

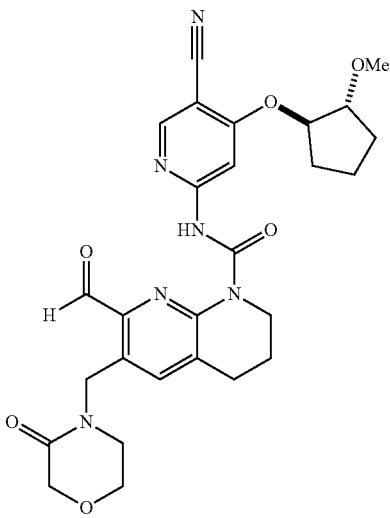

N-(5-Cyano-4-(((trans)-2-methoxycyclopentyl)oxy)pyridin-2-yl)-7-formyl-6-((3-carbonylmorpholino)methyl)-3,4-dihydro-1,8-naphthyridin-1(2H)-carboxamide was prepared in accordance with the method of Example 1.

¹H NMR (400 MHz, CDCl₃): δ 13.81 (s, 1H), 10.24 (s, 1H), 8.35 (s, 1H), 8.05 (s, 1H), 7.68 (s, 1H), 5.11 (s, 2H), 4.89-4.81 (m, 1H), 4.26 (s, 2H), 4.10 (m, 2H), 4.01-3.94 (m, 1H), 3.93-3.85 (m, 2H), 3.47-3.38 (m, 5H), 2.95 (t, J=6.2 Hz, 2H), 2.30-2.20 (m, 1H), 2.05 (m, 3H), 1.83 (m, 3H), 1.77-1.70 (m, 1H);

MS m/z (ESI): 535.2 [M+H]⁺.

Example 17

N-(5-Cyano-4-((1-methoxycyclopropyl)methoxy)pyridin-2-yl)-7-formyl-6-((3-carbonylmorpholino)methyl)-3,4-dihydro-1,8-naphthyridin-1(2H)-carboxamide

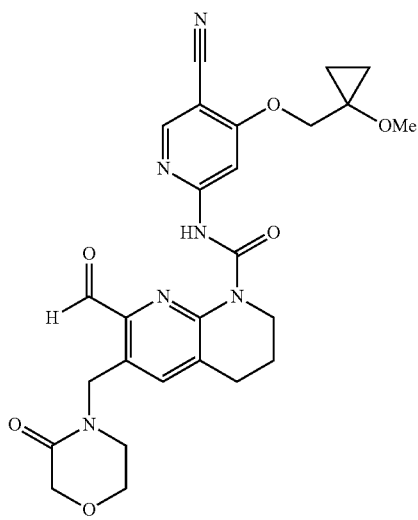 [SMILES: COC1(COc2cc(NC(=O)N3CCCc4cc(CN5CCOCC5=O)c(C=O)nc43)ncc2C#N)CC1]

N-(5-Cyano-4-((1-methoxycyclopropyl)methoxy)pyridin-2-yl)-7-formyl-6-((3-carbonylmorpholino) methyl)-3,4-dihydro-1,8-naphthyridin-1(2H)-carboxamide was prepared in accordance with the method of Example 1.

MS m/z (ESI): 521.2 [M+H]⁺.

Example 18

N-(5-Cyano-3-fluoro-4-((2-methoxyethyl)amino)pyridin-2-yl)-7-formyl-6-((3-carbonylmorpholino)methyl)-3,4-dihydro-1,8-naphthyridin-1(2H)-carboxamide

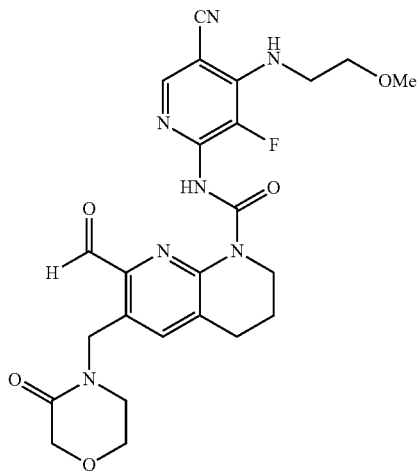 [SMILES: COCCNc1c(C#N)cnc(NC(=O)N2CCCc3cc(CN4CCOCC4=O)c(C=O)nc32)c1F]

N-(5-Cyano-3-fluoro-4-((2-methoxyethyl)amino)pyridin-2-yl)-7-formyl-6-((3-carbonylmorpholino) methyl)-3,4-dihydro-1,8-naphthyridin-1(2H)-carboxamide was prepared in accordance with the method of Example 1

MS m/z (ESI): 512.2 [M+H]⁺. .

Example 19

7-Formyl-N-(4-((2-methoxyethyl)amino)-5-cyanothiopyridin-2-yl)-6-((3-carbonylmorpholino) methyl)-3,4-dihydro-1,8-naphthyridin-1(2H)-carboxamide

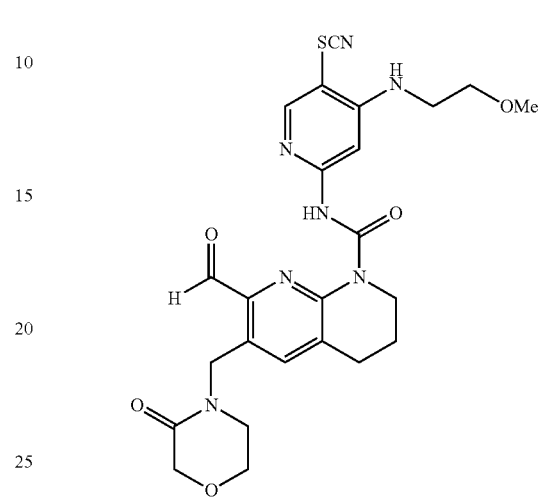

7-Formyl-N-(4-((2-methoxyethyl)amino)-5-cyanothiopyridin-2-yl)-6-((3-carbonylmorpholino) methyl)-3,4-dihydro-1,8-naphthyridin-1(2H)-carboxamide was prepared in accordance with the method of Example 1.

MS m/z (ESI): 526.1 [M+H]⁺.

Example 20

N-(5-Cyano-4-((2-methoxyethyl)amino)pyridin-2-yl)-7-formyl-6-((6-carbonyl-4-oxa-7-azaspiro[2.5]octane-7-yl)methyl)-3,4-dihydro-1,8-naphthyridin-1(2H)-carboxamide

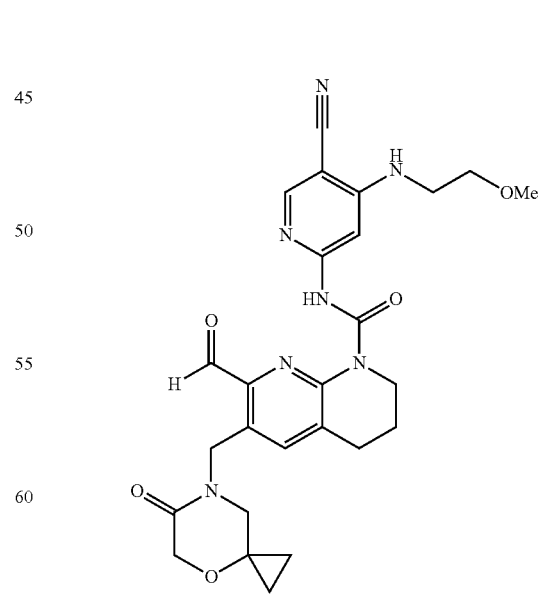

N-(5-Cyano-4-((2-methoxyethyl)amino)pyridin-2-yl)-7-formyl-6-((6-carbonyl-4-oxa -7-azaspiro[2.5]octane-7-yl)

methyl)-3,4-dihydro-1,8-naphthyridin-1(2H)-carboxamide was prepared in accordance with the method of Example 1.

MS m/z (ESI): 520.2 [M+H]⁺.

Example 21

N-(5-Cyano-4-((2-methoxyethyl)amino)pyridin-2-yl)-7-formyl-6-((5-carbonyl-7-oxa-4-azaspiro[2.5]octane-4-yl)methyl)-3,4-dihydro-1,8-naphthyridin-1(2H)-carboxamide

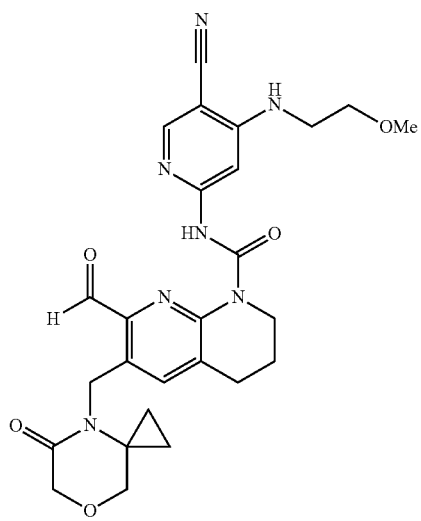 [SMILES: COCCNc1cc(NC(=O)N2CCCc3cc(CN4C(=O)COCC45CC5)c(C=O)nc32)ncc1C#N]

N-(5-Cyano-4-((2-methoxyethyl)amino)pyridin-2-yl)-7-formyl-6-((5-carbonyl-7-oxa-4-azaspiro[2.5]octane-4-yl)methyl)-3,4-dihydro-1,8-naphthyridin-1(2H)-carboxamide was prepared in accordance with the method of Example 1.

¹H NMR (400 MHz, CDCl₃) δ 13.53 (s, 1H), 10.22 (s, 1H), 8.17 (s, 1H), 7.56 (s, 1H), 7.42 (s, 1H), 4.86 (s, 2H), 4.47 (s, 2H), 4.10-4.07(m, 2H), 3.75 (s, 2H), 3.65-3.62 (m, 2H), 3.51-3.47 (m, 2H), 3.41 (s, 3H), 2.94 (t, J=6.2 Hz, 2H), 2.08-2.02 (m, 2H), 0.93-0.90 (m, 2H), 0.73-0.70 (m, 2H);

MS m/z (ESI): 520.2 [M+H]⁺.

Example 22

N-(5-Cyano-4-((2-methoxyethyl)amino)pyridin-2-yl)-7-formyl-6-((8-carbonyl-4-oxa-7-azaspiro[2.5]octane-7-yl)methyl)-3,4-dihydro-1,8-naphthyridin-1(2H)-carboxamide

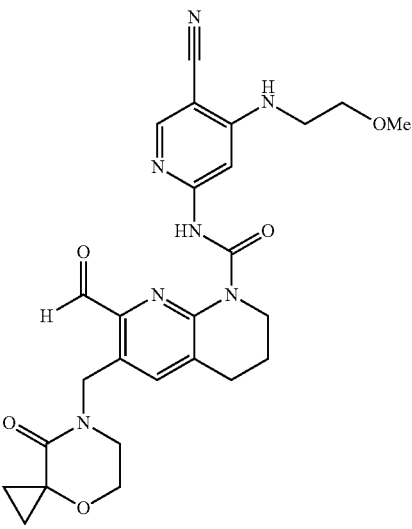 [SMILES: COCCNc1cc(NC(=O)N2CCCc3cc(CN4CCOC5(CC5)C4=O)c(C=O)nc32)ncc1C#N]

N-(5-Cyano-4-((2-methoxyethyl)amino)pyridin-2-yl)-7-formyl-6-((8-carbonyl-4-oxa-7-azaspiro[2.5]octane-7-yl)methyl)-3,4-dihydro-1,8-naphthyridin-1(2H)-carboxamide was prepared in accordance with the method of Example 1.

MS m/z (ESI): 520.2 [M+H]⁺.

Example 23

N-(5-Cyano-4-((2-methoxyethyl)amino)pyridin-2-yl)-7-formyl-6-((2-carbonyl-1,3-oxazepin-3-yl)methyl)-3,4-dihydro-1,8-naphthyridin-1(2H)-carboxamide

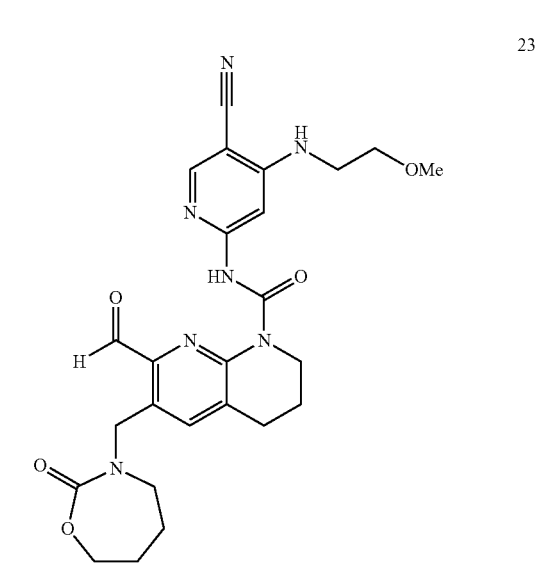 [SMILES: COCCNc1cc(NC(=O)N2CCCc3cc(CN4CCCCOC4=O)c(C=O)nc32)ncc1C#N]

Step 1: Preparation of N-(5-cyano-4-((2-methoxy-ethyl)amino)pyridin-2-yl)-7-(dimethoxymethyl)-6-((2-carbonyl-1,3-oxazepin-3-yl)methyl)-3,4-dihydro-1,8-naphthyridin-1(2H)-carboxamide Step 2: Preparation of N-(5-cyano-4-((2-methoxy-ethyl)amino)pyridin-2-yl)-7-formyl-6-((2-carbonyl-1,3-oxazepin-3-yl)methyl)-3,4-dihydro-1,8-naphthyridin-1(2H)-carboxamide

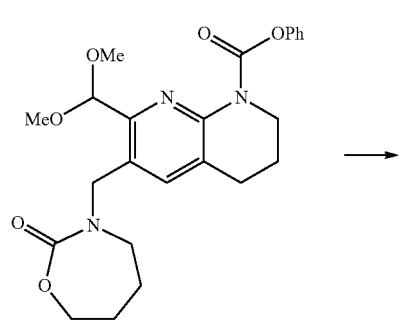

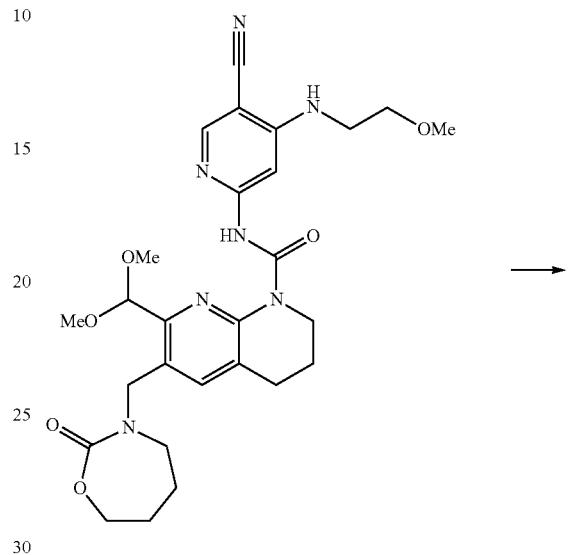

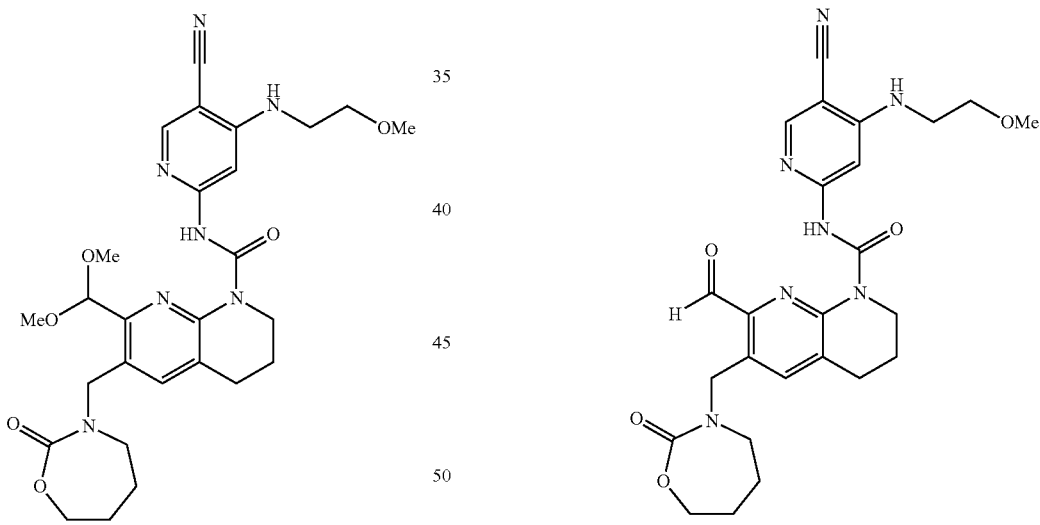

N-(5-Cyano-4-((2-methoxyethyl)amino)pyridin-2-yl)-7-(dimethoxymethyl)-6-((2-carbonyl-1,3-oxoheptyl-3-yl)methyl)-3,4-dihydro-1,8-naphthyridin-1(2H)-carboxamide was prepared in accordance with the method of Step 1 of Example 1.

MS m/z (ESI): 554.2 [M+H]$^+$.

N-(5-Cyano-4-((2-methoxyethyl)amino)pyridin-2-yl)-7-formyl-6-((2-carbonyl-1,3-oxazepin-3-yl)methyl)-3,4-dihydro-1,8-naphthyridin-1(2H)-carboxamide was prepared in accordance with the method of Step 2 of Example 1.

$^1$H NMR (400 MHz, CDCl$_3$) δ 13.60 (s, 1H), 10.25 (s, 1H), 8.18 (s, 1H), 7.71 (s, 1H), 7.59 (s, 1H), 5.37 (s, 1H), 4.95 (s, 2H), 4.16-4.14 (m, 2H), 4.09-4.06 (m, 2H), 3.66-3.63 (m, 2H), 3.52-3.48 (m, 2H), 3.42 (s, 3H), 3.32-3.29 (m, 2H), 2.94 (t, J=6.3 Hz, 2H), 2.10-1.96 (m, 2H), 1.95-1.83 (m, 2H), 1.77-1.69 (m, 2H);

MS m/z (ESI): 508.2 [M+H]$^+$.

Example 24

(S)-N-(5-Cyano-4-(((1-methoxycyclopropyl)methyl)amino)pyridin-2-yl)-7-formyl-6-((4-methyl-2-carbonyloxazolidin-3-yl)methyl)-3,4-dihydro-1,8-naphthyridin-1(2H)-carboxamide

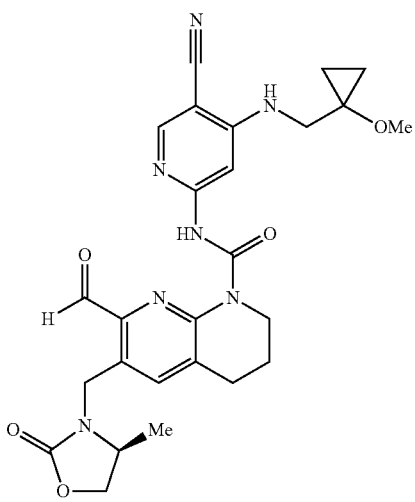 [SMILES: COC1(CNc2cc(NC(=O)N3CCCc4cc(CN5C(=O)OC[C@@H]5C)c(C=O)nc43)ncc2C#N)CC1]

(S)-N-(5-Cyano-4-(((1-methoxycyclopropyl)methyl)amino)pyridin-2-yl)-7-formyl-6-((4-methyl-2-carbonyloxazolidin-3-yl)methyl)-3,4-dihydro-1,8-naphthyridin-1(2H)-carboxamide was prepared in accordance with the method of Example 1.

MS m/z (ESI): 520.2 [M+H]+.

Example 25

N-(5-Cyano-4-(((1-methoxycyclopropyl)methyl)amino)pyridin-2-yl)-7-formyl-6-((3-carbonyl-1,4-oxazepin-4-yl)methyl)-3,4-dihydro-1,8-naphthyridin-1(2H)-carboxamide

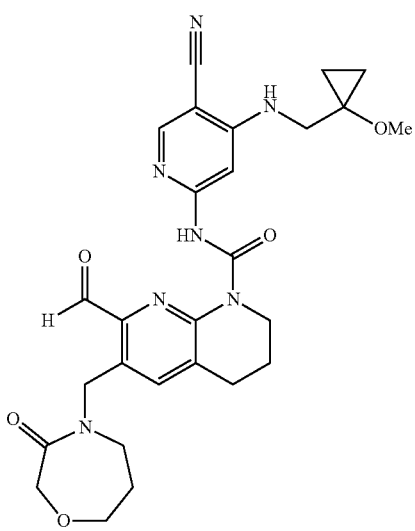 [SMILES: COC1(CNc2cc(NC(=O)N3CCCc4cc(CN5CCCOCC5=O)c(C=O)nc43)ncc2C#N)CC1]

N-(5-Cyano-4-(((1-methoxycyclopropyl)methyl)amino)pyridin-2-yl)-7-formyl-6-((3-carbonyl-1,4-oxazepin-4-yl)methyl)-3,4-dihydro-1,8-naphthyridin-1(2H)-carboxamide was prepared in accordance with the method of Example 1.

MS m/z (ESI): 534.2 [M+H]+.

Example 26

N-(5-Cyano-4-(3-methoxypyrrolidin-1-yl)pyridin-2-yl)-7-formyl-6-((3-carbonyl-1,4-oxazepin-4-yl)methyl)-3,4-dihydro-1,8-naphthyridin-1(2H)-carboxamide

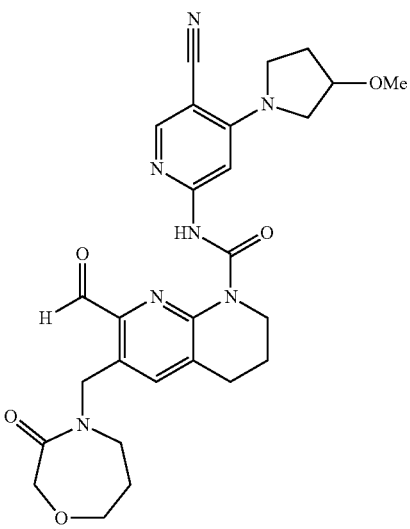 [SMILES: COC1CCN(c2cc(NC(=O)N3CCCc4cc(CN5CCCOCC5=O)c(C=O)nc43)ncc2C#N)C1]

N-(5-Cyano-4-(3-methoxypyrrolidin-1-yl)pyridin-2-yl)-7-formyl-6-((3-carbonyl-1,4-oxazepin-4-yl)methyl)-3,4-dihydro-1,8-naphthyridin-1(2H)-carboxamide was prepared in accordance with the method of Example 1.

MS m/z (ESI): 534.2 [M+H]+.

Example 27

N-(5-Cyano-4-(((trans)-2-methoxycyclopentyl) amino)pyridin-2-yl)-7-formyl-6-((3-carbonyl-1,4-oxazepin-4-yl)methyl)-3,4-dihydro-1,8-naphthyridin-1(2H)-carboxamide

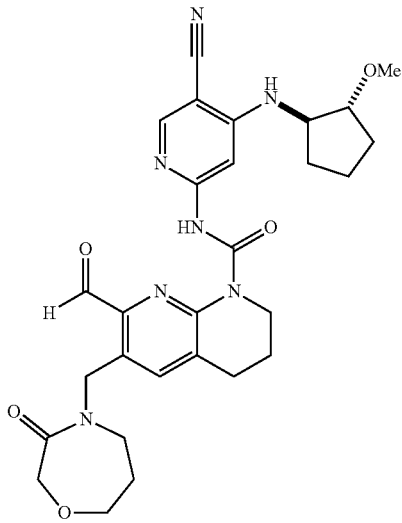

N-(5-Cyano-4-(((trans)-2-methoxycyclopentyl)amino) pyridin-2-yl)-7-formyl-6-((3-carbonyl-1,4-oxazepin-4-yl) methyl)-3,4-dihydro-1,8-naphthyridin-1(2H)-carboxamide was prepared in accordance with the method of Example 1.
MS m/z (ESI): 548.2 [M+H]$^+$.

Example 28

(R)-N-(5-Cyano-4-((1-methoxypropan-2-yl)oxy) pyridin-2-yl)-7-formyl-6-((3-carbonyl -1,4-oxazepin-4-yl)methyl)-3,4-dihydro-1,8-naphthyridin-1 (2H)-carboxamide

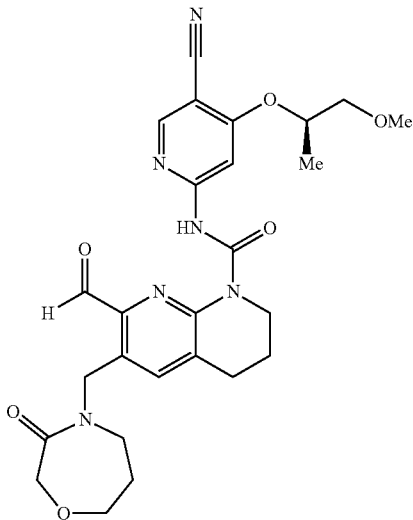 [SMILES: COC[C@@H](C)Oc1cc(NC(=O)N2CCCc3cc(CN4CCCOCC4=O)c(C=O)nc32)ncc1C#N]

(R)-N-(5-Cyano-4-((1-methoxypropan-2-yl)oxy)pyridin-2-yl)-7-formyl-6-((3-carbonyl -1,4-oxazepin-4-yl)methyl)-3,4-dihydro-1,8-naphthyridin-1(2H)-carboxamide was prepared in accordance with the method of Example 1.
MS m/z (ESI): 523.2 [M+H]$^+$.

Example 29

(R)-N-(5-Cyano-4-((1-methoxypropan-2-yl)amino) pyridin-2-yl)-7-formyl-6-((2-carbonyl-1,3-oxazepin-3-yl)methyl)-3,4-dihydro-1,8-naphthyridin-1(2H)-carboxamide

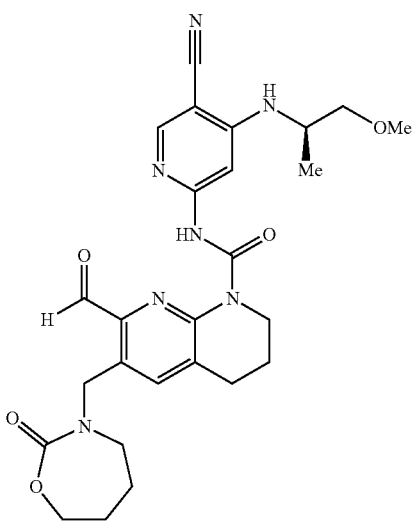

Step 1: Preparation of (R)-N-(5-cyano-4-((1-methoxypropan-2-yl)amino)pyridin-2-yl)-7-(dimethoxymethyl) -6-((2-carbonyl-1,3-oxazepin-3-yl) methyl)-3,4-dihydro-1,8-naphthyridin-1(2H)-carboxamide

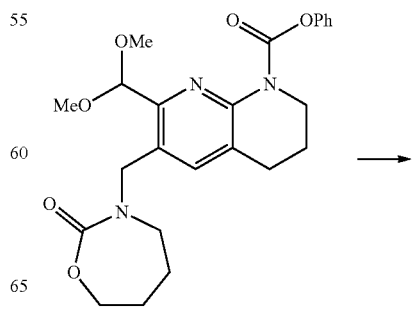

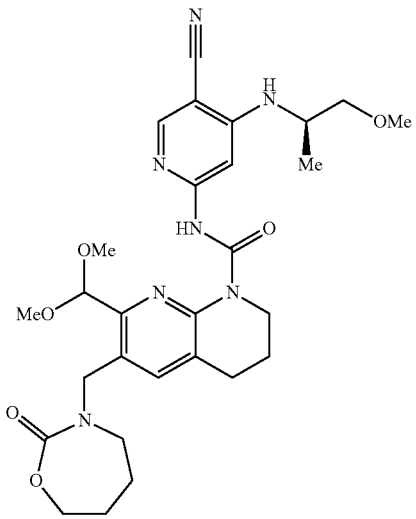

(R)-6-Amino-4-((1-methoxypropan-2-yl)amino)nicotinonitrile (30 mg, 0.14 mmol), and phenyl 7-(dimethoxymethyl)-6-((2-carbonyl-1,3-oxazepin-3-yl)methyl)-3,4-dihydro-1,8-naphthyridin -1(2H)-carboxylate (60 mg, 0.13 mmol) were dissolved in THF (5 mL). The mixture was cooled to −78° C. in a nitrogen atmosphere, followed by dropwise addition of a solution of LiHMDS in THF (0.3 mL, 0.3 mmol). The reaction solution was warmed up to room temperature naturally and stirred overnight. After addition of saturated aqueous NH$_4$Cl solution (50 mL), the mixture was extracted with ethyl acetate (50 mL×2). The organic phases were combined, washed with saturated brine, dried over anhydrous sodium sulfate and concentrated. The resulting residue was subjected to column chromatography to obtain the title compound (R)-N-(5-cyano-4-((1-methoxypropan-2-yl)amino)pyridin-2-yl)-7-(dimethoxymethyl) -6-((2-carbonyl-1,3-oxazepin-3-yl)methyl)-3,4-dihydro-1,8-naphthyridin-1(2H)-carboxamide (65 mg, 86%).

$^1$H NMR (400 MHz, CDCl$_3$) δ 13.70 (s, 1H), 8.18 (s, 1H), 7.60 (s, 2H), 5.41 (s, 1H), 5.12 (d, J=7.8 Hz, 1H), 4.73 (s, 2H), 4.20-4.11 (m, 2H), 4.06-3.99 (m, 2H), 3.93 (s, 1H), 3.52-3.48 (m, 7H), 3.46-3.42 (m, 1H), 3.39 (s, 3H), 3.26-3.21 (m, 2H), 2.83 (t, J=6.2 Hz, 2H), 2.03-1.95 (m, 2H), 1.91-1.83 (m, 2H), 1.67-1.62 (m, 2H), 1.31 (d, J=6.6 Hz, 3H);

MS m/z (ESI): 568.3 [M+H]$^+$.

Step 2: Preparation of (R)-N-(5-cyano-4-((1-methoxypropan-2-yl)amino)pyridin-2-yl)-7-formyl-6-((2-carbonyl -1,3-oxazepin-3-yl)methyl)-3,4-dihydro-1,8-naphthyridin-1(2H)-carboxamide

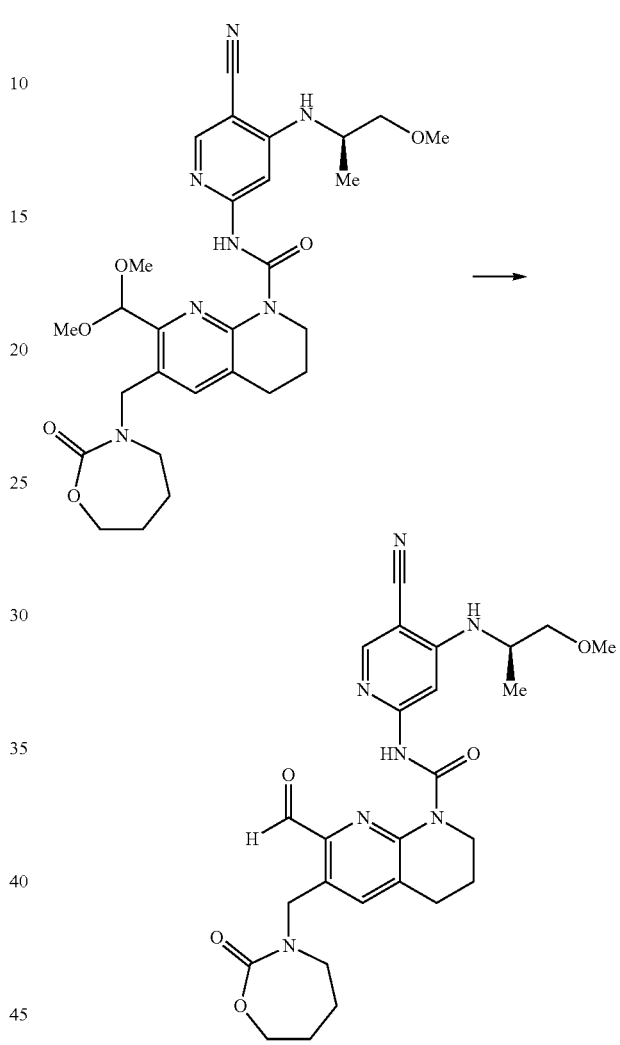

(R)-N-(5-Cyano-4-((1-methoxypropan-2-yl)amino)pyridin-2-yl)-7-(dimethoxym ethyl)-6-((2-carbonyl-1,3-oxazepin-3-yl)methyl)-3,4-dihydro-1,8-naphthyridin-1(2H) -carboxamide (65 mg, 0.12 mmol) was dissolved in a mixture of THF/water (volume ratio: 11/4, 4.5 mL), followed by addition of concentrated HCl (0.45 mL, 5.4 mmol). The mixture was stirred for 2 hours at room temperature. After addition of saturated aqueous NaHCO$_3$ solution (50 mL), the mixture was extracted with ethyl acetate (50 mL×2). The organic phases were combined, washed with saturated brine, dried over anhydrous sodium sulfate and concentrated. The resulting residue was subjected to column chromatography to obtain the title compound (R)-N-(5-cyano-4-((1-methoxypropan-2-yl)amino)pyridin-2-yl)-7-formyl-6-((2-carbonyl -1,3-oxazepin-3-yl)methyl)-3,4-dihydro-1,8-naphthyridin-1 (2H)-carboxamide (30 mg, 51%).

$^1$H NMR (400 MHz, CDCl$_3$) δ 13.57 (s, 1H), 10.26 (s, 1H), 8.17 (s, 1H), 7.71 (s, 1H), 7.63 (s, 1H), 5.27 (s, 1H), 4.95 (s, 2H), 4.19-4.12 (m, 2H), 4.11-4.04 (m, 2H), 3.94 (s,

1H), 3.52 (m, 1H), 3.48-3.37 (m, 4H), 3.33-3.28 (m, 2H), 2.93 (t, J=6.3 Hz, 2H), 2.04 (m, 2H), 1.93-1.85 (m, 2H), 1.73 (m, 2H), 1.39-1.28 (m, 3H);

MS m/z (ESI): 522.2 [M+H]+.

Example 30

(S)-N-(5-Cyano-4-((1-methoxypropan-2-yl)amino)pyridin-2-yl)-7-formyl-6-((2-carbonyl -1,3-oxazepin-3-yl)methyl)-3,4-dihydro-1,8-naphthyridin-1(2H)-carboxamide

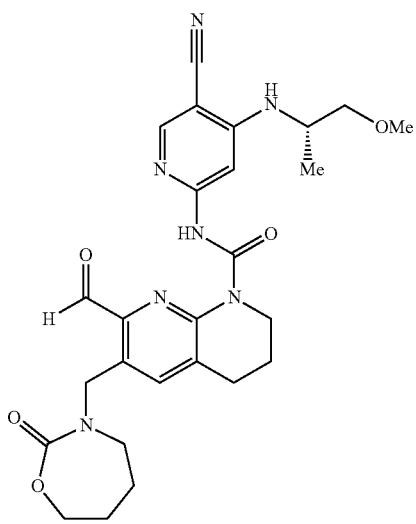 [SMILES: COC[C@H](C)Nc1cc(NC(=O)N2CCCc3cc(CN4CCCCOC4=O)c(C=O)nc32)ncc1C#N]

(S)-N-(5-Cyano-4-((1-methoxypropan-2-yl)amino)pyridin-2-yl)-7-formyl-6-((2-carbonyl -1,3-oxazepin-3-yl)methyl)-3,4-dihydro-1,8-naphthyridin-1(2H)-carboxamide was prepared in accordance with the method of Example 29.

1H NMR (400 MHz, CDCl3) δ 13.57 (s, 1H), 10.26 (s, 1H), 8.17 (s, 1H), 7.71 (s, 1H), 7.63 (s, 1H), 5.27 (s, 1H), 4.95 (s, 2H), 4.19-4.12 (m, 2H), 4.11-4.04 (m, 2H), 3.94 (s, 1H), 3.52 (m, 1H), 3.48-3.37 (m, 4H), 3.33-3.28 (m, 2H), 2.93 (t, J=6.3 Hz, 2H), 2.04 (m, 2H), 1.93-1.85 (m, 2H), 1.73 (m, 2H), 1.39-1.28 (m, 3H);

MS m/z (ESI): 522.2 [M+H]+.

Example 31

(R)-N-(5-Cyano-4-(3-methoxypyrrolidin-1-yl)pyridin-2-yl)-7-formyl-6-((2-carbonyl -1,3-oxazepin-3-yl)methyl)-3,4-dihydro-1,8-naphthyridin-1(2H)-carboxamide

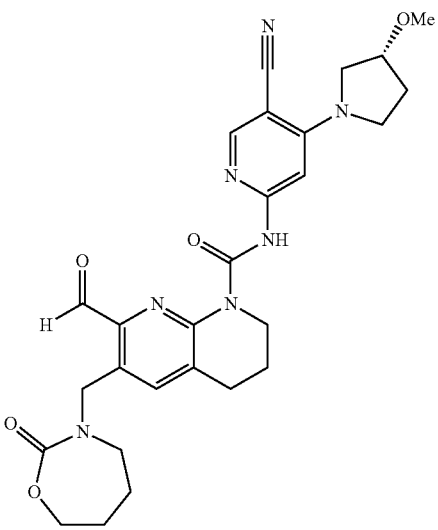 [SMILES: CO[C@@H]1CCN(c2cc(NC(=O)N3CCCc4cc(CN5CCCCOC5=O)c(C=O)nc43)ncc2C#N)C1]

(R)-N-(5-Cyano-4-(3-methoxypyrrolidin-1-yl)pyridin-2-yl)-7-formyl-6-((2-carbonyl -1,3-oxazepin-3-yl)methyl)-3,4-dihydro-1,8-naphthyridin-1(2H)-carboxamide was prepared in accordance with the method of Example 29.

1H NMR (400 MHz, CDCl3) δ 13.52 (s, 1H), 10.29 (s, 1H), 8.21 (s, 1H), 7.71 (s, 1H), 7.53 (d, J=8.0 Hz, 1H), 4.95 (s, 2H), 4.17-4.04 (m, 5H), 3.90-3.78 (m, 4H), 3.37 (s, 3H), 3.34-3.27 (m, 2H), 2.93 (t, J=6.3 Hz, 2H), 2.25 (m, 1H), 2.09-2.00 (m, 3H), 1.88 (m, 2H), 1.77-1.68 (m, 2H);

MS m/z (ESI): 534.2 [M+H]+.

Example 32

(S)-N-(5-Cyano-4-(3-methoxypyrrolidin-1-yl)pyridin-2-yl)-7-formyl-6-((2-carbonyl-1,3-oxazepin-3-yl)methyl)-3,4-dihydro-1,8-naphthyridin-1(2H)-carboxamide

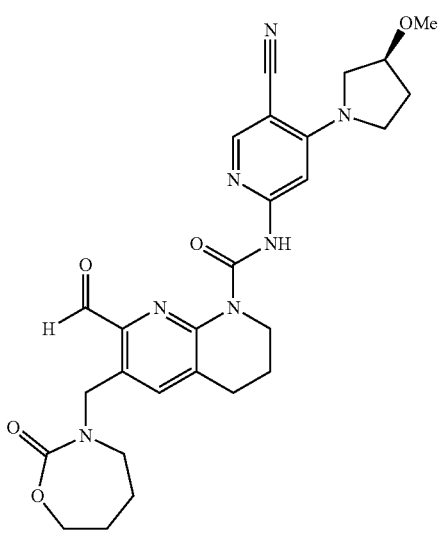 [SMILES: CO[C@H]1CCN(c2cc(NC(=O)N3CCCc4cc(CN5CCCCOC5=O)c(C=O)nc43)ncc2C#N)C1]

(S)-N-(5-Cyano-4-(3-methoxypyrrolidin-1-yl)pyridin-2-yl)-7-formyl-6-((2-carbonyl-1,3-oxazepin-3-yl)methyl)-3,4-dihydro-1,8-naphthyridin-1(2H)-carboxamide was prepared in accordance with the method of Example 29.

$^1$H NMR (400 MHz, CDCl$_3$) δ 13.52 (s, 1H), 10.29 (s, 1H), 8.21 (s, 1H), 7.71 (s, 1H), 7.53 (d, J=8.0 Hz, 1H), 4.95 (s, 2H), 4.17-4.04 (m, 5H), 3.90-3.78 (m, 4H), 3.37 (s, 3H), 3.34-3.27 (m, 2H), 2.93 (t, J=6.3 Hz, 2H), 2.25 (m, 1H), 2.09-2.00 (m, 3H), 1.88 (m, 2H), 1.77-1.68 (m, 2H);

MS m/z (ESI): 534.2 [M+H]$^+$.

Example 33

(S)-N-(5-Cyano-4-((tetrahydrofuran-3-yl)amino)pyridin-2-yl)-7-formyl-6-((2-carbonyl-1,3-oxazepin-3-yl)methyl)-3,4-dihydro-1,8-naphthyridin-1(2H)-carboxamide

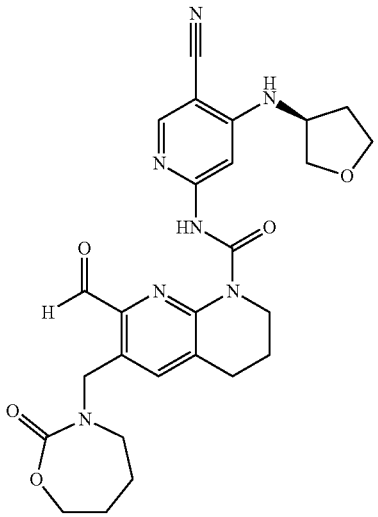 [SMILES: N#Cc1cnc(NC(=O)N2CCCc3cc(CN4CCCCOC4=O)c(C=O)nc32)cc1N[C@H]1CCOC1]

(S)-N-(5-Cyano-4-((tetrahydrofuran-3-yl)amino)pyridin-2-yl)-7-formyl-6-((2-carbonyl-1,3-oxazepin-3-yl)methyl)-3,4-dihydro-1,8-naphthyridin-1(2H)-carboxamide was prepared in accordance with the method of Example 29.

$^1$H NMR (400 MHz, CDCl$_3$): δ 13.66 (s, 1H), 10.26 (s, 1H), 8.20 (s, 1H), 7.72 (s, 1H), 7.64 (s, 1H), 5.13 (s, 1H), 4.95 (s, 2H), 4.35-4.27 (m, 1H), 4.19-4.13 (m, 2H), 4.12-4.06 (m, 2H), 4.07-3.98 (m, 1H), 3.89 (m, 1H), 3.81 (m, 1H), 3.35-3.28 (m, 2H), 2.94 (t, J=6.3 Hz, 2H), 2.44 (m, 1H), 2.05 (m, 2H), 2.00-1.94 (m, 1H), 1.89 (m, 2H), 1.77-1.69 (m, 2H);

MS m/z (ESI): 520.2 [M+H]$^+$.

93

Example 34

(R)-N-(5-Cyano-4-((tetrahydrofuran-3-yl)amino)pyridin-2-yl)-7-formyl-6-((2-carbonyl-1,3-oxazepin-3-yl)methyl)-3,4-dihydro-1,8-naphthyridin-1(2H)-carboxamide

94

Example 35

(R)-N-(5-Cyano-4-((1-methoxypropan-2-yl)oxy)pyridin-2-yl)-7-formyl-6-((2-carbonyl -1,3-oxazepin-3-yl)methyl)-3,4-dihydro-1,8-naphthyridin-1(2H)-carboxamide

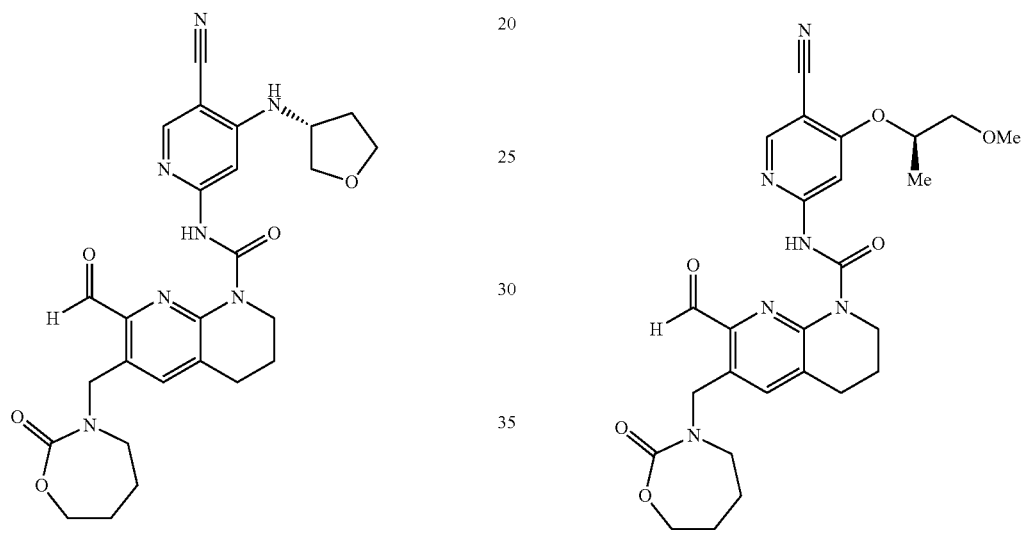

(R)-N-(5-Cyano-4-((tetrahydrofuran-3-yl)amino)pyridin-2-yl)-7-formyl-6-((2-carbonyl -1,3-oxazepin-3-yl)methyl)-3,4-dihydro-1,8-naphthyridin-1(2H)-carboxamide was prepared in accordance with the method of Example 29.

$^1$H NMR (400 MHz, CDCl$_3$): δ 13.66 (s, 1H), 10.26 (s, 1H), 8.20 (s, 1H), 7.72 (s, 1H), 7.64 (s, 1H), 5.13 (s, 1H), 4.95 (s, 2H), 4.35-4.27 (m, 1H), 4.19-4.13 (m, 2H), 4.12-4.06 (m, 2H), 4.07-3.98 (m, 2H), 3.89 (m, 1H), 3.81 (m, 1H), 3.35-3.28 (m, 2H), 2.94 (t, J=6.3 Hz, 2H), 2.44 (m, 1H), 2.05 (m, 2H), 2.00-1.94 (m, 1H), 1.89 (m, 2H), 1.77-1.69 (m, 2H);

MS m/z (ESI): 520.2 [M+H]$^+$.

((R)-N-(5-Cyano-4-((1-methoxypropan-2-yl)oxy)pyridin-2-yl)-7-formyl-6-((2-carbonyl -1,3-oxazepin-3-yl)methyl)-3,4-dihydro-1,8-naphthyridin-1(2H)-carboxamide was prepared in accordance with the method of Example 29.

$^1$H NMR (400 MHz, CDCl$_3$) δ 13.86 (s, 1H), 10.27 (s, 1H), 8.36 (s, 1H), 8.06 (s, 1H), 7.73 (s, 1H), 4.95 (s, 2H), 4.92-4.86 (m, 1H), 4.18-4.13 (m, 2H), 4.11-4.05 (m, 2H), 3.67 (m, 1H), 3.58 (m, 1H), 3.43 (s, 3H), 3.35-3.29 (m, 2H), 2.94 (t, J=6.3 Hz, 2H), 2.09-2.02 (m, 2H), 1.93-1.86 (m, 2H), 1.74 (m, 2H), 1.42 (d, J=6.3 Hz, 3H);

MS m/z (ESI): 523.2 [M+H]$^+$.

Example 36

(S)-N-(5-Cyano-4-((tetrahydrofuran-2-yl)thio)pyridin-2-yl)-7-formyl-6-((2-carbonyl-1,3-oxazepin-3-yl)methyl)-3,4-dihydro-1,8-naphthyridin-1(2H)-carboxamide

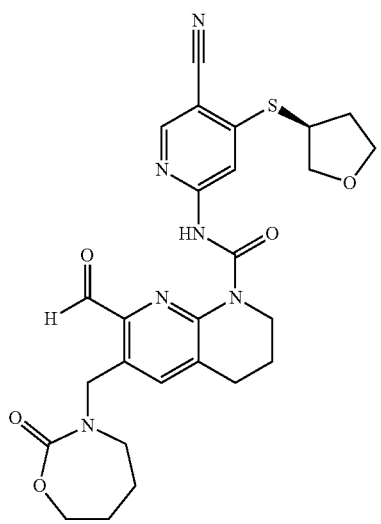 [SMILES: N#Cc1cnc(NC(=O)N2CCCc3cc(CN4CCCCOC4=O)c(C=O)nc32)cc1S[C@H]1CCOC1]

(S)-N-(5-Cyano-4-((tetrahydrofuran-2-yl)thio)pyridin-2-yl)-7-formyl-6-((2-carbonyl-1,3-oxazepin-3-yl)methyl)-3,4-dihydro-1,8-naphthyridin-1(2H)-carboxamide was prepared in accordance with the method of Example 29.

$^1$H NMR (400 MHz, CDCl$_3$) δ 13.95 (s, 1H), 10.25 (s, 1H), 8.38 (s, 1H), 8.32 (s, 1H), 7.73 (s, 1H), 4.95 (s, 2H), 4.38 (m, 1H), 4.19-4.06 (m, 5H), 4.04-3.93 (m, 2H), 3.81 (m, 1H), 3.35-3.28 (m, 2H), 2.95 (t, J=6.1 Hz, 2H), 2.60 (m, 1H), 2.09-2.03 (m, 3H), 1.92-1.88 (m, 2H), 1.74 (m, 2H);

MS m/z (ESI): 537.2 [M+H]$^+$.

Example 37

N-(5-Cyano-4-(((trans)-4-methoxytetrahydrofuran-3-yl)amino)pyridin-2-yl)-7-formyl-6-((2-carbonyl-1,3-oxazepin-3-yl)methyl)-3,4-dihydro-1,8-naphthyridin-1(2H)-carboxamide

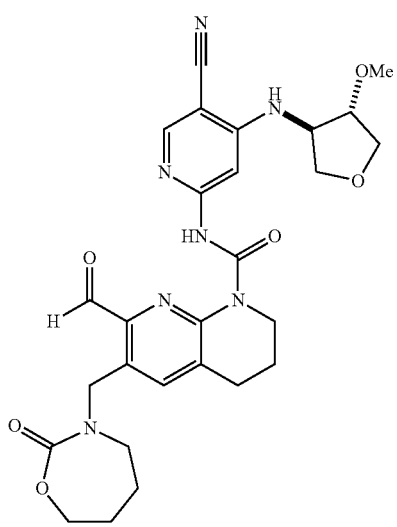

N-(5-Cyano-4-(((trans)-4-methoxytetrahydrofuran-3-yl)amino)pyridin-2-yl)-7-formyl-6-((2-carbonyl-1,3-oxazepin-3-yl)methyl)-3,4-dihydro-1,8-naphthyridin-1(2H)-carboxamide was prepared in accordance with the method of Example 29.

$^1$H NMR (400 MHz, CDCl$_3$) δ 13.66 (s, 1H), 10.23 (s, 1H), 8.21 (s, 1H), 7.78 (s, 1H), 7.71 (s, 1H), 5.02-4.92 (m, 3H), 4.17-4.07 (m, 7H), 3.92-3.89 (m, 1H), 3.86-3.79 (m, 2H), 3.54 (s, 3H), 3.34-3.28 (m, 2H), 2.94 (t, J=6.3 Hz, 2H), 2.05-2.02 (m, 2H), 1.93-1.85 (m, 2H), 1.76-1.70 (m, 2H);

MS m/z (ESI): 550.2 [M+H]$^+$.

Example 38

N-(5-Cyano-4-((R)-3-methoxypyrrolidin-1-yl)pyridin-2-yl)-7-formyl-6-(((S)-4-methyl-2-carbonyloxazolidin-3-yl)methyl)-3,4-dihydro-1,8-naphthyridin-1(2H)-carboxamide

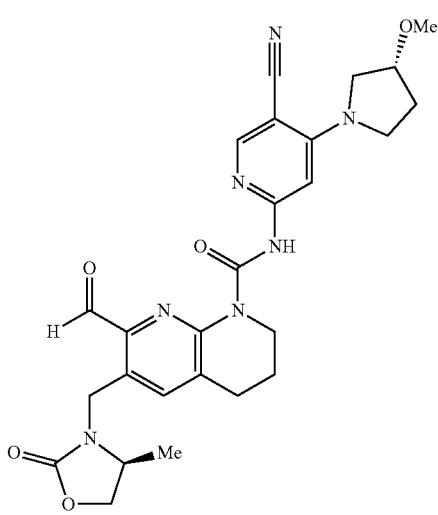 [SMILES: CO[C@@H]1CCN(c2cc(NC(=O)N3CCCc4cc(CN5C(=O)OC[C@@H]5C)c(C=O)nc43)ncc2C#N)C1]

N-(5-Cyano-4-((R)-3-methoxypyrrolidin-1-yl)pyridin-2-yl)-7-formyl-6-(((S)-4-methyl-2-carbonyloxazolidin-3-yl)methyl)-3,4-dihydro-1,8-naphthyridin-1(2H)-carboxamide was prepared in accordance with the method of Example 29.

$^1$H NMR (400 MHz, CDCl$_3$) δ 13.49 (s, 1H), 10.24 (s, 1H), 8.21 (s, 1H), 7.76 (s, 1H), 7.48 (s, 1H), 5.05 (d, J=16.2 Hz, 1H), 4.79 (d, J=16.2 Hz, 1H), 4.42 (t, J=8.3 Hz, 1H), 4.09 (m, 3H), 3.91 (m, 1H), 3.88-3.77 (m, 5H), 3.37 (s, 3H), 2.93 (t, J=6.3 Hz, 2H), 2.23 (m, 1H), 2.07-2.00 (m, 3H), 1.29 (d, J=6.0 Hz, 3H);

MS m/z (ESI): 520.2 [M+H]$^+$.

Example 39

N-(5-Cyano-4-((S)-3-methoxypyrrolidin-1-yl)pyridin-2-yl)-7-formyl-6-(((S)-4-methyl-2-carbonyloxazolidin-3-yl)methyl)-3,4-dihydro-1,8-naphthyridin-1(2H)-carboxamide

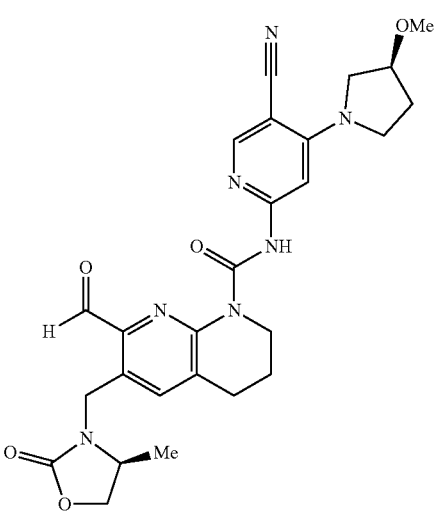 [SMILES: CO[C@H]1CCN(c2cc(NC(=O)N3CCCc4cc(CN5C(=O)OC[C@@H]5C)c(C=O)nc43)ncc2C#N)C1]

N-(5-Cyano-4-((S)-3-methoxypyrrolidin-1-yl)pyridin-2-yl)-7-formyl-6-(((S)-4-methyl-2-carbonyloxazolidin-3-yl)methyl)-3,4-dihydro-1,8-naphthyridin-1(2H)-carboxamide was prepared in accordance with the method of Example 29.

$^1$H NMR (400 MHz, CDCl$_3$) δ 13.48 (s, 1H), 10.25 (s, 1H), 8.21 (s, 1H), 7.77 (s, 1H), 7.50 (s, 1H), 5.06 (d, J=16.2 Hz, 1H), 4.79 (d, J=16.2 Hz, 1H), 4.41 (t, J=8.2 Hz, 1H), 4.11-4.04 (m, 3H), 3.88 (m, 6H), 3.37 (s, 3H), 2.93 (t, J=6.3 Hz, 2H), 2.24 (m, 1H), 2.09-2.00 (m, 3H), 1.29 (d, J=6.0 Hz, 3H);

MS m/z (ESI): 520.2 [M+H]$^+$.

Example 40

(S)-N-(5-Cyano-4-(3-methoxypyrrolidin-1-yl)pyridin-2-yl)-7-formyl-6-((2-carbonyloxazolidin-3-yl)methyl)-3,4-dihydro-1,8-naphthyridin-1(2H)-carboxamide

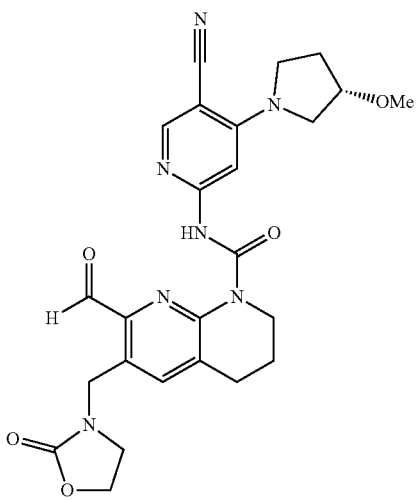 [SMILES: CO[C@H]1CCN(c2cc(NC(=O)N3CCCc4cc(CN5CCOC5=O)c(C=O)nc43)ncc2C#N)C1]

(S)-N-(5-Cyano-4-(3-methoxypyrrolidin-1-yl)pyridin-2-yl)-7-formyl-6-((2-carbonyloxazolidin-3-yl)methyl)-3,4-dihydro-1,8-naphthyridin-1(2H)-carboxamide was prepared in accordance with the method of Example 29.

$^1$H NMR (400 MHz, CDCl$_3$) δ 13.55 (s, 1H), 10.21 (s, 1H), 8.18 (s, 1H), 7.74 (s, 1H), 7.46 (s, 1H), 4.87 (s, 2H), 4.35-4.31 (m, 2H), 4.09-4.06 (m, 3H), 3.73-3.54 (m, 4H), 3.59 (t, J=7.9 Hz, 2H), 3.37 (s, 3H), 2.94 (t, J=6.0 Hz, 2H), 2.31-2.12 (m, 1H), 2.12-1.86 (m, 3H);

MS m/z (ESI): 506.2 [M+H]$^+$.

Example 41

(R)-N-(5-Cyano-4-(3-methoxypyrrolidin-1-yl)pyridin-2-yl)-7-formyl-6-((2-carbonyloxazolidin-3-yl)methyl)-3,4-dihydro-1,8-naphthyridin-1(2H)-carboxamide

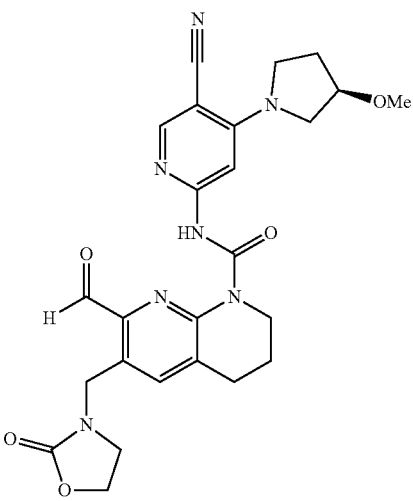 [SMILES: CO[C@@H]1CCN(c2cc(NC(=O)N3CCCc4cc(CN5CCOC5=O)c(C=O)nc43)ncc2C#N)C1]

(R)-N-(5-Cyano-4-(3-methoxypyrrolidin-1-yl)pyridin-2-yl)-7-formyl-6-((2-carbonyloxazolidin-3-yl)methyl)-3,4-dihydro-1,8-naphthyridin-1(2H)-carboxamide was prepared in accordance with the method of Example 29.

$^1$H NMR (400 MHz, CDCl$_3$) δ 13.55 (s, 1H), 10.21 (s, 1H), 8.18 (s, 1H), 7.74 (s, 1H), 7.46 (s, 1H), 4.87 (s, 2H), 4.35-4.31 (m, 2H), 4.09-4.06 (m, 3H), 3.73-3.54 (m, 4H), 3.59 (t, J=7.9 Hz, 2H), 3.37 (s, 3H), 2.94 (t, J=6.0 Hz, 2H), 2.31-2.12 (m, 1H), 2.12-1.86 (m, 3H);

MS m/z (ESI): 506.2 [M+H]$^+$.

Example 42

(R)-N-(5-Cyano-4-((1-methoxypropan-2-yl)oxy)pyridin-2-yl)-7-formyl-6-((5-carbonyl-6-oxa-4-azaspiro[2.4]heptan-4-yl)methyl)-3,4-dihydro-1,8-naphthyridin-1(2H)-carboxamide

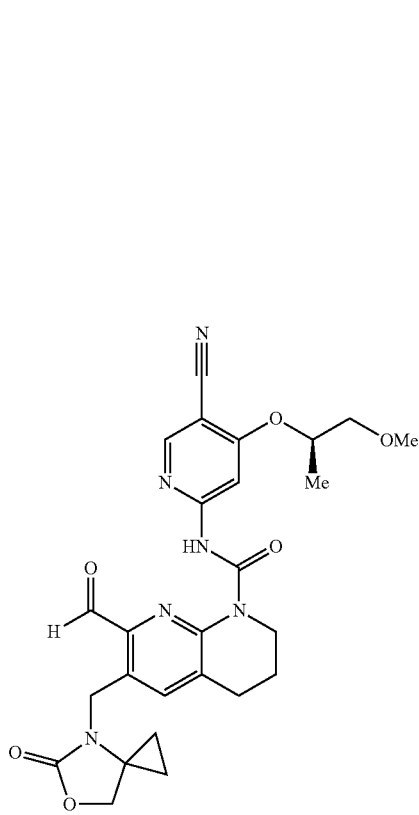 [SMILES: COC[C@@H](C)Oc1cc(NC(=O)N2CCCc3cc(CN4C(=O)OCC45CC5)c(C=O)nc32)ncc1C#N]

(R)-N-(5-Cyano-4-((1-methoxypropan-2-yl)oxy)pyridin-2-yl)-7-formyl-6-((5-carbonyl -6-oxa-4-azaspiro[2.4]heptan-4-yl)methyl)-3,4-dihydro-1,8-naphthyridin-1(2H) -carboxamide was prepared in accordance with the method of Example 29.

$^1$H NMR (400 MHz, CDCl$_3$) δ 13.76 (s, 1H), 10.21 (s, 1H), 8.34 (s, 1H), 8.01 (s, 1H), 7.70 (s, 1H), 4.89-4.85 (m, 1H), 4.70 (s, 2H), 4.39 (s, 2H), 4.11-4.08 (m, 2H), 3.69-3.64 (m, 1H), 3.60-3.56 (m, 1H), 3.43 (s, 3H), 2.97 (t, J=6.2 Hz, 2H), 2.07-2.05 (m, 2H), 1.42-1.41 (m, 3H), 0.97-0.94 (m, 2H), 0.66-0.62 (m, 2H);

MS m/z (ESI): 521.2 [M+H]$^+$.

Example 43

N-(5-Cyano-4-((2-methoxyethyl)amino)pyridin-2-yl)-7-formyl-6-((5-carbonyl-6-oxa -4-azaspiro[2.4]heptan-4-yl)methyl)-3,4-dihydro-1,8-naphthyridin-1(2H)-carboxamide

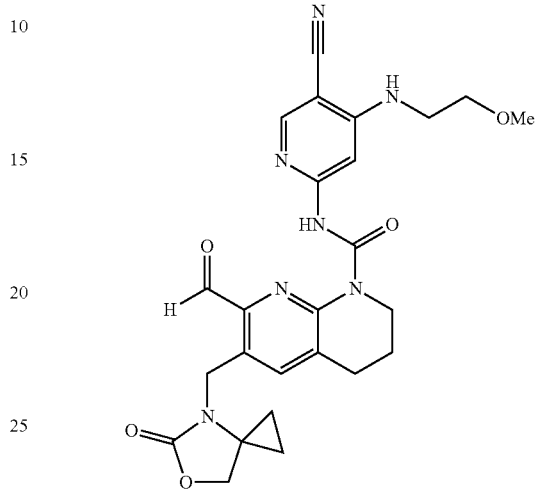

N-(5-Cyano-4-((2-methoxyethyl)amino)pyridin-2-yl)-7-formyl-6-((5-carbonyl-6-oxa-4-azaspiro[2.4]heptan-4-yl) methyl)-3,4-dihydro-1,8-naphthyridin-1(2H)-carboxamide was prepared in accordance with the method of Example 29.

$^1$H NMR (400 MHz, CDCl$_3$) δ 13.46 (s, 1H), 10.14 (s, 1H), 8.10 (s, 1H), 7.62 (s, 1H), 7.50 (s, 1H), 4.63 (s, 2H), 4.32 (s, 2H), 4.01 (m, 2H), 3.57-3.34 (m, 8H), 2.88 (m, 2H), 1.98 (m, 2H), 0.88 (m, 2H), 0.56 (m, 2H);

MS m/z (ESI): 506.2 [M+H]$^+$.

Example 44

N-(5-Cyano-4-(((R)-tetrahydrofuran-3-yl)thio)pyridin-2-yl)-7-formyl-6-(((S)-4-methyl-2-carbonyloxazolidin-3-yl)methyl)-3,4-dihydro-1,8-naphthyridin-1(2H)-carboxamide

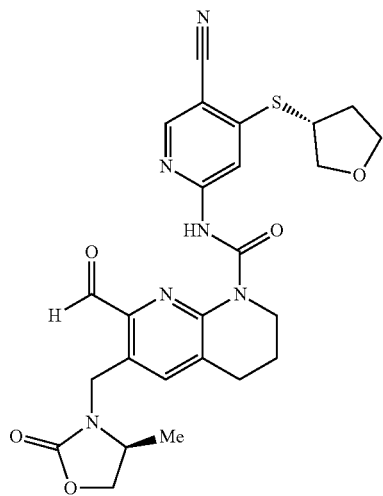

N-(5-Cyano-4-(((R)-tetrahydrofuran-3-yl)thio)pyridin-2-yl)-7-formyl-6-(((S)-4-methyl-2-carbonyloxazolidin-3-yl)methyl)-3,4-dihydro-1,8-naphthyridin-1(2H)-carboxamide was prepared in accordance with the method of Example 29.

$^1$H NMR (400 MHz, CDCl$_3$) δ 13.90 (s, 1H), 10.23 (s, 1H), 8.37 (s, 1H), 8.28 (s, 1H), 7.79 (s, 1H), 5.05 (d, J=16.4 Hz, 1H), 4.80 (d, J=16.4 Hz, 1H), 4.35 (m, 2H), 4.09 (m, 3H), 3.85 (m, 5H), 2.95 (m, 2H), 2.59 (m, 1H), 2.06 (m, 3H), 1.28 (m, 3H);

MS m/z (ESI): 523.1 [M+H]$^+$.

Example 45

N-(5-Cyano-4-(((S)-tetrahydrofuran-3-yl)thio)pyridin-2-yl)-7-formyl-6-(((S)-4-methyl-2-carbonyloxazolidin-3-yl)methyl)-3,4-dihydro-1,8-naphthyridin-1(2H)-carboxamide

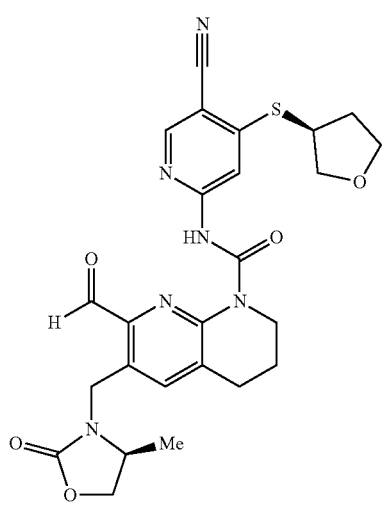 [SMILES: C[C@H]1COC(=O)N1Cc1cc2c(nc1C=O)N(C(=O)Nc1cc(S[C@H]3CCOC3)c(C#N)cn1)CCC2]

N-(5-Cyano-4-(((S)-tetrahydrofuran-3-yl)thio)pyridin-2-yl)-7-formyl-6-(((S)-4-methyl-2-carbonyloxazolidin-3-yl)methyl)-3,4-dihydro-1, 8-naphthyridin-1(2H)-carboxamide was prepared in accordance with the method of Example 29.

$^1$H NMR (400 MHz, CDCl$_3$) δ 13.90 (s, 1H), 10.23 (s, 1H), 8.37 (s, 1H), 8.28 (s, 1H), 7.79 (s, 1H), 5.05 (d, J=16.4 Hz, 1H), 4.80 (d, J=16.4 Hz, 1H), 4.35 (m, 2H), 4.09 (m, 3H), 3.85 (m, 5H), 2.95 (m, 2H), 2.59 (m, 1H), 2.06 (m, 3H), 1.28 (m, 3H);

MS m/z (ESI): 523.1 [M+H]$^+$.

Example 46

N-(5-Cyano-4-trans-(((3,4)-4-methoxytetrahydrofuran-3-yl)amino)pyridin-2-yl) -7-formyl-6-(((S)-4-methyl-2-carbonyloxazolidin-3-yl)methyl)-3,4-dihydro-1,8-naphthyridin -1(2H)-carboxamide

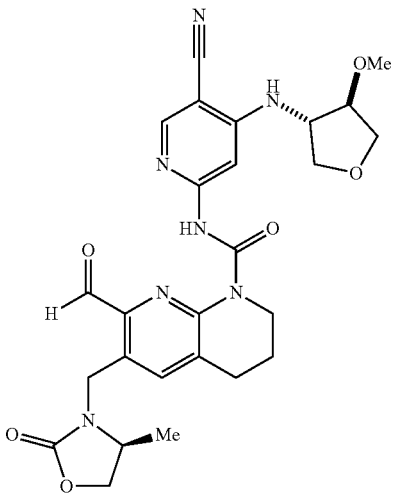

N-(5-Cyano-4-trans-(((3,4)-4-methoxytetrahydrofuran-3-yl)amino)pyridin-2-yl) -7-formyl-6-(((S)-4-methyl-2-carbonyloxazolidin-3-yl)methyl)-3,4-dihydro-1,8-naphthyridin -1(2H)-carboxamide was prepared in accordance with the method of Example 29.

$^1$H NMR (400 MHz, CDCl$_3$): δ 13.64 (s, 1H), 10.24 (s, 1H), 8.21 (s, 1H), 7.78 (d, J=4.1 Hz, 2H), 5.01 (m, 1H), 4.79 (m, 1H), 4.51 (m, 1H), 4.43 (m, 1H), 4.14 (m, 2H), 4.09 (m, 2H), 4.02 (m, 1H), 3.96 (m, 1H), 3.91 (m, 2H), 3.84 (m, 2H), 3.54 (s, 3H), 2.95 (t, J=6.2 Hz, 2H), 2.03 (m, 2H), 1.31 (d, J=6.1 Hz, 3H);

MS m/z (ESI): 536.2 [M+H]$^+$.

Example 47

N-(5-Cyano-4-(((3,4)-trans-4-methoxytetrahydro-furan-3-yl)oxy)pyridin-2-yl)-7-formyl-6-(((S)-4-methyl-2-carbonyloxazolidin-3-yl)methyl)-3,4-dihydro-1,8-naphthyridin-1(2H)-carboxamide

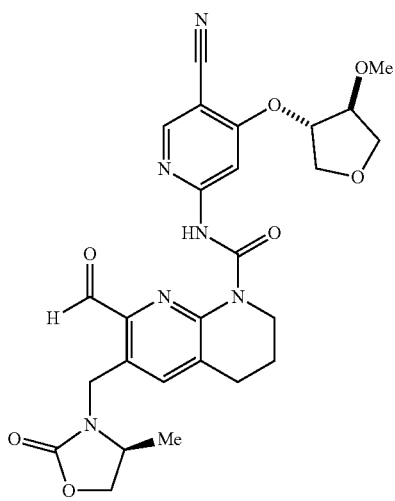

N-(5-Cyano-4-(((3,4)-trans-4-methoxytetrahydrofuran-3-yl)oxy)pyridin-2-yl)-7-formyl-6-(((S)-4-methyl-2-carbonyloxazolidin-3-yl)methyl)-3,4-dihydro-1,8-naphthyridin-1(2H)-carboxamide was prepared in accordance with the method of Example 29.

$^1$H NMR (400 MHz, CDCl$_3$) δ 13.90 (s, 1H), 10.25 (s, 1H), 8.38 (s, 1H), 8.03 (s, 1H), 7.79 (s, 1H), 5.05 (m, 2H), 4.81 (m, 1H), 4.43 (m, 1H), 4.27 (m, 1H), 4.12 (m, 4H), 3.93 (m, 4H), 3.48 (s, 3H), 2.95 (m, 2H), 2.07 (m, 2H), 1.30 (m, 3H);

MS m/z (ESI): 537.2 [M+H]$^+$.

Example 48

(R)-N-(5-Cyano-4-((1-methoxypropan-2-yl)oxy)pyridin-2-yl)-7-formyl-6-((2-thiooxazolidin-3-yl)methyl)-3,4-dihydro-1,8-naphthyridin-1(2H)-carboxamide

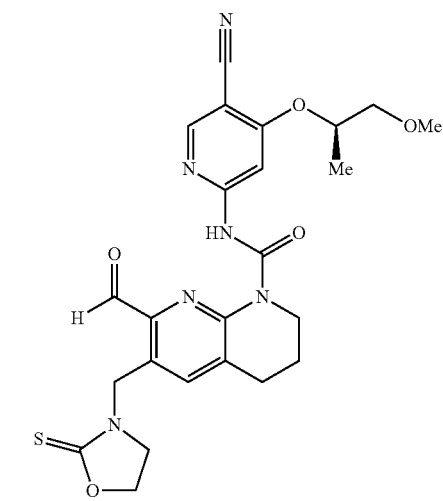 [SMILES: COC[C@@H](C)Oc1cc(NC(=O)N2CCCc3cc(CN4CCOC4=S)c(C=O)nc32)ncc1C#N]

(R)-N-(5-Cyano-4-((1-methoxypropan-2-yl)oxy)pyridin-2-yl)-7-formyl-6-((2-thiooxazolidin-3-yl)methyl)-3,4-dihydro-1,8-naphthyridin-1(2H)-carboxamide was prepared in accordance with the method of Example 29.

$^1$H NMR (400 MHz, CDCl$_3$) δ 13.77 (s, 1H), 10.23 (s, 1H), 8.34 (s, 1H), 8.01 (s, 1H), 7.98 (s, 1H), 5.35 (s, 2H), 4.89-4.85 (m, 1H), 4.61-4.47 (m, 2H), 4.15-4.05 (m, 2H), 3.80 (t, J=8.8 Hz, 2H), 3.69-3.65 (m, 1H), 3.60-3.56 (m, 1H), 3.43 (s, 3H), 2.97 (t, J=6.2 Hz, 2H), 2.09-2.05 (m, 2H), 1.42 (d, J=6.3 Hz, 3H);

MS m/z (ESI): 511.2 [M+H]$^+$.

Example 49

(R)-N-(5-Cyano-4-(3-methoxypyrrolidin-1-yl)pyridin-2-yl)-7-formyl-6-((2-carbonyl -1,3-oxazinan-3-yl)methyl)-3,4-dihydro-1,8-naphthyridin-1(2H)-carboxamide

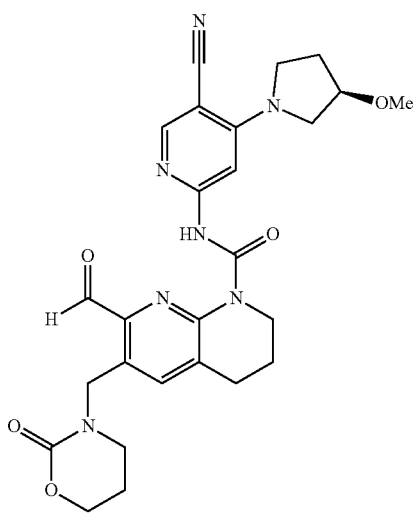 [SMILES: CO[C@@H]1CCN(c2cc(NC(=O)N3CCCc4cc(CN5CCCOC5=O)c(C=O)nc43)ncc2C#N)C1]

(R)-N-(5-Cyano-4-(3-methoxypyrrolidin-1-yl)pyridin-2-yl)-7-formyl-6-((2-carbonyl -1,3-oxazinan-3-yl)methyl)-3,4-dihydro-1,8-naphthyridin-1(2H)-carboxamide was prepared in accordance with the method of Example 29.

$^1$H NMR (400 MHz, CDCl$_3$) δ 13.52 (s, 1H), 10.23 (s, 1H), 8.21 (s, 1H), 7.77 (s, 1H), 7.48 (s, 1H), 5.02 (s, 2H), 4.34-4.28 (m, 2H), 4.12-4.05 (m, 3H), 3.86-3.77 (m, 4H), 3.39-3.32 (m, 5H), 2.93 (t, J=6.1 Hz, 2H), 2.09-1.98 (m, 6H);

MS m/z (ESI): 520.2 [M+H]$^+$.

Example 50

(S)-N-(5-Cyano-4-(3-methoxypyrrolidin-1-yl)pyridin-2-yl)-7-formyl-6-((2-carbonyl -1,3-oxazinan-3-yl)methyl)-3,4-dihydro-1,8-naphthyridin-1(2H)-carboxamide

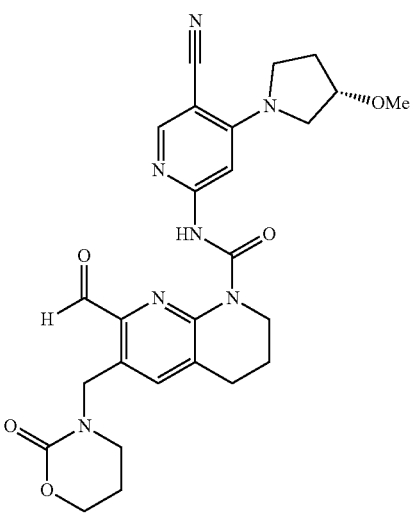 [SMILES: CO[C@H]1CCN(c2cc(NC(=O)N3CCCc4cc(CN5CCCOC5=O)c(C=O)nc43)ncc2C#N)C1]

(S)-N-(5-Cyano-4-(3-methoxypyrrolidin-1-yl)pyridin-2-yl)-7-formyl-6-((2-carbonyl -1,3-oxazinan-3-yl)methyl)-3,4-dihydro-1,8-naphthyridin-1(2H)-carboxamide was prepared in accordance with the method of Example 29.

$^1$H NMR (400 MHz, CDCl$_3$) δ 13.52 (s, 1H), 10.23 (s, 1H), 8.20 (s, 1H), 7.76 (s, 1H), 7.47 (s, 1H), 5.02 (s, 2H), 4.34-4.28 (m, 2H), 4.10-4.05 (m, 3H), 3.83-3.76 (m, 4H), 3.38-3.34 (m, 5H), 2.93 (t, J=6.3 Hz, 2H), 2.11-1.96 (m, 6H);

MS m/z (ESI): 520.2 [M+H]$^+$.

Example 51

(S)-N-(5-Cyano-4-(3-methoxypyrrolidin-1-yl)pyridin-2-yl)-7-formyl-6-((3-carbonylmorpholino)methyl)-3,4-dihydro-1,8-naphthyridin-1(2H)-carboxamide

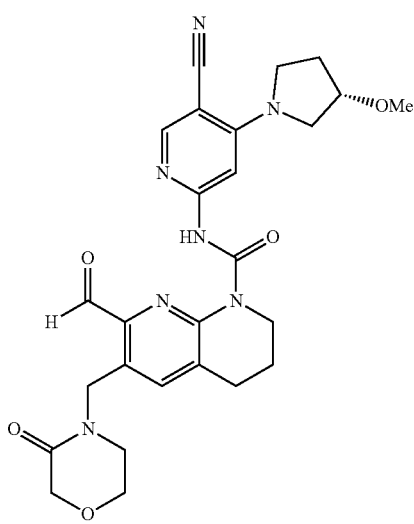 [SMILES: CO[C@H]1CCN(c2cc(NC(=O)N3CCCc4cc(CN5CCOCC5=O)c(C=O)nc43)ncc2C#N)C1]

(S)-N-(5-Cyano-4-(3-methoxypyrrolidin-1-yl)pyridin-2-yl)-7-formyl-6-((3-carbonylmorpholino) methyl)-3,4-dihydro-1,8-naphthyridin-1(2H)-carboxamide was prepared in accordance with the method of Example 1.

$^1$H NMR (400 MHz, CDCl$_3$) δ 13.50 (s, 1H), 10.23 (s, 1H), 8.20 (s, 1H), 7.66 (s, 1H), 7.48 (s, 1H), 5.11 (s, 2H), 4.25 (s, 2H), 4.08 (m, 3H), 3.91-3.87 (m, 2H), 3.80 (m, 4H), 3.43-3.39 (m, 2H), 3.37 (s, 3H), 2.93 (m, 2H), 2.26-2.19 (m, 1H), 2.08-2.01 (m, 3H);

MS m/z (ESI): 520.2 [M+H]$^+$.

Example 52

(R)-N-(5-Cyano-4-(3-methoxypyrrolidin-1-yl)pyridin-2-yl)-7-formyl-6-((3-carbonylmorpholino)methyl)-3,4-dihydro-1,8-naphthyridin-1(2H)-carboxamide

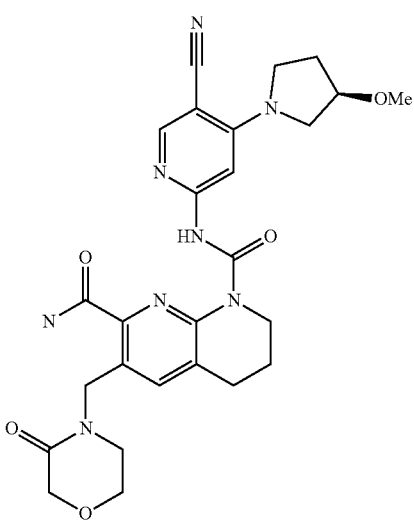 [SMILES: CO[C@@H]1CCN(c2cc(NC(=O)N3CCCc4cc(CN5CCOCC5=O)c(C(N)=O)nc43)ncc2C#N)C1]

(R)-N-(5-Cyano-4-(3-methoxypyrrolidin-1-yl)pyridin-2-yl)-7-formyl-6-((3-carbonylmorpholino) methyl)-3,4-dihydro-1,8-naphthyridin-1(2H)-carboxamide was prepared in accordance with the method of Example 1.

$^1$H NMR (400 MHz, CDCl$_3$) δ 13.50 (s, 1H), 10.23 (s, 1H), 8.20 (s, 1H), 7.66 (s, 1H), 7.48 (s, 1H), 5.11 (s, 2H), 4.25 (s, 2H), 4.08 (m, 3H), 3.91-3.87 (m, 2H), 3.80 (m, 4H), 3.43-3.39 (m, 2H), 3.37 (s, 3H), 2.93 (m, 2H), 2.26-2.19 (m, 1H), 2.08-2.01 (m, 3H);

MS m/z (ESI): 520.2 [M+H]$^+$.

Example 53

N-(5-Cyano-4-(3-methoxyazetidin-1-yl)pyridin-2-yl)-7-formyl-6-((3-carbonylmorpholino) methyl)-3,4-dihydro-1,8-naphthyridin-1(2H)-carboxamide

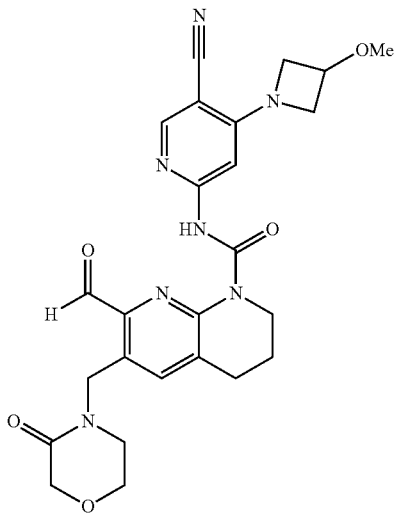 [SMILES: COC1CN(c2cc(NC(=O)N3CCCc4cc(CN5CCOCC5=O)c(C=O)nc43)ncc2C#N)C1]

N-(5-Cyano-4-(3-methoxyazetidin-1-yl)pyridin-2-yl)-7-formyl-6-((3-carbonylmorpholino) methyl)-3,4-dihydro-1,8-naphthyridin-1(2H)-carboxamide was prepared in accordance with the method of Example 1.

$^1$H NMR (400 MHz, DMSO-d6): δ 13.46 (s, 1H), 10.34 (s, 1H), 8.15 (s, 1H), 7.71 (s, 1H), 7.31 (s, 1H), 5.13 (s, 2H), 4.60 (m, 2H), 4.38 (m, 2H), 4.29 (m, 2H), 4.24 (s, 1H), 3.89 (m, 2H), 4.04 (m, 2H), 3.42 (m, 2H), 3.36 (s, 3H), 2.92 (m, 2H), 2.05 (m, 2H);

MS m/z (ESI): 506.2 [M+H]$^+$.

Example 54

N-(5-Cyano-4-(methoxyamino)pyridin-2-yl)-7-formyl-6-((3-carbonylmorpholino) methyl)-3,4-dihydro-1,8-naphthyridine-1(2H)-carboxamide

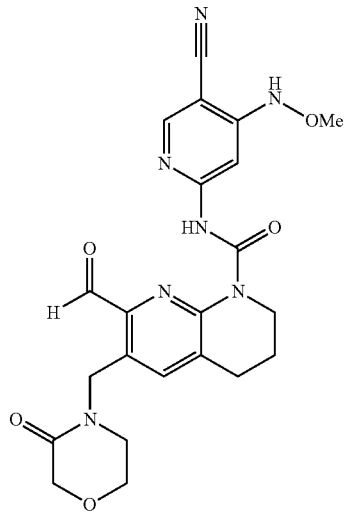 [SMILES: CONc1cc(NC(=O)N2CCCc3cc(CN4CCOCC4=O)c(C=O)nc32)ncc1C#N]

N-(5-Cyano-4-(methoxyamino)pyridin-2-yl)-7-formyl-6-((3-carbonylmorpholino) methyl)-3,4-dihydro-1,8-naphthyridine-1(2H)-carboxamide was prepared in accordance with the method of Example 1.

$^1$H NMR (400 MHz, DMSO-d6): δ 13.06 (s, 1H), 10.66 (s, 1H), 10.13 (s, 1H), 8.40 (s, 1H), 7.76 (s, 1H), 7.64 (s, 1H), 4.93 (s, 2H), 4.16 (s, 2H), 3.96 (m, 2H), 3.89 (m, 2H), 3.68 (m, 3H), 3.36 (m, 2H), 2.91 (m, 2H), 1.97 (m, 2H);

MS m/z (ESI): 466.1 [M+H]$^+$.

Example 55

(S)-N-(5-Cyano-4-((tetrahydrofuran-3-yl)thio)pyridin-2-yl)-7-formyl-6-((3-carbonylmorpholino) methyl)-3,4-dihydro-1,8-naphthyridin-1(2H)-carboxamide

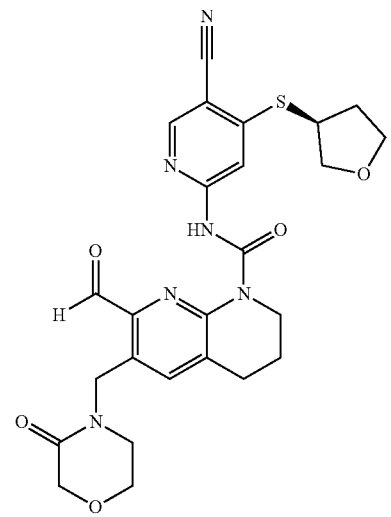 [SMILES: N#Cc1cnc(NC(=O)N2CCCc3cc(CN4CCOCC4=O)c(C=O)nc32)cc1S[C@H]1CCOC1]

(S)-N-(5-Cyano-4-((tetrahydrofuran-3-yl)thio)pyridin-2-yl)-7-formyl-6-((3-carbonylmorpholino) methyl)-3,4-dihydro-1,8-naphthyridin-1(2H)-carboxamide was prepared in accordance with the method of Example 1.

$^1$H NMR (400 MHz, CDCl$_3$) δ 13.90 (s, 1H), 10.23 (s, 1H), 8.37 (s, 1H), 8.28 (s, 1H), 7.69 (s, 1H), 5.11 (s, 2H), 4.40-4.32 (m, 1H), 4.26 (s, 2H), 4.13-4.06 (m, 3H), 4.02-3.96 (m, 2H), 3.94-3.86 (m, 2H), 3.84-3.76 (m, 1H), 3.45-3.40 (m, 2H), 2.95 (t, J=6.2 Hz, 2H), 2.64-2.55 (m, 1H), 2.10-2.02 (m, 3H);

MS m/z (ESI): 523.1 [M+H]$^+$.

Example 56

(R)-N-(5-Cyano-4-((tetrahydrofuran-3-yl)thio)pyridin-2-yl)-7-formyl-6-((3-carbonylmorpholino)methyl)-3,4-dihydro-1,8-naphthyridin-1(2H)-carboxamide

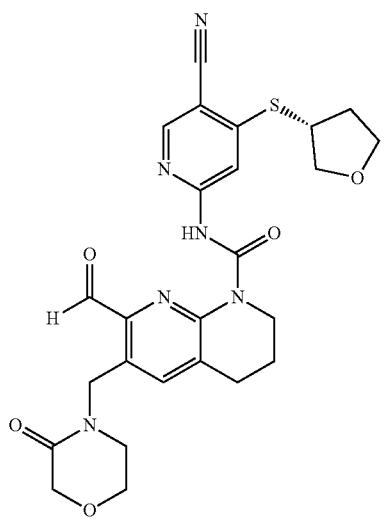

(R)-N-(5-Cyano-4-((tetrahydrofuran-3-yl)thio)pyridin-2-yl)-7-formyl-6-((3-carbonylmorpholino) methyl)-3,4-dihydro-1,8-naphthyridin-1(2H)-carboxamide was prepared in accordance with the method of Example 1.

$^1$H NMR (400 MHz, CDCl$_3$) δ 13.90 (s, 1H), 10.23 (s, 1H), 8.37 (s, 1H), 8.28 (s, 1H), 7.69 (s, 1H), 5.11 (s, 2H), 4.40-4.32 (m, 1H), 4.26 (s, 2H), 4.13-4.06 (m, 3H), 4.02-3.96 (m, 2H), 3.94-3.86 (m, 2H), 3.84-3.76 (m, 1H), 3.45-3.40 (m, 2H), 2.95 (t, J=6.2 Hz, 2H), 2.64-2.55 (m, 1H), 2.10-2.02 (m, 3H);

MS m/z (ESI): 523.1 [M+H]$^+$.

Example 57

N-(5-Cyano-4-(((2-methoxypyridin-3-yl)methyl)amino)pyridin-2-yl)-7-formyl-6-((3-carbonylmorpholino)methyl)-3,4-dihydro-1,8-naphthyridin-1(2H)-carboxamide N-(5-Cyano-4-(((2-methoxypyridin-3-yl)methyl)amino)pyridin-2-yl)-7-formyl-6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$): δ 13.56 (s, 1H), 10.22 (s, 1H), 8.18 (s, 1H), 8.13 (dd, J=5.2, 1.6 Hz, 1H), 7.68 (s, 1H), 7.66 (s, 1H), 7.61 (dd, J=6.0, 1.6 Hz, 1H), 6.89 (m, 1H), 5.58 (m, 1H), 5.11 (s, 2H), 4.49 (d, J=6.0 Hz, 2H), 4.25 (s, 2H), 4.10 (m, 2H), 4.04 (s, 3H), 3.89 (m, 2H), 3.41 (t, J=5.2 Hz, 2H), 2.93 (t, J=6.0 Hz, 2H), 2.05 (m, 2H);

MS m/z (ESI): 557.2 [M+H]$^+$.

Example 58

N-(5-Cyano-4-((4-methoxypyridin-3-yl)amino)pyridin-2-yl)-7-formyl-6-((3-carbonylmorpholino)methyl)-3,4-dihydro-1,8-naphthyridin-1(2H)-carboxamide

Example 59

N-(5-Cyano-4-(((1S,2S)-2-methoxycyclopentyl)amino)pyridin-2-yl)-7-formyl-6-((3-carbonylmorpholino)methyl)-3,4-dihydro-1,8-naphthyridin-1(2H)-carboxamide

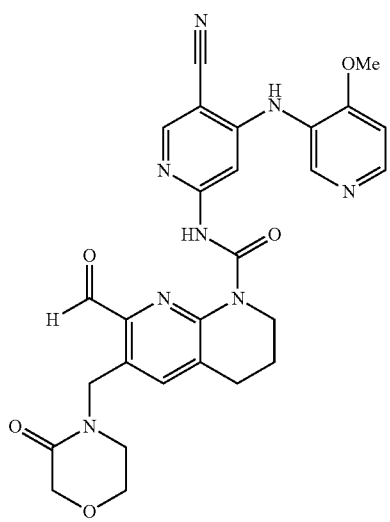 [SMILES: COc1ccncc1Nc1cc(NC(=O)N2CCCc3cc(CN4CCOCC4=O)c(C=O)nc32)ncc1C#N]

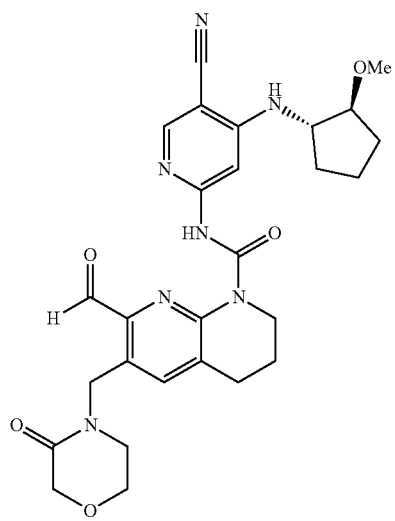 [SMILES: CO[C@H]1CCC[C@@H]1Nc1cc(NC(=O)N2CCCc3cc(CN4CCOCC4=O)c(C=O)nc32)ncc1C#N]

N-(5-Cyano-4-((4-methoxypyridin-3-yl)amino)pyridin-2-yl)-7-formyl-6-((3-carbonylmorpholino) methyl)-3,4-dihydro-1,8-naphthyridin-1(2H)-carboxamide was prepared in accordance with the method of Example 1.

$^1$H NMR (400 MHz, CDCl$_3$) δ 13.64 (s, 1H), 10.23 (s, 1H), 8.65 (s, 1H), 8.42 (d, J=5.6 Hz, 1H), 8.33 (s, 1H), 7.92 (s, 1H), 7.65 (s, 1H), 6.95 (d, J=5.6 Hz, 1H), 6.61 (s, 1H), 5.10 (s, 2H), 4.25 (s, 2H), 4.02-4.01 (m, 2H), 3.96 (s, 3H), 3.91-3.84 (m, 2H), 3.44-3.34 (m, 2H), 2.91 (t, J=6.2 Hz, 2H), 2.02-1.99 (m, 2H);

MS m/z (ESI): 543.2 [M+H]$^+$.

N-(5-Cyano-4-(((1S,2S)-2-methoxycyclopentyl)amino)pyridin-2-yl)-7-formyl-6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$) δ 13.56 (s, 1H), 10.23 (s, 1H), 8.17 (s, 1H), 7.73 (s, 1H), 7.66 (s, 1H), 5.11 (s, 2H), 4.87 (m, 1H), 4.26 (s, 2H), 4.09 (m, 2H), 3.93-3.85 (m, 3H), 3.69 (m, 1H), 3.42-3.39 (m, 4H), 2.93 (m, 2H), 2.33 (m, 1H), 2.07-2.01 (m, 2H), 1.95-1.50 (m, 6H);

MS m/z (ESI): 534.2 [M+H]$^+$.

Example 60

N-(5-Cyano-4-(((1R,2R)-2-methoxycyclopentyl)amino)pyridin-2-yl)-7-formyl-6-((3-carbonylmorpholino)methyl)-3,4-dihydro-1,8-naphthyridin-1(2H)-carboxamide

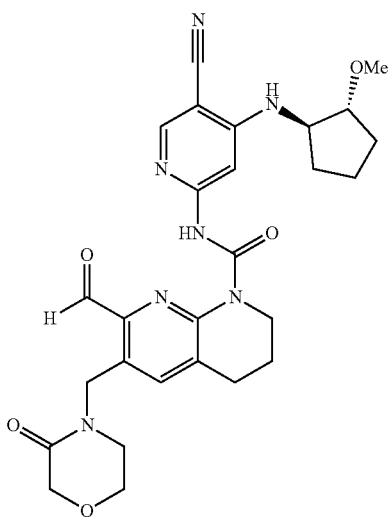 [SMILES: CO[C@@H]1CCC[C@H]1Nc1cc(NC(=O)N2CCCc3cc(CN4CCOCC4=O)c(C=O)nc32)ncc1C#N]

N-(5-Cyano-4-(((1R,2R)-2-methoxycyclopentyl)amino)pyridin-2-yl)-7-formyl-6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$) δ 13.56 (s, 1H), 10.23 (s, 1H), 8.17 (s, 1H), 7.73 (s, 1H), 7.66 (s, 1H), 5.11 (s, 2H), 4.87 (m, 1H), 4.26 (s, 2H), 4.09 (m, 2H), 3.93-3.85 (m, 3H), 3.69 (m, 1H), 3.42-3.39 (m, 4H), 2.93 (m, 2H), 2.33 (m, 1H), 2.07-2.01 (m, 2H), 1.95-1.50 (m, 6H);

MS m/z (ESI): 534.2 [M+H]$^+$.

Example 61

N-(5-Cyano-4-trans-((1,2)-2-methoxycyclobutoxy)pyridin-2-yl)-7-formyl-6-((3-carbonylmorpholino)methyl)-3,4-dihydro-1,8-naphthyridin-1(2H)-carboxamide

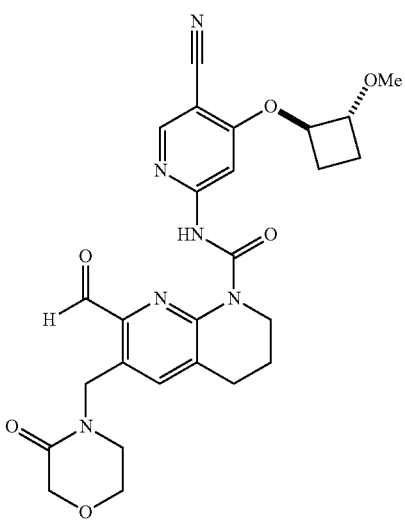

N-(5-Cyano-4-trans-((1,2)-2-methoxycyclobutoxy)pyridin-2-yl)-7-formyl-6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$): δ 13.83 (s, 1H), 10.23 (s, 1H), 8.36 (s, 1H), 8.00 (s, 1H), 7.68 (s, 1H), 5.11 (s, 2H), 4.68 (m, 1H), 4.26 (s, 2H), 4.15-4.03 (m, 3H), 3.95-3.84 (m, 2H), 3.45-3.35 (m, 5H), 2.95 (t, J=6.2 Hz, 2H), 2.43 (m, 1H), 2.29-2.20 (m, 1H), 2.05 (m, 2H), 1.72-1.63 (m, 2H);

MS m/z (ESI): 521.2 [M+H]$^+$.

Example 62

N-(5-Cyano-4-cis-((1,2)-2-methoxycyclobutoxy)pyridin-2-yl)-7-formyl-6-((3-carbonylmorpholino)methyl)-3,4-dihydro-1,8-naphthyridin-1(2H)-carboxamide

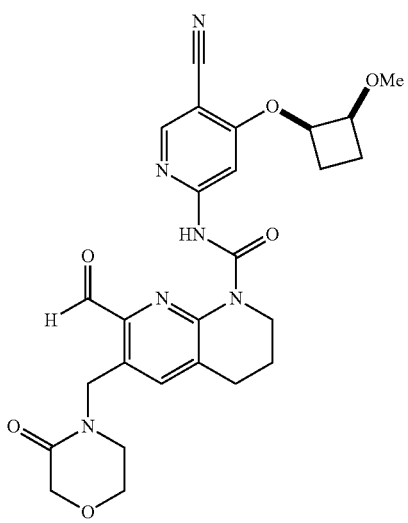

N-(5-Cyano-4-cis-((1,2)-2-methoxycyclobutoxy)pyridin-2-yl)-7-formyl-6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$): δ 13.83 (s, 1H), 10.25 (s, 1H), 8.37 (s, 1H), 7.89 (s, 1H), 7.69 (s, 1H), 5.12 (s, 2H), 4.95 (m, 1H), 4.30-4.20 (m, 3H), 4.09 (m, 2H), 3.92-3.84 (m, 2H), 3.45-3.38 (m, 5H), 2.95 (t, J=6.2 Hz, 2H), 2.40 (m, 2H), 2.15 (m, 2H), 2.05 (m, 2H);

MS m/z (ESI): 521.2 [M+H]$^+$.

Example 63

(S)-N-(5-Cyano-4-(3-methoxypyrrolidin-1-yl)pyridin-2-yl)-7-formyl-6-((4-methyl-2-carbonylpiperazin-1-yl)methyl)-3,4-dihydro-1,8-naphthyridin-1(2H)-carboxamide

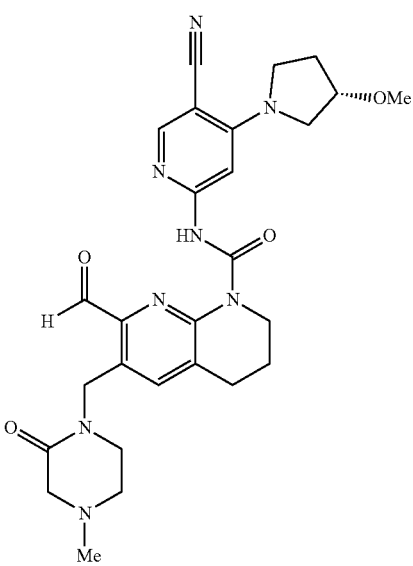 [SMILES: CO[C@H]1CCN(c2cc(NC(=O)N3CCCc4cc(CN5CCN(C)CC5=O)c(C=O)nc43)ncc2C#N)C1]

(S)-N-(5-Cyano-4-(3-methoxypyrrolidin-1-yl)pyridin-2-yl)-7-formyl-6-((4-methyl-2-carbonylpiperazin-1-yl)methyl)-3,4-dihydro-1,8-naphthyridin-1(2H)-carboxam was prepared in accordance with the method of Example 1.

$^1$H NMR (400 MHz, CDCl$_3$) δ 13.51(s, 1H), 10.23 (s, 1H), 8.20 (s, 1H), 7.67 (s, 1H), 7.48 (s, 1H), 5.09 (s, 2H), 4.07 (m, 3H), 3.81 (m, 4H), 3.37 (m, 5H), 3.24 (m, 2H), 2.93 (m, 2H), 2.71 (m, 2H), 2.39 (m, 3H), 2.21 (m, 1H), 2.02 (m, 3H);

MS m/z (ESI): 533.2 [M+H]$^+$.

Example 64

(R)-N-(5-Cyano-4-(3-methoxypyrrolidin-1-yl)pyridin-2-yl)-7-formyl-6-((4-methyl-2-carbonylpiperazin-1-yl)methyl)-3,4-dihydro-1,8-naphthyridin-1(2H)-carboxamide

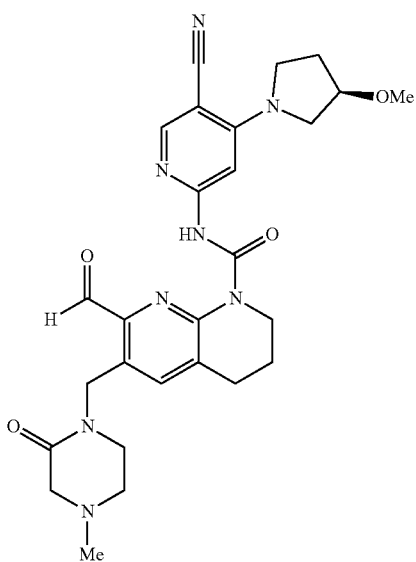 [SMILES: CO[C@@H]1CCN(c2cc(NC(=O)N3CCCc4cc(CN5CCN(C)CC5=O)c(C=O)nc43)ncc2C#N)C1]

(R)-N-(5-Cyano-4-(3-methoxypyrrolidin-1-yl)pyridin-2-yl)-7-formyl-6-((4-methyl-2-carbonylpiperazin-1-yl)methyl)-3,4-dihydro-1,8-naphthyridin-1(2H)-carboxamide was prepared in accordance with the method of Example 1.

$^1$H NMR (400 MHz, CDCl$_3$) δ 13.51(s, 1H), 10.23 (s, 1H), 8.20 (s, 1H), 7.67 (s, 1H), 7.48 (s, 1H), 5.09 (s, 2H), 4.07 (m, 3H), 3.81 (m, 4H), 3.37 (m, 5H), 3.24 (m, 2H), 2.93 (m, 2H), 2.71 (m, 2H), 2.39 (m, 3H), 2.21(m, 1H), 2.02 (m, 3H);

MS m/z (ESI): 533.2 [M+H]$^+$.

Example 65

N-(5-Cyano-4-((2-methoxyethyl)amino)pyridin-2-yl)-6-((4-cyclopropyl-2-carbonylpiperazin-1-yl)-7-formyl-3,4-dihydro-1,8-naphthyridin-1(2H)-carboxamide

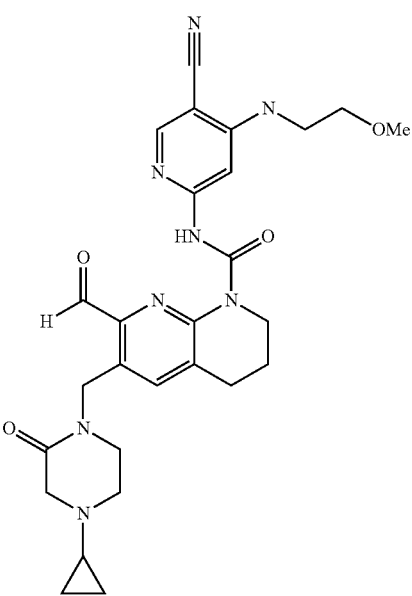 [SMILES: COCCNc1cc(NC(=O)N2CCCc3cc(CN4CCN(C5CC5)CC4=O)c(C=O)nc32)ncc1C#N]

N-(5-Cyano-4-((2-methoxyethyl)amino)pyridin-2-yl)-6-((4-cyclopropyl-2-carbonylpiperazin-1-yl)-7-formyl-3,4-dihydro-1,8-naphthyridin-1(2H)-carboxamide was prepared in accordance with the method of Example 1.

$^1$H NMR (400 MHz, CDCl$_3$): δ 13.60 (s, 1H), 10.22 (s, 1H), 8.18 (s, 1H), 7.63 (s, 1H), 7.56 (s, 1H), 5.30 (m, 1H), 5.06 (s, 2H), 4.07 (m, 2H), 3.64 (m, 2H), 3.49 (m, 2H), 3.41 (s, 3H), 3.39 (s, 2H), 3.30 (t, J=5.6 Hz, 2H), 2.92 (t, J=6.4 Hz, 2H), 2.86 (t, J=5.6 Hz, 2H), 2.03 (m, 2H), 1.70 (m, 1H), 0.51 (m, 2H), 0.44 (m, 2H);

MS m/z (ESI): 533.2 [M+H]$^+$.

Example 66

N-(5-Cyano-4-(((trans)-4-methoxytetrahydrofuran-3-yl)amino)pyridin-2-yl)-7-formyl -6-((3-carbonylmorpholino)methyl)-3,4-dihydro-1,8-naphthyridin-1(2H)-carboxamide

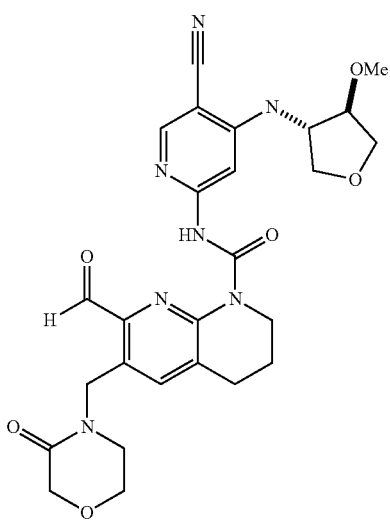

N-(5-Cyano-4-(((trans)-4-methoxytetrahydrofuran-3-yl)amino)pyridin-2-yl)-7-formyl -6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$) δ 13.65 (s, 1H), 10.23 (s, 1H), 8.21 (s, 1H), 7.77 (s, 1H), 7.67 (s, 1H), 5.11 (s, 2H), 4.99 (d, J=6.2 Hz, 1H), 4.26 (s, 2H), 4.16-4.06 (m, 5H), 3.93-3.87 (m, 3H), 3.86-3.80 (m, 2H), 3.54 (s, 3H), 3.44-3.39 (m, 2H), 2.94 (t, J=6.2 Hz, 2H), 2.09-2.01 (m, 2H);

MS m/z (ESI): 536.2 [M+H]$^+$.

Example 67

N-(5-Cyano-4-(((3,4)-trans-4-methoxytetrahydrofuran-3-yl)oxy)pyridin-2-yl)-7-formyl -6-((3-carbonylmorpholino)methyl)-3,4-dihydro-1,8-naphthyridin-1(2H)-carboxamide

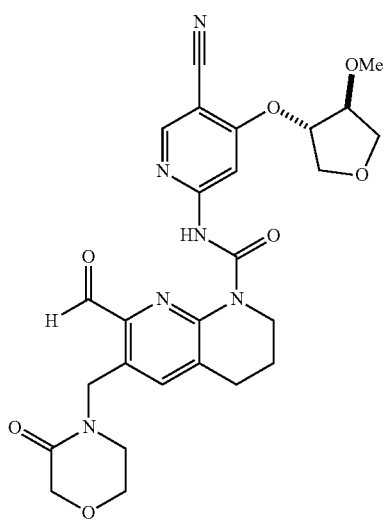

N-(5-Cyano-4-(((3,4)-trans-4-methoxytetrahydrofuran-3-yl)oxy)pyridin-2-yl)-7-formyl -6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$) δ 13.91(s, 1H), 10.24 (s, 1H), 8.38 (s, 1H), 8.00 (s, 1H), 7.69 (s, 1H), 5.11(d, J=2.0 Hz, 2H), 5.00 (d, J=4.4 Hz, 1H), 4.27 (m, 3H), 4.11 (m, 4H), 3.89 (m, 4H), 3.50 (s, 3H), 3.43 (m, 2H), 2.93 (m, 2H), 2.04 (m, 2H);

MS m/z (ESI): 537.2 [M+H]$^+$.

Example 68

N-(5-Cyano-4-(((3,4)-trans-4-methoxytetrahydro-2H-pyran-3-yl)oxy)pyridin-2-yl)-7-formyl-6-((3-carbonylmorpholino)methyl)-3,4-dihydro-1,8-naphthyridin-1(2H)-carboxamide

Example 69

N-(5-Cyano-4-(((3,4)-trans-3-methoxytetrahydro-2H-pyran-4-yl)oxy)pyridin-2-yl)-7-formyl-6-((3-carbonylmorpholino)methyl)-3,4-dihydro-1,8-naphthyridin-1(2H)-carboxamide

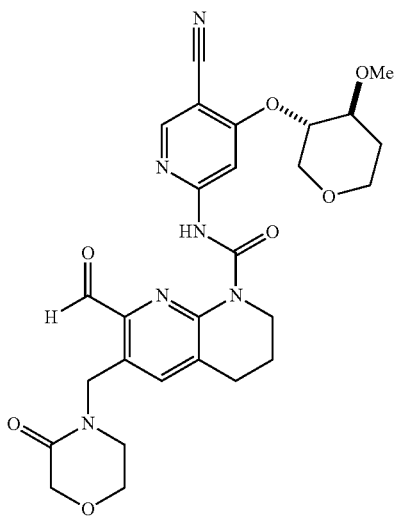

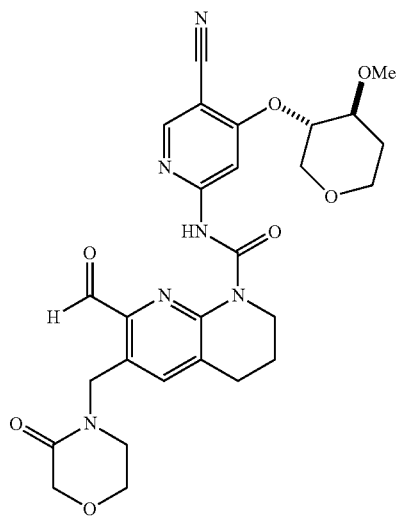

N-(5-Cyano-4-(((3,4)-trans-4-methoxytetrahydro-2H-pyran-3-yl)oxy)pyridin-2-yl)-7-formyl-6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$) δ 13.83 (s, 1H), 10.25 (s, 1H), 8.37 (s, 1H), 8.10 (s, 1H), 7.69 (s, 1H), 5.11 (s, 2H), 4.54 (m, 1H), 4.25 (s, 2H), 4.13-4.05 (m, 3H), 3.99-3.85 (m, 3H), 3.60 (m, 1H), 3.56-3.48 (m, 2H), 3.46 (s, 3H), 3.44-3.39 (m, 2H), 2.94 (t, J=6.2 Hz, 2H), 2.26-2.17 (m, 1H), 2.09-2.02 (m, 2H), 1.73 (m, 1H);

MS m/z (ESI): 551.2 [M+H]$^+$.

N-(5-Cyano-4-(((3,4)-trans-3-methoxytetrahydro-2H-pyran-4-yl)oxy)pyridin-2-yl)-7-formyl-6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$) δ 13.87 (s, 1H), 10.26 (s, 1H), 8.38 (s, 1H), 8.08 (s, 1H), 7.70 (s, 1H), 5.12 (s, 2H), 4.67 (t, J=9.8 Hz, 1H), 4.25 (s, 2H), 4.08 (m, 3H), 3.93 (m, 3H), 3.58 (m, 1H), 3.51 (s, 3H), 3.49-3.39 (m, 4H), 2.95 (t, J=6.2 Hz, 2H), 2.32-2.24 (m, 1H), 2.10-2.02 (m, 2H), 1.93-1.83 (m, 1H);

MS m/z (ESI): 551.2 [M+H]$^+$.

Example 70

N-(5-Cyano-4-(((3,4)-trans-4-methoxytetrahydro-2H-pyran-3-yl)amino)pyridin-2-yl)-7-formyl-6-((3-carbonylmorpholino)methyl)-3,4-dihydro-1,8-naphthyridin-1(2H)-carboxamide

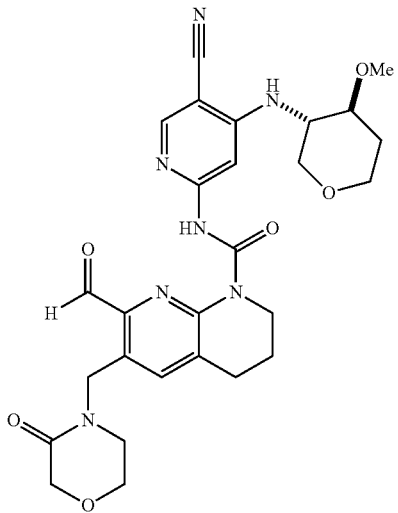

N-(5-Cyano-4-(((3,4)-trans-4-methoxytetrahydro-2H-pyran-3-yl)amino)pyridin-2-yl)-7-formyl-6-((3-carbonylmorpholino)methyl)-3,4-dihydro-1,8-naphthyridin-1(2H)-carboxamide was prepared in accordance with the method of Example 1.

$^1$H NMR (400 MHz, CDCl$_3$) δ 13.59 (s, 1H), 10.25 (s, 1H), 8.19 (s, 1H), 7.74 (s, 1H), 7.67 (s, 1H), 5.11 (s, 2H), 4.98 (s, 1H), 4.25 (s, 2H), 4.16 (m, 1H), 4.11-4.06 (m, 2H), 3.98-3.92 (m, 1H), 3.90-3.86 (m, 2H), 3.75-3.66 (m, 1H), 3.55 (m, 1H), 3.44-3.39 (m, 5H), 3.33-3.20 (m, 2H), 2.93 (t, J=6.3 Hz, 2H), 2.21 (m, 1H), 2.06-2.02 (m, 2H), 1.67 (m, 1H);

MS m/z (ESI): 550.2 [M+H]$^+$.

Biological Test and Evaluation

1. Enzymologic Experiment of FGFR4

In this experiment, the inhibitory effect of the compounds on FGFR4 kinase activity was tested by a fluorescence resonance energy transfer (TR-FRET) method, and the half maximal inhibitory concentration (IC$_{50}$) of the compounds on the FGFR4 kinase activity was determined.

1) 1~5 μL of FGFR4 enzyme solution was added to a 384-well plate, and the final concentration of the enzyme was 0.1~5 nM.
2) 1~5 μL of diluted solution in gradient of the compound was added.
3) 1~5 μL of a substrate mixture containing substrate polypeptide with a final concentration of 5~50 nM and ATP with a final concentration of 10~200 μM was added.
4) The mixture was incubated for 0.5~3 hours at room temperature.
5) 10 μL of EDTA and a test solution comprising labeled antibody were added, and the plate was incubated for 1 hour at room temperature.
6) The fluorescence signal values of each plate were determined by a microplate reader at 665 nm.
7) The inhibition rates were calculated according to the fluorescence signal values.
8) The IC$_{50}$ of the compound was obtained by curve fitting according to the inhibition rates at different concentrations, and the enzymatic activity of the specific example compounds is shown in Table 1.

2. Enzymologic Experiment of FGFR1

In this experiment, the inhibitory effect of the compounds on FGFR1 kinase activity was tested by a fluorescence resonance energy transfer (TR-FRET) method, and the half maximal inhibitory concentration (IC$_{50}$) of the compounds on the FGFR1 kinase activity was determined.

1) 1~5 μL of FGFR1 enzyme solution was added to a 384-well plate, and the final concentration of the enzyme was 0.1~5 nM.
2) 1~5 μL of diluted solution in gradient of the compound was added.
3) 1~5 μL of a substrate mixture containing substrate polypeptide with a final concentration of 5~50 nM and ATP with a final concentration of 10~200 μM was added.
4) The mixture was incubated for 0.5~3 hours at room temperature.
5) 10 μL of EDTA and a test solution comprising labeled antibody were added, and the plate was incubated for 1 hour at room temperature.
6) The fluorescence signal values of each plate were determined by a microplate reader at 665 nm.
7) The inhibition rates were calculated according to the fluorescence signal values.
8) The IC$_{50}$ of the compound was obtained by curve fitting according to the inhibition rates at different concentrations, and the enzymatic activity of the specific example compounds is shown in Table 1.

TABLE 1

| Compound No. | FGFR4 IC$_{50}$ (nM) | FGFR1 IC$_{50}$ (nM) |
| --- | --- | --- |
| Example 1 | 0.8 | >10000 |
| Example 2 | 2.9 | >10000 |
| Example 3 | 5.4 | >10000 |
| Example 4 | 5.1 | >10000 |
| Example 5 | 7.3 | >10000 |
| Example 6 | 0.4 | >10000 |
| Example 7 | 0.6 | >10000 |
| Example 8 | 3.4 | >10000 |
| Example 9 | 4.7 | >10000 |
| Example 11 | 1.77 | >10000 |
| Example 13 | 4.61 | >10000 |
| Example 15 | 3.69 | >10000 |
| Example 16 | 4.57 | >10000 |
| Example 21 | 1.71 | >10000 |
| Example 23 | 2.06 | >10000 |
| Example 29 | 0.96 | >10000 |
| Example 30 | 2.50 | >10000 |
| Example 31 | 2.89 | >10000 |
| Example 32 | 3.15 | >10000 |
| Example 33 | 1.44 | >10000 |
| Example 34 | 1.27 | >10000 |
| Example 35 | 2.06 | >10000 |
| Example 36 | 4.25 | >10000 |
| Example 37 | 1.12 | >10000 |
| Example 38 | 4.65 | >10000 |
| Example 39 | 3.27 | >10000 |
| Example 40 | 9.50 | >10000 |
| Example 41 | 4.69 | >10000 |
| Example 42 | 2.30 | >10000 |
| Example 43 | 4.41 | >10000 |

TABLE 1-continued

| Compound No. | FGFR4 IC$_{50}$ (nM) | FGFR1 IC$_{50}$ (nM) |
|---|---|---|
| Example 44 | 6.50 | >10000 |
| Example 45 | 4.66 | >10000 |
| Example 46 | 2.93 | >10000 |
| Example 47 | 4.95 | >10000 |
| Example 48 | 8.48 | >10000 |
| Example 49 | 1.28 | >10000 |
| Example 50 | 3.86 | >10000 |
| Example 51 | 3.46 | >10000 |
| Example 52 | 1.33 | >10000 |
| Example 53 | 6.31 | >10000 |
| Example 54 | 2.77 | >10000 |
| Example 55 | 5.29 | >10000 |
| Example 56 | 7.52 | >10000 |
| Example 57 | 7.63 | >10000 |
| Example 58 | 3.78 | >10000 |
| Example 59 | 4.67 | >10000 |
| Example 60 | 0.99 | >10000 |
| Example 61 | 1.02 | >10000 |
| Example 62 | 2.10 | >10000 |
| Example 63 | 2.49 | >10000 |
| Example 64 | 1.62 | >10000 |
| Example 65 | 1.62 | >10000 |
| Example 66 | 0.97 | >10000 |
| Example 67 | 2.31 | >10000 |
| Example 68 | 2.73 | >10000 |
| Example 69 | 3.30 | >10000 |
| Example 70 | 1.34 | >10000 |

It can be seen from the enzymatic activity data of the specific example compounds that the series of compounds of the present invention had very strong inhibitory effect on FGFR4 kinase activity, but almost no inhibitory effect on FGFR1 kinase activity. Therefore, the series of compounds of the present invention had very high selectivity for FGFR4 kinase activity.

3. Experiment on the Inhibition of Hep 3B Cell Proliferation

In this experiment, the inhibitory effect of the compounds on Hep 3B cell proliferation was tested by a CellTiter-Glo method, and the half maximal inhibitory concentration (IC$_{50}$) of the compounds on the activity of cell proliferation was determined.

1) A 96-well cell culture plate was seeded with 50~100 μL of Hep 3B cell suspension at a density of 1~5×10$^4$ cells/ml. The culture plate was incubated in an incubator for 16~24 hours (37° C., 5% CO$_2$).
2) Different concentrations of the test compound in a gradient dilution were added to the cells in the culture plate. The culture plate was incubated in an incubator for 72 hours (37° C., 5% CO$_2$).
3) 50~100 μL of CellTiter-Glo reagent were added to each well. Then, the culture plate was shaken or left to stand for 5~30 minutes at room temperature.
4) The chemiluminescence signal values of each plate were determined by a microplate reader.
5) The inhibition rates were calculated according to the chemiluminescence signal values.
6) The IC$_{50}$ of the compound was obtained by curve fitting according to the inhibition rates at different concentrations, and the cell activity of the specific example compounds is shown in Table 2.

4. Experiment on the Inhibition of HuH-7 Cell Proliferation

In this experiment, the inhibitory effect of the compounds on HuH-7 cell proliferation was tested by a CellTiter-Glo method, and the half maximal inhibitory concentration (IC$_{50}$) of the compounds on the activity of cell proliferation was determined.

1) A 96-well cell culture plate was seeded with 50~100 μL of HuH-7 cell suspension at a density of 1~5×10$^4$ cells/ml. The culture plate was incubated in an incubator for 16~24 hours (37° C., 5% CO$_2$).
2) Different concentrations of the test compound in a gradient dilution were added to the cells in the culture plate. The culture plate was incubated in an incubator for 72 hours (37° C., 5% CO$_2$).
3) 50~100 μL of CellTiter-Glo reagent was added to each well. Then, the culture plate was shaken or left to stand for 5~30 minutes at room temperature.
4) The chemiluminescence signal values of each plate were determined by a microplate reader.
5) The inhibition rates were calculated according to the chemiluminescence signal values.
6) The IC$_{50}$ of the compound was obtained by curve fitting according to the inhibition rates at different concentrations, and the cell activity of the specific example compounds is shown in Table 2.

5. Experiment on the Inhibition of SK-HEP-1 Cell Proliferation

In this experiment, the inhibitory effect of the compounds on SK-HEP-1 cell proliferation was tested by a CellTiter-Glo method, and the half maximal inhibitory concentration (IC$_{50}$) of the compounds on the activity of cell proliferation was determined.

1) A 96-well cell culture plate was seeded with 50~100 μL of SK-HEP-1 cell suspension at a density of 1~5×10$^4$ cells/ml. The culture plate was incubated in an incubator for 16~24 hours (37° C., 5% CO$_2$).
2) Different concentrations of the test compound in a gradient dilution were added to the cells in the culture plate. The culture plate was incubated in an incubator for 72 hours (37° C., 5% CO$_2$).
3) 50~100 μL of CellTiter-Glo reagent were added to each well. Then, the culture plate was shaken or left to stand for 5~30 minutes at room temperature.
4) The chemiluminescence signal values of each plate were determined by a microplate reader.
5) The inhibition rates were calculated according to the chemiluminescence signal values.
6) The IC$_{50}$ of the compound was obtained by curve fitting according to the inhibition rates at different concentrations, and the cell activity of the specific example compounds is shown in Table 2.

TABLE 2

| Compound No. | Hep 3B IC$_{50}$ (nM) | HuH-7 IC$_{50}$ (nM) | SK-HEP-1 IC$_{50}$ (nM) |
|---|---|---|---|
| Example 1 | 0.7 | 3.0 | >10000 |
| Example 3 | 13.1 | 40.9 | >10000 |
| Example 4 | 2.5 | 18.4 | >10000 |
| Example 5 | 8.2 | 34.9 | >10000 |
| Example 6 | 1.1 | 7.4 | >10000 |
| Example 7 | 1.4 | 10.2 | >10000 |
| Example 8 | 0.9 | 8.6 | >10000 |
| Example 9 | 1.4 | 9.1 | >10000 |
| Example 11 | 8.4 | 12.4 | >10000 |
| Example 13 | 20.8 | 32.3 | >10000 |
| Example 15 | 3.0 | 4.9 | >10000 |
| Example 16 | 10.5 | 13.2 | >10000 |
| Example 21 | 8.6 | 13.4 | >10000 |

TABLE 2-continued

| Compound No. | Hep 3B IC$_{50}$ (nM) | HuH-7 IC$_{50}$ (nM) | SK-HEP-1 IC$_{50}$ (nM) |
|---|---|---|---|
| Example 23 | 4.6 | 6.7 | >10000 |
| Example 29 | 0.6 | 2.6 | >10000 |
| Example 30 | 4.6 | 13.4 | >10000 |
| Example 31 | 2.9 | 6.5 | >10000 |
| Example 32 | 3.1 | 5.8 | >10000 |
| Example 33 | 3.7 | 7.2 | >10000 |
| Example 34 | 2.3 | 4.9 | >10000 |
| Example 35 | 2.2 | 4.6 | >10000 |
| Example 36 | 8.0 | 20.4 | >10000 |
| Example 37 | 2.8 | 4.1 | >10000 |
| Example 38 | 13.3 | 11.8 | >10000 |
| Example 39 | 39.3 | 34.6 | >10000 |
| Example 40 | 38.7 | 29.6 | >10000 |
| Example 41 | 9.9 | 10.2 | >10000 |
| Example 42 | 6.7 | 8.4 | >10000 |
| Example 43 | 8.1 | 8.1 | >10000 |
| Example 44 | 11.5 | 35.4 | >10000 |
| Example 45 | 14.2 | 32.2 | >10000 |
| Example 46 | 12.7 | 44.4 | >10000 |
| Example 47 | 9.9 | 24.4 | >10000 |
| Example 48 | 13.1 | 15.6 | >10000 |
| Example 49 | 4.4 | 11.3 | >10000 |
| Example 50 | 5.5 | 15.3 | >10000 |
| Example 51 | 25.1 | 27.5 | >10000 |
| Example 52 | 4.8 | 8.1 | >10000 |
| Example 53 | 41.5 | — | >10000 |
| Example 54 | 17.5 | 24.1 | >10000 |
| Example 55 | 14.5 | 36.1 | >10000 |
| Example 56 | 22.7 | 50.1 | >10000 |
| Example 57 | 10.2 | 24.3 | >10000 |
| Example 58 | 6.9 | 20.7 | >10000 |
| Example 59 | 8.6 | 18.7 | >10000 |
| Example 60 | 1.0 | 2.7 | >10000 |
| Example 61 | 3.7 | 6.2 | >10000 |
| Example 62 | 3.4 | 4.2 | >10000 |
| Example 63 | 13.8 | 28.9 | >10000 |
| Example 64 | 5.3 | 14.6 | >10000 |
| Example 65 | 4.3 | 15.2 | >10000 |
| Example 66 | 3.3 | 11.7 | >10000 |
| Example 67 | 16.7 | 29.5 | >10000 |
| Example 68 | 10.9 | 40.8 | >10000 |
| Example 69 | 22.6 | — | >10000 |
| Example 70 | 6.2 | 19.4 | >10000 |

It can be seen from the cell activity data of the specific example compounds that the series of compounds of the present invention had very strong inhibitory effect on the proliferation of Hep3B and HuH-7 cells with high expression of FGF19 and FGFR4ssed, but no inhibitory effect on the proliferation of SK-HEP-1 cells with low expression of FGF19 and FGFR4. Therefore, these compounds showed excellent cell activity and selectivity.

6. Pharmacokinetic (PK) Analysis in Rats

The pharmacokinetic test in rats of the preferred example compounds of the present invention was performed with Sprague Dawley (SD) rats (Shanghai Jiesijie Laboratory Animal Co., LTD).

Mode of administration: a single intragastric administration.
Dosage: 5 mg/10 ml/kg.
Formulation: 0.5% methyl cellulose and 1% Tween 80, ultrasonic dissolution.
Sampling points: 0.5, 1, 2, 4, 6, 8 and 24 hours after administration.
Sample treatment:
1) 0.2 ml of intravenous blood was collected and placed in a K2EDTA test tube. The blood was centrifuged at room temperature at the speed of 1000~3000×g for 5~20 minutes to isolate the plasma, which was then stored at −80° C.
2) 160 µL of acetonitrile was added to 40 µL of plasma sample for precipitation, and then the mixture was centrifuged at the speed of 500~2000×g for 5~20 minutes.
3) 100 µL of treated solution was taken, and the concentration of the test compound was analyzed by LC/MS/MS. The LC/MS/MS analytical instrument was AB Sciex API 4000.

Liquid chromatography analysis:
Condition of Liquid chromatography: Shimadzu LC-20AD pump
Chromatographic column: phenomenex Gemiu 5 um C18 50×4.6 mm
Mobile phase: Solution A is 0.1% formic acid aqueous solution, and Solution B is acetonitrile
Flow rate: 0.8 mL/min
Elution time: 0-3.5 minutes, the eluent was used as follows:

| Time/Minute | Solution A | Solution B |
|---|---|---|
| 0.01 | 80% | 20% |
| 0.5 | 80% | 20% |
| 1.2 | 10% | 90% |
| 2.6 | 10% | 90% |
| 2.7 | 80% | 20% |
| 3.8 | 80% | 20% |

Pharmacokinetics:
The main parameters were calculated with WinNonlin 6.1, and the experimental results of the pharmacokinetic test in rats are shown in Table 3 below:

TABLE 3

| | Pharmacokinetic Test (5 mg/kg) | | | | | |
|---|---|---|---|---|---|---|
| Example No. | Peak Time $t_{max}$(ng/mL) | Plasma Concentration $C_{max}$(ng/mL) | Area Under Curve AUC$_{0-t}$(ng/mL × h) | Area Under Curve AUC$_{0-\infty}$(ng/mL × h) | Half-Time $t_{1/2}$(h) | Mean Residence Time MRT(h) |
| 1 | 0.5 | 1140 | 1009 | 5045 | 1.1 | 1.1 |
| 4 | 2 | 3371 | 8740 | 8742 | 0.61 | 3.07 |
| 6 | 2 | 3500 | 9125 | 9135 | 0.9 | 1 |
| 8 | 2 | 2060 | 4790 | 4945 | 1.16 | 3.74 |
| 11 | 2 | 1540 | 3890 | 3960 | 1.16 | 2.68 |
| 13 | 2 | 1195 | 3507 | 3571 | 1.16 | 2.8 |
| 16 | 2 | 1600 | 5520 | 5610 | 1.02 | 2.96 |
| 23 | 2 | 2313 | 9106 | 9109 | 1.02 | 3.5 |
| 29 | 2 | 3377 | 9464 | 9464 | 1.27 | 2.48 |
| 31 | 2 | 3720 | 1925 | 1925 | 1.27 | 4.54 |

TABLE 3-continued

| | | | Pharmacokinetic Test (5 mg/kg) | | | |
|---|---|---|---|---|---|---|
| Example No. | Peak Time $t_{max}$(ng/mL) | Plasma Concentration $C_{max}$(ng/mL) | Area Under Curve $AUC_{0-t}$(ng/mL × h) | Area Under Curve $AUC_{0-\infty}$(ng/mL × h) | Half-Time $t_{1/2}$(h) | Mean Residence Time MRT(h) |
| 38 | 2 | 2660 | 2400 | 2535 | 1.38 | 3.91 |
| 40 | 2 | 1565 | 1075 | 1099 | 1.05 | 3.36 |
| 41 | 2 | 1920 | 2880 | 2955 | 1.17 | 3.12 |
| 42 | 2 | 2140 | 6670 | 6790 | 1.06 | 2.21 |
| 46 | 4 | 1930 | 1528 | 1532 | 2.55 | 6.24 |
| 51 | 2 | 1015 | 3722 | 3730 | 1.15 | 3.84 |
| 52 | 4 | 3075 | 2708 | 2730 | 1.09 | 5.5 |
| 54 | 4 | 1290 | 5530 | 5690 | 0.98 | 3.86 |
| 55 | 4 | 2335 | 1938 | 1954 | 0.79 | 3.5 |
| 56 | 4 | 1640 | 6650 | 6780 | 0.96 | 3.65 |
| 59 | 2 | 2060 | 1260 | 1265 | 0.86 | 2.23 |
| 60 | 2 | 1300 | 3770 | 3790 | 0.88 | 2.26 |
| 61 | 2 | 2645 | 2109 | 2121 | 0.75 | 2.96 |
| 62 | 2 | 2810 | 4020 | 4055 | 0.85 | 2.98 |
| 63 | 2 | 2065 | 4990 | 4028 | 0.91 | 2.7 |
| 65 | 2 | 3175 | 2908 | 3390 | 1.02 | 3.72 |
| 66 | 4 | 1881 | 2479 | 2535 | 1 | 3.6 |
| 67 | 4 | 2840 | 3990 | 4070 | 0.88 | 4.17 |

It can be seen from the results of the pharmacokinetic test in rats shown in the table that: the example compounds of the present invention showed good pharmacokinetic properties, and both the exposure AUC and the maximum plasma concentration $C_{max}$ performed well.

7. Procedures and Results Of Pharmacodynamics Test in Vivo

7.1 Experimental Purpose

Compounds with higher efficacy and lower toxicity and side effects were screened by pharmacodynamic experiments in vivo.

7.2 Experimental Instruments and Reagents

7.2.1 Instruments

1. Ultra clean workbench (BSC-1300II A2, Medical equipment factory of Shanghai Boxun Industrial Co., Ltd.)
2. $CO_2$ incubator (Thermo)
3. Centrifugal machine (Centrifuge 5720R, Eppendorf)
4. Automatic cell counter (Countess II, Life)
5. Pipette (10-20 uL, Eppendorf)
6. Microscope (TS100, Nikon)
6. Vernier caliper (500-196, Mitutoyo, Japan)
7. Cell culture bottle (T25/T75/T225, Corning)

7.2.2 Reagents

1. MEM culture medium (11095-080, gibico)
2. Fetal bovine serum (FBS) (10099-141, gibico)
3. 0.25% trypsin (25200-056, gibico)
4. Penicillin-streptomycin solution (SV30010, GE)
5. Phosphate buffer (PBS) (10010-023, gibico)

7.3 Experimental Procedures

7.3.1 Cell Culture and Preparation of Cell Suspension a, A Hep 3B cell line was taken from the cell bank, and the cells were resuscitated with the MEM culture medium (MEM+10% FBS+1% Glu+1% SP). The cells were placed in the cell culture bottle after resuscitation (cell type, date, and the name of the culturing person were marked on the bottle wall) and were incubated in a $CO_2$ Incubator (the incubator temperature was 37° C., and the $CO_2$ concentration was 5%).

b, The cells were passaged after 80-90% of the bottom of the culture bottle was covered by the cells. After passage, the cells were further incubated in the $CO_2$ incubator. The process was repeated until the number of cells met the pharmacodynamic requirements in vivo.

c, The cultured cells were collected and counted by automatic cell counter. According to the counting results, the cells were resuspended with PBS to prepare a cell suspension (density: $7\times10^7$/mL), which was placed in the ice box for use.

7.3.2 Cell Inoculation and Tumor Volume Measurement:

a, Nude mouse was marked with a disposable universal ear tag for mouse and rat before inoculation, and the skin of the inoculated site was disinfected with 75% medical alcohol.

b, At the time of inoculation, the cell suspension was mixed well, 0.1~1 mL of cell suspension was taken with a 1 mL syringe, after removing air bubbles, and the syringe was placed on an ice bag for use.

c, The nude mice were inoculated successively (the inoculated site was located on the right shoulder of the right back of the nude mice, and inoculated subcutaneously with 0.1 mL of cell suspension).

7.3.3 Tumor Volume Measurement, Grouping and Administration in Tumor-Bearing Mice a, Tumor was measured on Day 14 to Day 16 after inoculation depending on the tumor growth, and tumor size was calculated.

Tumor volume calculation: tumor volume $(mm^3)$=length (mm)×width (mm)×width (mm)/2 b, According to the size of the tumor, the mice were grouped by random grouping.

c, According to the results of the grouping, the test drug was administered (administration method: oral administration, administration dose: 30 mg/kg, administration volume: 10 mL/kg, administration frequency: 2 times/day, administration period: 14 days, vehicle: 0.5% CMC/1% Tween 80).

d, The tumor was measured and weighed twice a week after the test drug was administrated.

e, Animals were euthanized at the end of the test.

7.4 Experimental Data:

| Grouping | Number of animals | Days of administration | Tumor inhibition rate |
|---|---|---|---|
| Blank control | 5 | 14 | — |
| Example 6 | 5 | 9 | 78.24% |
| Example 23 | 5 | 10 | 89.85% |
| Example 25 | 5 | 10 | 68.39% |
| Example 28 | 5 | 9 | 74.35% |
| Example 29 | 5 | 14 | 181.67% |
| Example 42 | 5 | 14 | 102.67% |
| Example 55 | 5 | 9 | 32.98% |
| Example 56 | 5 | 9 | 46.39% |
| Example 59 | 5 | 9 | 86.72% |
| Example 65 | 5 | 14 | 129.57% |

It can be seen from the above results that the above example compounds of the present invention had good tumor inhibition rate.

What is claimed is:

1. A compound of formula (III):

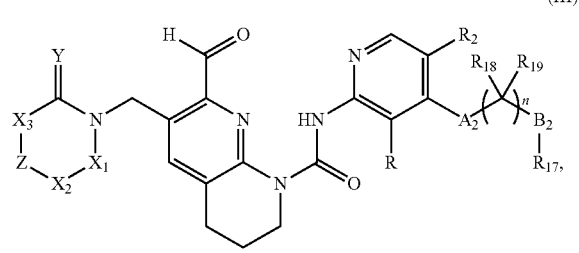

or a stereoisomer or a pharmaceutically acceptable salt thereof, wherein:

$X_1$ is —$(CR_3R_4)m_1$—; $X_2$ is —$(CR_5R_6)m_2$—; $X_3$ is —$(CR_7R_8)m_3$—;

$R_3$, $R_4$, $R_5$, $R_6$, $R_7$ and $R_8$ are each independently selected from the group consisting of hydrogen, deuterium, halogen, $C_{2-8}$ alkenyl, $C_{2-8}$ alkynyl, halo$C_{1-8}$ alkyl, $C_{3-8}$ cycloalkyl, 3-8 membered heterocyclyl, $C_{1-8}$ alkoxy, halo$C_{1-8}$ alkoxy, $C_{3-8}$ cycloalkoxy and 3-8 membered heterocyclyloxy, or, $R_3$ and $R_4$, $R_5$ and $R_6$, or $R_7$ and $R_8$ together with the carbon atom to which they are directly attached form a 3-5 membered cycloalkyl or 3-5 membered heterocyclyl;

Y is selected from the group consisting of oxygen and sulfur;

Z is selected from the group consisting of $NX_4$, oxygen and sulfur;

$X_4$ is selected from the group consisting of hydrogen, deuterium, $C_{3-8}$ cycloalkyl and halo$C_{1-8}$ alkyl;

$A_2$ is selected from the group consisting of a bond, $NX_4$, oxygen and sulfur;

$B_2$ is selected from the group consisting of methyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl ethylpentyl, 2-methyl-3-ethylpentyl, $C_{1-8}$ alkoxy and $C_{1-8}$ alkoxysubstituted $C_{1-8}$ alkyl;

R is selected from the group consisting of hydrogen, deuterium, halogen, hydroxy, thiol, cyano, nitro, azido, $C_{1-8}$ alkyl, halo$C_{1-8}$ alkyl, $C_{3-8}$ cycloalkyl and 3-8 membered heterocyclyl;

$R_2$ is selected from the group consisting of halogen, hydroxy, thiol, cyano, thiocyano, nitro, azido, $C_{1-8}$ alkyl, $C_{2-8}$ alkenyl, $C_{2-8}$ alkynyl, $C_{3-8}$ cycloalkyl, 3-8 membered heterocyclyl, $C_{1-8}$ alkyloxy, $C_{3-8}$ cycloalkoxy and 3-8 membered heterocyclyloxy, wherein the hydroxy, thiol, $C_{1-8}$ alkyl, $C_{2-8}$ alkenyl, $C_{2-8}$ alkynyl, $C_{3-8}$ cycloalkyl, 3-8 membered heterocyclyl, $C_{1-8}$ alkyloxy, $C_{3-8}$ cycloalkoxy and 3-8 membered heterocyclyloxy is optionally substituted by one or more groups selected from the group consisting of halogen, hydroxy, thiol, cyano, nitro, azido, $C_{1-8}$ alkyl, $C_{2-8}$ alkenyl, $C_{2-8}$ alkynyl, halo$C_{1-8}$ alkyl, $C_{3-8}$ cycloalkyl, 3-8 membered heterocyclyl, 3-8 membered heterocyclyloxy, 3-8 membered heterocyclylthio, $C_{5-10}$ aryl, $C_{5-10}$ aryloxy, $C_{5-10}$ arylthio, 5-10 membered heteroaryl, 5-10 membered heteroaryloxy, 5-10 membered heteroarylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—C(O)R$_{11}$, —$C_{0-8}$—NR$_{12}$R$_{13}$, —$C_{0-8}$—C(O)NR$_{12}$R$_{13}$, —N(R$_{12}$)—C(O)R$_{11}$ and —N(R$_{12}$)—C(O)OR$_{10}$;

$R_9$ is selected from the group consisting of hydrogen, deuterium, $C_{1-8}$ alkyl, $C_{2-8}$ alkenyl, $C_{3-8}$ cycloalkyl, 3-8 membered heterocyclyl, halo$C_{1-8}$ alkyl, phenyl, p-methylphenyl, amino, mono $C_{1-8}$ alkylamino, di $C_{1-8}$ alkylamino and $C_{1-8}$ alkanoylamino;

$R_{10}$ is selected from the group consisting of hydrogen, deuterium, $C_{1-8}$ alkyl, $C_{3-8}$ cycloalkyl, $C_{5-10}$ aryl, 3-8 membered heterocyclyl, halo$C_{1-8}$ alkyl and hydroxy$C_{1-8}$ alkyl;

$R_{11}$ is selected from the group consisting of hydrogen, deuterium, $C_{1-8}$ alkyl, $C_{1-8}$ alkoxy, $C_{3-8}$ cycloalkyl, $C_{3-8}$ cycloalkoxy, halo$C_{1-8}$ alkyl, halo$C_{1-8}$ alkoxy, hydroxy$C_{1-8}$ alkyl and hydroxy$C_{1-8}$ alkoxy;

$R_{12}$ and $R_{13}$ are each independently selected from the group consisting of hydrogen, deuterium, $C_{1-8}$ alkyl, $C_{1-8}$ alkoxy-substituted $C_{1-8}$ alkyl, $C_{3-8}$ cycloalkyl-substituted $C_{1-8}$ alkyl, $C_{2-8}$ alkenyl, $C_{2-8}$ alkynyl, $C_{3-8}$ cycloalkyl, 3-8 membered heterocyclyl, $C_{5-10}$ aryl, 5-10 membered heteroaryl and $C_{1-8}$ alkanoyl;

$R_{17}$ is selected from the group consisting of $C_{1-8}$ alkyl, halogen, halo$C_{1-8}$ alkyl, $C_{3-8}$ cycloalkyl, 3-8 membered heterocyclyl, 3-8 membered heterocyclyloxy, 3-8 membered heterocyclylthio, —$C_{0-8}$—S(O)$_r$R$_9$, —$C_{0-8}$—O—R$_{10}$, —$C_{0-8}$—C(O)OR$_{10}$, —$C_{0-8}$—C(O)R$_{11}$, —$C_{0-8}$—O—$C(O)R_{11}$, —$C_{0-8}$—$NR_{12}R_{13}$, —$C_{0-8}$—$C(O)NR_{12}R_{13}$, —$N(R_{12})$—$C(O)R_{11}$ and —$N(R_{12})$—$C(O)OR_{10}$;

$R_{18}$ and $R_{19}$ are each independently selected from the group consisting of halogen, hydroxy, alkyl, halo$C_{1-8}$ alkyl, $C_{3-8}$ cycloalkyl, 3-8 membered heterocyclyl, 3-8 membered heterocyclyloxy, 3-8 membered heterocyclylthio, —$C_{0-8}$—$S(O)_rR_9$, —$C_{0-8}$—O—$R_{10}$, —$C_{0-8}$—$C(O)OR_{10}$, —$C_{0-8}$—$C(O)R_{11}$, —$C_{0-8}$—O—$C(O)R_{11}$, —$C_{0-8}$—$NR_{12}R_{13}$, —$C_{0-8}$—$C(O)NR_{12}R_{13}$, —$N(R_{12})$—$C(O)R_{11}$ and —$N(R_{12})$—$C(O)OR_{10}$;

or R18 and R19 together with the carbon atom to which they are directly attached form a cycloalkyl or heterocyclyl, wherein the cycloalkyl or heterocyclyl is optionally substituted by one or more groups selected from the group consisting of $C_{1-8}$ alkyl, halo$C_{1-8}$ alkyl, halogen, hydroxy, $C_{1-8}$ alkoxy and hydroxy$C_{1-8}$ alkyl;

n is selected from the group consisting of 0, 1, 2, 3 and 4;

$m_1$ is 2, $m_2$ is 2 and $m_3$ is 0, or $m_1$ is 2, $m_2$ is 1 and $m_3$ is 1; and r is 0, 1 or 2.

2. A compound of formula (III):

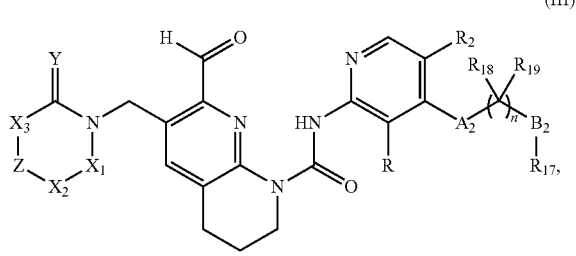

(III)

or a stereoisomer or a pharmaceutically acceptable salt thereof, wherein:

$X_1$ is —$(CR_3R_4)m_1$—; $X_2$ is —$(CR_5R_6)m_2$—; $X_3$ is —$(CR_7R_8)m_3$—,

Y is selected from the group consisting of oxygen and sulfur;

Z is selected from the group consisting of $NX_4$, oxygen and sulfur;

$X_4$ is selected from the group consisting of hydrogen, deuterium, $C_{3-8}$ cycloalkyl and halo$C_{1-8}$ alkyl;

$A_2$ is selected from the group consisting of a bond, $NX_4$, oxygen and sulfur;

$R_{18}$ and $R_{19}$ are each independently selected from the group consisting of halogen, hydroxy, alkyl, halo$C_{1-8}$ alkyl, $C_{3-8}$ cycloalkyl, 3-8 membered heterocyclyl, 3-8 membered heterocyclyloxy, 3-8 membered heterocyclylthio, —$C_{0-8}$—$S(O)_rR_9$, —$C_{0-8}$—O—$R_{10}$, —$C_{0-8}$—$C(O)OR_{10}$, —$C_{0-8}$—$C(O)R_{11}$, —$C_{0-8}$—O—$C(O)R_{11}$, —$C_{0-8}$—$NR_{12}R_{13}$, —$C_{0-8}$—$C(O)NR_{12}R_{13}$, —$N(R_{12})$—$C(O)R_{11}$ and —$N(R_{12})$—$C(O)OR_{10}$;

or $R_{18}$ and $R_{19}$ together with the carbon atom to which they are directly attached form a cycloalkyl or heterocyclyl, wherein the cycloalkyl or heterocyclyl is optionally substituted by one or more groups selected from the group consisting of $C_{1-8}$ alkyl, halo$C_{1-8}$ alkyl, halogen, hydroxy, $C_{1-8}$ alkoxy and hydroxy$C_{1-8}$ alkyl;

$R_9$ is selected from the group consisting of hydrogen, deuterium, $C_{1-8}$ alkyl, $C_{2-8}$ alkenyl, $C_{3-8}$ cycloalkyl, 3-8 membered heterocyclyl, halo$C_{1-8}$ alkyl, phenyl, p-methylphenyl, amino, mono $C_{1-8}$ alkylamino, di $C_{1-8}$ alkylamino and $C_{1-8}$ alkanoylamino;

$R_{10}$ is selected from the group consisting of hydrogen, deuterium, $C_{1-8}$ alkyl, $C_{3-8}$ cycloalkyl, $C_{5-10}$ aryl, 3-8 membered heterocyclyl, halo$C_{1-8}$ alkyl and hydroxy$C_{1-8}$ alkyl;

$R_{11}$ is selected from the group consisting of hydrogen, deuterium, $C_{1-8}$ alkyl, $C_{1-8}$ alkoxy, $C_{3-8}$ cycloalkyl, $C_{3-8}$ cycloalkoxy, halo$C_{1-8}$ alkyl, halo$C_{1-8}$ alkoxy, hydroxy$C_{1-8}$ alkyl and hydroxy$C_{1-8}$ alkoxy;

$R_{12}$ and $R_{13}$ are each independently selected from the group consisting of hydrogen, deuterium, $C_{1-8}$ alkyl, $C_{1-8}$ alkoxy-substituted $C_{1-8}$ alkyl, $C_{3-8}$ cycloalkyl-substituted $C_{1-8}$ alkyl, $C_{2-8}$ alkenyl, $C_{2-8}$ alkynyl, $C_{3-8}$ cycloalkyl, 3-8 membered heterocyclyl, $C_{5-10}$ aryl, 5-10 membered heteroaryl and $C_{1-8}$ alkanoyl;

n is selected from the group consisting of 0, 1, 2, 3 and 4;

$m_1$ is 2, $m_2$ is 2 and $m_3$ is 0, or $m_1$ is 2, $m_2$ is 1 and $m_3$ is 1;

r is 0, 1 or 2;

R is selected from the group consisting of hydrogen and fluorine;

$R_2$ is selected from the group consisting of cyano and thiocyano;

$B_2$ is selected from the group consisting of methyl, methoxy, ethoxy, methoxyethyl, ethoxymethyl and ethoxyethyl;

$R_{17}$ is selected from the group consisting of methyl, methoxy, ethoxy, isopropoxy, cyclopropyl, cyclobutyl, cyclopentyl, cyclopropyloxy, cyclobutyloxy, cyclopentyloxy, furanyl, thienyl, pyrrolyl, imidazolyl, tetrahydrofuranyl, tetrahydrothienyl, tetrahydropyrrolyl, tetrahydroimidazolyl, piperazinyl and morpholinyl; and $R_3$, $R_4$, $R_5$, $R_6$, $R_7$ and $R_8$ are each independently selected from the group consisting of hydrogen, deuterium, fluorine, chlorine, methoxy, ethoxy and isopropoxy;

or, $R_3$, $R_4$, $R_5$, and $R_6$, or $R_7$ and $R_8$ together with the carbon atom to which they are directly attached form a cyclopropyl or cyclobutyl.

3. A compound selected from the group consisting of:

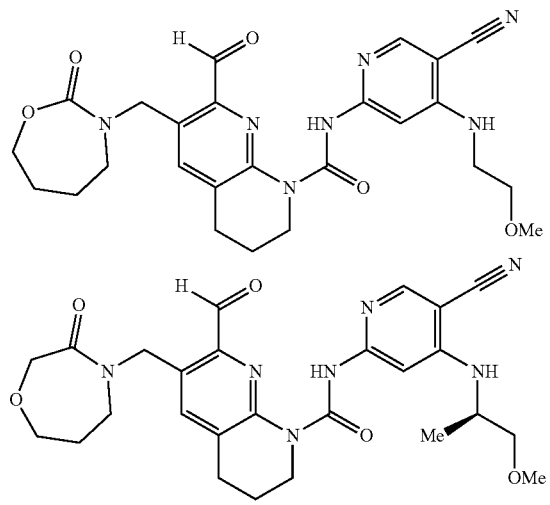

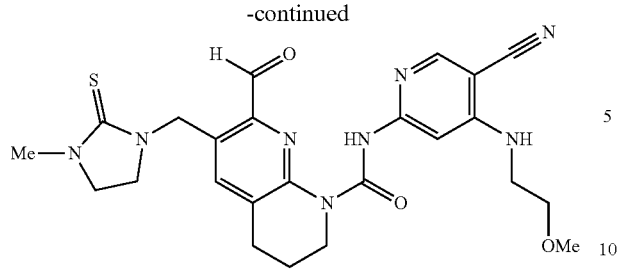

or a stereoisomer or a pharmaceutically acceptable salt therof.

4. The compound, the stereoisomer or the pharmaceutically acceptable salt thereof according to claim 1, wherein,
R is selected from the group consisting of hydrogen and fluorine; and
$R_2$ is cyano.

5. A compound of formula (III):

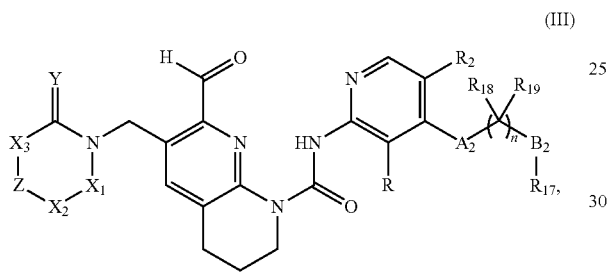

or a stereoisomer or a pharmaceutically acceptable salt thereof,
wherein $R_{17}$ is selected from the group consisting of $C_{1-8}$ alkyl, $C_{1-8}$ alkoxy, halo$C_{1-8}$ alkyl, $C_{3-8}$ cycloalkyl, 3-8 membered heterocyclyl, 3-8 membered heterocyclyloxy and 3-8 membered heterocyclylthio, wherein the $C_{1-8}$ alkyl, $C_{1-8}$ alkoxy, halo$C_{1-8}$ alkyl, $C_{3-8}$ cycloalkyl, 3-8 membered heterocyclyl, 3-8 membered heterocyclyloxy and 3-8 membered heterocyclylthio are each optionally substituted by $C_{1-8}$ alkyl, $C_{1-8}$ alkoxy, halo$C_{1-8}$ alkyl, $C_{3-8}$ cycloalkyl or 3-8 membered heterocyclyl;
$X_1$ is —$(CR_3R_4)m_1$—; $X_2$ is —$(CR_5R_6)m_2$—, $X_3$ is —$(CR_7R_8)m_3$—;
$R_3$, $R_4$, $R_5$, $R_6$, $R_7$ and $R_8$ are each independently selected from the group consisting of hydrogen, deuterium, halogen, $C_{2-8}$ alkenyl, $C_{2-8}$ alkynyl, halo$C_{1-8}$ alkyl, $C_{3-8}$ cycloalkyl, 3-8 membered heterocyclyl, $C_{1-8}$ alkoxy, halo$C_{1-8}$ alkoxy, $C_{3-8}$ cycloalkoxy and 3-8 membered heterocyclyloxy,
or, $R_3$, $R_4$, $R_5$, and $R_6$, or $R_7$ and $R_8$ together with the carbon atom to which they are directly attached form a 3-5 membered cycloalkyl or 3-5 membered heterocyclyl;
Y is selected from the group consisting of oxygen and sulfur;
Z is selected from the group consisting of $NX_4$, oxygen and sulfur;
X4 is selected from the group consisting of hydrogen, deuterium, $C_{3-8}$ cycloalkyl and halo$C_{1-8}$ alkyl;
$A_2$ is selected from the group consisting of a bond, $NX_4$, oxygen and sulfur;

$B_2$ is selected from the group consisting of methyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl ethylpentyl, 2-methyl-3-ethylpentyl, $C_{1-8}$ alkoxy and $C_{1-8}$ alkoxysubstituted $C_{1-8}$ alkyl;
R is selected from the group consisting of hydrogen, deuterium, halogen, hydroxy, thiol, cyano, nitro, azido, $C_{1-8}$ alkyl, halo$C_{1-8}$ alkyl, $C_{3-8}$ cycloalkyl and 3-8 membered heterocyclyl;
$R_2$ is selected from the group consisting of halogen, hydroxy, thiol, cyano, thiocyano, nitro, azido, $C_{1-8}$ alkyl, $C_{2-8}$ alkenyl, $C_{2-8}$ alkynyl, $C_{3-8}$ cycloalkyl, 3-8 membered heterocyclyl, $C_{1-8}$ alkyloxy, $C_{3-8}$ cycloalkoxy and 3-8 membered heterocyclyloxy, wherein the hydroxy, thiol, $C_{1-8}$ alkyl, $C_{2-8}$ alkenyl, $C_{2-8}$ alkynyl, $C_{3-8}$ cycloalkyl, 3-8 membered heterocyclyl, $C_{1-8}$ alkyloxy, $C_{3-8}$ cycloalkoxy and 3-8 membered heterocyclyloxy is optionally substituted by one or more groups selected from the group consisting of halogen, hydroxy, thiol, cyano, nitro, azido, $C_{1-8}$ alkyl, $C_{2-8}$ alkenyl, $C_{2-8}$ alkynyl, halo$C_{1-8}$ alkyl, $C_{3-8}$ cycloalkyl, 3-8 membered heterocyclyl, 3-8 membered heterocyclyloxy, 3-8 membered heterocyclylthio, $C_{5-10}$ aryl, $C_{5-10}$ aryloxy, $C_{5-10}$ arylthio, 5-10 membered heteroaryl, 5-10 membered heteroaryloxy, 5-10 membered heteroarylthio, —$C_{0-8}$—S(O)$_r$$R_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—N$R_{12}R_{13}$, —$C_{0-8}$—C(O)N$R_{12}R_{13}$, —N($R_{12}$)—C(O)$R_{11}$ and —N($R_{12}$)—C(O)O$R_{10}$;
$R_9$ is selected from the group consisting of hydrogen, deuterium, $C_{1-8}$ alkyl, $C_{2-8}$ alkenyl, $C_{3-8}$ cycloalkyl, 3-8 membered heterocyclyl, halo$C_{1-8}$ alkyl, phenyl, p-methylphenyl, amino, mono $C_{1-8}$ alkylamino, di $C_{1-8}$ alkylamino and $C_{1-8}$ alkanoylamino;
$R_{10}$ is selected from the group consisting of hydrogen, deuterium, $C_{1-8}$ alkyl, $C_{3-8}$ cycloalkyl, $C_{5-10}$ aryl, 3-8 membered heterocyclyl, halo$C_{1-8}$ alkyl and hydroxy$C_{1-8}$ alkyl;
$R_{11}$ is selected from the group consisting of hydrogen, deuterium, $C_{1-8}$ alkyl, $C_{1-8}$ alkoxy, $C_{3-8}$ cycloalkyl, $C_{3-8}$ cycloalkoxy, halo$C_{1-8}$ alkyl, halo$C_{1-8}$ alkoxy, hydroxy$C_{1-8}$ alkyl and hydroxy$C_{1-8}$ alkoxy;
$R_{12}$ and $R_{13}$ are each independently selected from the group consisting of hydrogen, deuterium, $C_{1-8}$ alkyl, $C_{1-8}$ alkoxy-substituted $C_{1-8}$ alkyl, $C_{3-8}$ cycloalkyl-substituted $C_{1-8}$ alkyl, $C_{2-8}$ alkenyl, $C_{2-8}$ alkynyl, $C_{3-8}$ cycloalkyl, 3-8 membered heterocyclyl, $C_{5-10}$ aryl, 5-10 membered heteroaryl and $C_{1-8}$ alkanoyl;
$R_{18}$ and $R_{19}$ are each independently selected from the group consisting of halogen, hydroxy, alkyl, halo$C_{1-8}$ alkyl, $C_{3-8}$ cycloalkyl, 3-8 membered heterocyclyl, 3-8 membered heterocyclyloxy, 3-8 membered heterocyclylthio, —$C_{0-8}$—S(O)$_r$$R_9$, —$C_{0-8}$—O—$R_{10}$, —$C_{0-8}$—C(O)O$R_{10}$, —$C_{0-8}$—C(O)$R_{11}$, —$C_{0-8}$—O—C(O)$R_{11}$, —$C_{0-8}$—$NR_{12}R_{13}$, —$C_{0-8}$—$C(O)NR_{12}R_{13}$, —$N(R_{12})$—$C(O)R_{11}$ and —$N(R_{12})$—$C(O)OR_{10}$;

or $R_{18}$ and R19 together with the carbon atom to which they are directly attached form a cycloalkyl or heterocyclyl, wherein the cycloalkyl or heterocyclyl is optionally substituted by one or more groups selected from the group consisting of $C_{1-8}$ alkyl, halo$C_{1-8}$ alkyl, halogen, hydroxy, $C_{1-8}$ alkoxy and hydroxy$C_{1-8}$ alkyl;

n is selected from the group consisting of 0, 1, 2, 3 and 4;

$m_1$ is 2, $m_2$ is 2 and $m_3$ is 0, or $m_1$ is 2, $m_2$ is 1 and $m_3$ is 1; and r is 0, 1 or 2.

6. A pharmaceutical composition comprising a therapeutically effective amount of the compound, the stereoisomer or the pharmaceutically acceptable salt thereof according to claim 1, and a pharmaceutically acceptable carrier.

7. The compound, the stereoisomer or the pharmaceutically acceptable salt thereof according to claim 3, selected from the group consisting of:

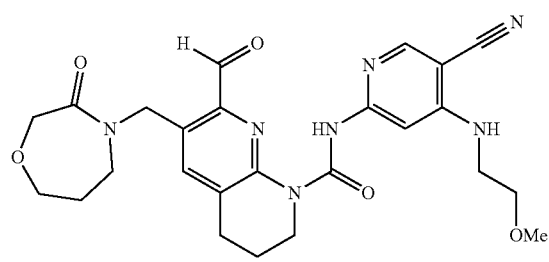

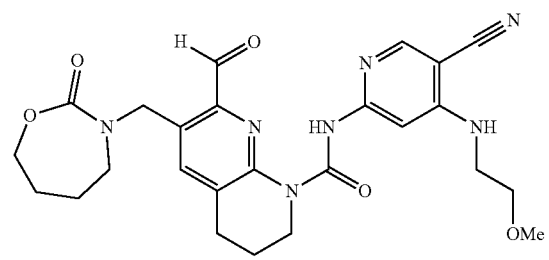

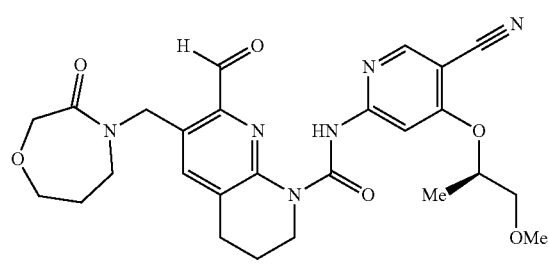

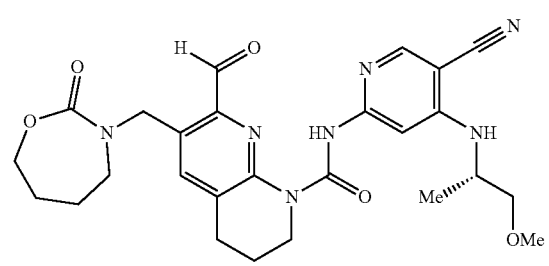

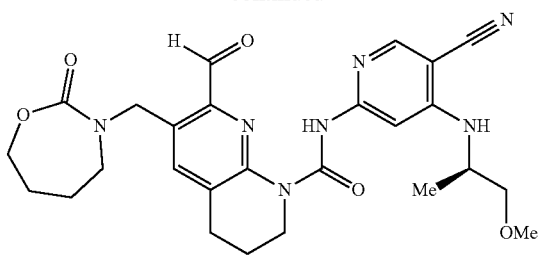

and

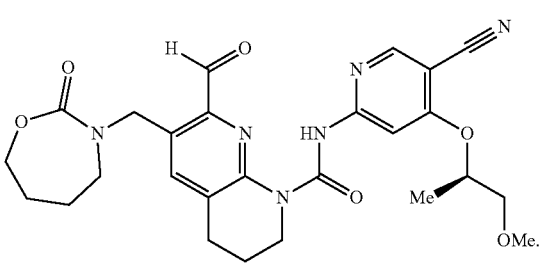

8. A pharmaceutical composition comprising a therapeutically effective amount of the compound, the stereoisomer or the pharmaceutically acceptable salt thereof according to claim 7, and a pharmaceutically acceptable carrier.

9. The compound, the stereoisomer or the pharmaceutically acceptable salt thereof according to claim 3, selected from the group consisting of:

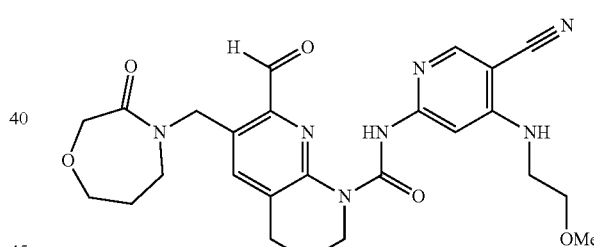

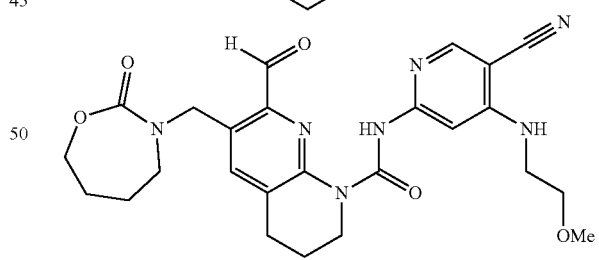

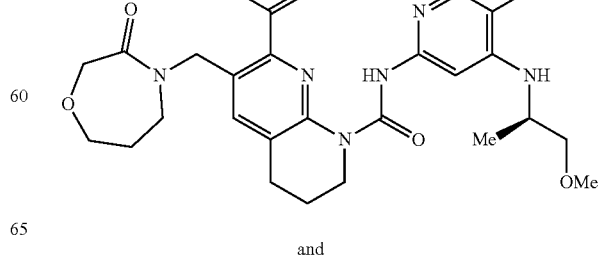

and

-continued

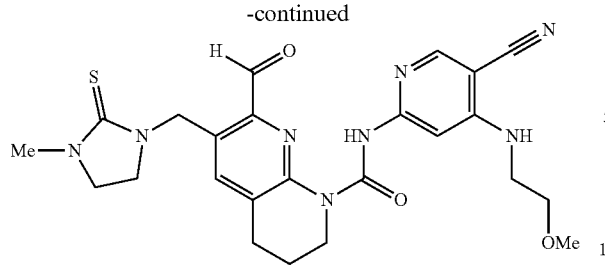

or a stereoisomer or a pharmaceutically acceptable salt thereof.

10. The compound, the stereoisomer or the pharmaceutically acceptable salt thereof according to claim 3, selected from the group consisting of:

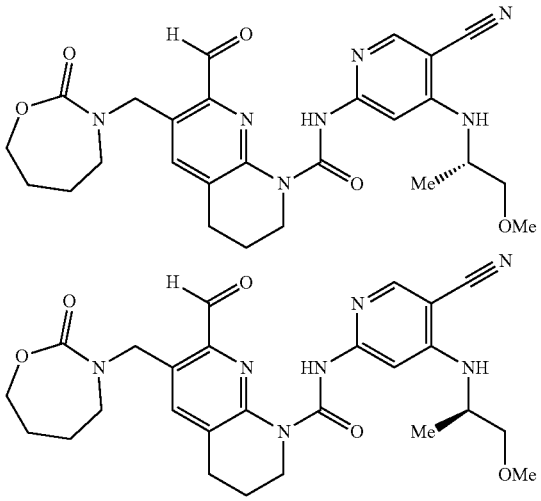

-continued
and

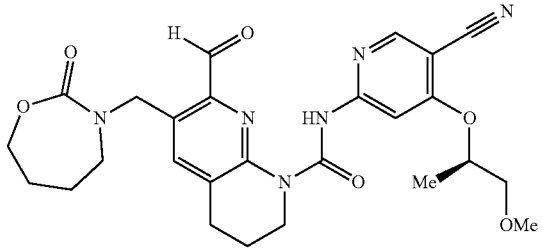

or a stereoisomer or a pharmaceutically acceptable salt thereof.

11. A method for inhibiting FGFG4 in a subject, comprising administering to the subject the pharmaceutical composition according to claim 6.

12. A method for treating FGFR4-related cancer in a subject, comprising administering to the subject the pharmaceutical composition according to claim 6.

13. The method according to claim 12, wherein the cancer is selected from the group consisting of liver cancer, gastric cancer, prostate cancer, skin cancer, ovarian cancer, lung cancer, breast cancer, colon cancer, glioma and rhabdomyosarcoma.

14. A method for inhibiting FGFG4 in a subject, comprising administering to the subject the pharmaceutical composition according to claim 8.

15. A method for treating FGFR4-related cancer in a subject, comprising administering to the subject the pharmaceutical composition according to claim 8.

16. The method according to claim 15, wherein the cancer is selected from the group consisting of liver cancer, gastric cancer, prostate cancer, skin cancer, ovarian cancer, lung cancer, breast cancer, colon cancer, glioma and rhabdomyosarcoma.

* * * * *